(12) United States Patent
Sasada et al.

(10) Patent No.: US 11,339,134 B2
(45) Date of Patent: May 24, 2022

(54) COMPOSITION AND LIGHT EMITTING ELEMENT DEVICE USING THE SAME

(71) Applicant: Sumitomo Chemical Company, Limited, Tokyo (JP)

(72) Inventors: Toshiaki Sasada, Tsukuba (JP); Takashi Kuragano, Tsukuba (JP); Yoshiaki Tsubata, Tsukuba (JP); Makoto Anryu, Tokyo (JP); Takakazu Saito, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 574 days.

(21) Appl. No.: 15/753,760

(22) PCT Filed: Aug. 25, 2016

(86) PCT No.: PCT/JP2016/074785
§ 371 (c)(1),
(2) Date: Feb. 20, 2018

(87) PCT Pub. No.: WO2017/038613
PCT Pub. Date: Mar. 9, 2017

(65) Prior Publication Data
US 2019/0010134 A1 Jan. 10, 2019

(30) Foreign Application Priority Data

Aug. 28, 2015 (JP) .............................. JP2015-168829

(51) Int. Cl.
*C07D 251/24* (2006.01)
*C07C 13/567* (2006.01)
*C08L 65/00* (2006.01)
*C09K 11/06* (2006.01)
*H01L 51/50* (2006.01)
*C07C 211/61* (2006.01)
*C07D 209/82* (2006.01)
*C07D 237/08* (2006.01)
*H01L 51/00* (2006.01)

(52) U.S. Cl.
CPC .......... *C07D 251/24* (2013.01); *C07C 13/567* (2013.01); *C07C 211/61* (2013.01); *C07D 209/82* (2013.01); *C07D 237/08* (2013.01); *C09K 11/06* (2013.01); *H01L 51/0039* (2013.01); *H01L 51/0072* (2013.01); *H01L 51/0085* (2013.01); *H01L 51/50* (2013.01)

(58) Field of Classification Search
CPC ... C07C 13/567; C07C 211/61; C07D 209/82; C07D 237/08; C07D 251/24; C08L 65/00; C09K 11/06; H01L 51/0039; H01L 51/0072; H01L 51/0085; H01L 51/50
See application file for complete search history.

(56) References Cited

U.S. PATENT DOCUMENTS

| 6,517,957 | B1 | 2/2003 | Senoo et al. | |
|---|---|---|---|---|
| 8,034,464 | B2* | 10/2011 | Igawa | C09K 11/06 428/690 |
| 2003/0219625 | A1* | 11/2003 | Wolk | H01L 51/006 428/690 |
| 2007/0232841 | A1* | 10/2007 | Igawa | H01L 51/0052 585/27 |
| 2011/0175072 | A1* | 7/2011 | Ooishi | H01L 51/5016 257/40 |
| 2014/0306190 | A1 | 10/2014 | Lee et al. | |
| 2015/0155495 | A1 | 6/2015 | Asada et al. | |
| 2017/0186965 | A1 | 6/2017 | Parham et al. | |

FOREIGN PATENT DOCUMENTS

| JP | H11-35532 | A | | 2/1999 |
|---|---|---|---|---|
| JP | 2001196177 | A | | 7/2001 |
| JP | 2004224723 | A | | 8/2004 |
| JP | 2007-308376 | A | * | 11/2007 |
| JP | 2009170812 | A | | 7/2009 |
| JP | 2009170819 | A | | 7/2009 |
| JP | 201182238 | A | | 4/2011 |
| WO | 2013191086 | A1 | | 12/2013 |
| WO | 2015-169412 | A1 | | 11/2015 |
| WO | 2017016667 | A1 | | 2/2017 |

OTHER PUBLICATIONS

Google Patents machine translation for JP 2007-308376 A (publication date: Nov. 2007). (Year: 2007).*

(Continued)

*Primary Examiner* — Dawn L Garrett
(74) *Attorney, Agent, or Firm* — Panitch Schwarze Belisario & Nadel LLP

(57) ABSTRACT

A composition which is useful for production of a light emitting device excellent in light emission efficiency is provided. In particular, provided is a composition containing a compound represented by formula (1) and a phosphorescent compound, wherein $R^1$ and $R^2$ each independently represent a substituent, $n^1$ represents an integer of 1 to 14, and $Ar^1$ represents an arylene group or a divalent heterocyclic group, and at least one of one or more groups $Ar^1$ is a group represented by the formula (1-A), wherein the variable groups $R^{1A}$ to $R^{8A}$, $R^{91A}$, and $R^{92A}$ are as defined in the specification.

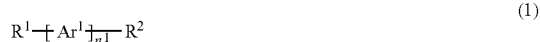

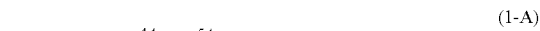

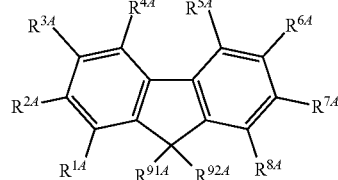

13 Claims, No Drawings

(56) References Cited

OTHER PUBLICATIONS

Journal of Organic Chemistry, (2018), vol. 83, pp. 1065-1072. (Year: 2018).*
Office Action dated Feb. 26, 2020 in JP Application No. 2017537795.
Extended European Search Report dated Apr. 10, 2019 in EP Application No. 16841645.1.
Shih et al., "Synthesis of Fluorene-based Hyperbranched Polymers for Solution-Processable Blue, Green, Red, and White Light-Emitting Devices", Polymer Chemistry, 50, pp. 696-710, 2012.

* cited by examiner

COMPOSITION AND LIGHT EMITTING ELEMENT DEVICE USING THE SAME

CROSS-REFERENCE TO RELATED APPLICATION

This application is a Section 371 International Application No. PCT/JP2016/074785, filed Aug. 25, 2016, which was published in the Japanese language on Mar. 9, 2017 under International Publication No. WO 2017/038613 A1, which claims priority under 35 U.S.C. § 119(b) to Japanese Application No. 2015-168829, filed Aug. 28, 2015, the disclosures of which are incorporated herein by reference in their entirety.

TECHNICAL FIELD

The present invention relates to a composition and a light emitting device using the same.

BACKGROUND ART

Light emitting devices such as an organic electroluminescent device can be suitably used for applications of display and illumination. As the light emitting material used in a light emitting layer of a light emitting device, for example, a composition comprising a fluorene compound 1 represented by the following formula and Ir(ppy)$_3$ represented by the following formula is known (Patent document 1)

[Chemical Formula 1]

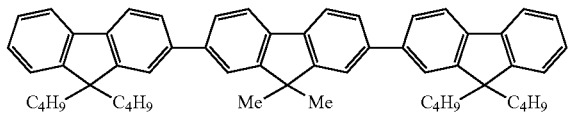

Fluorene compound 1

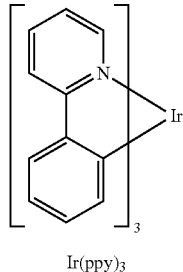

Ir(ppy)$_3$

PRIOR ART DOCUMENT

Patent Document

Patent document 1: JP-A No. 2009-170812

SUMMARY OF THE INVENTION

Problem to be Solved by the Invention

However, a light emitting device produced by using this composition is not always sufficient in light emission efficiency.

Accordingly, the present invention has an object of providing a composition which is useful for production of a light emitting device excellent in light emission efficiency.

Further, the present invention has an object of providing a light emitting device comprising this composition.

Means for Solving the Problem

The present invention provides the following [1] to [14].

[1] A composition comprising a compound represented by the formula (1) and a phosphorescent compound:

[Chemical Formula 2]

[wherein,

R$^1$ and R$^2$ each independently represent an aryl group, a monovalent heterocyclic group or a substituted amino group, and these groups each optionally have a substituent.

n$^1$ represents an integer of 1 to 14.

Ar$^1$ represents an arylene group or a divalent heterocyclic group, and these groups each optionally have a substituent. When a plurality of Ar$^1$ are present, they may be the same or different. At least one of one or more groups Ar$^1$ is a group represented by the formula (1-A).]

[Chemical Formula 3]

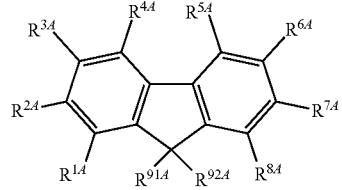

[wherein,

R$^{1A}$, R$^{2A}$, R$^{3A}$, R$^{4A}$, R$^{5A}$, R$^{6A}$, R$^{7A}$ and R$^{8A}$ each independently represent a connecting bond, a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. One of R$^{1A}$, R$^{2A}$, R$^{3A}$, and R$^{4A}$, is a connecting bond, and one of R$^{5A}$, R$^{6A}$, R$^{7A}$ and R$^{8A}$ is a connecting bond.

R$^{1A}$ and R$^{2A}$, R$^{2A}$ and R$^{3A}$, R$^{3A}$ and R$^{4A}$, R$^{4A}$ and R$^{5A}$, R$^{5A}$ and R$^{6A}$, R$^{6A}$ and R$^{7A}$, and R$^{7A}$ and R$^{8A}$ each may be combined together to form a ring together with the carbon atoms to which they are attached.

R$^{91A}$ represents an alkyl group, a cycloalkyl group, an alkoxy group, a cycloalkoxy group or a halogen atom, and these groups each optionally have a substituent.

R$^{92A}$ represents an aryl group or a monovalent heterocyclic group, and these groups each optionally have a substituent.]

[2] The composition according to [1], wherein one of R$^{2A}$ and R$^{3A}$ is a connecting bond, and one of R$^{6A}$ and R$^{7A}$ is a connecting bond.

[3] The composition according to [1] or [2], wherein R$^{91A}$ is an alkyl group optionally having a substituent or a cycloalkyl group optionally having a substituent.

[4] The composition according to any one of [1] to [3], wherein R$^{92A}$ is an aryl group optionally having a substituent.

[5] The composition according to any one of [1] to [4], wherein $R^1$ and $R^2$ represent a group represented by the formula (D-A), a group represented by the formula (D-B) or a group represented by the formula (D-C):

[Chemical Formula 4]

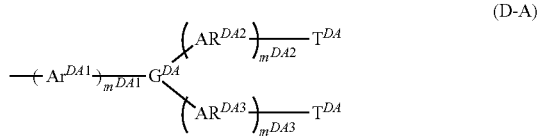

(D-A)

[wherein,
$m^{DA1}$, $m^{DA2}$ and $m^{DA3}$ each independently represent an integer of 0 or more.
$G^{DA}$ represents a nitrogen atom, an aromatic hydrocarbon group or a heterocyclic group, and these groups each optionally have a substituent.
$Ar^{DA1}$, $Ar^{DA2}$ and $Ar^{DA3}$ each independently represent an arylene group or a divalent heterocyclic group, and these groups each optionally have a substituent. When a plurality of $Ar^{DA1}$, $Ar^{DA2}$ and $Ar^{DA3}$ are present, they may be the same or different at each occurrence.
$T^{DA}$ represents an aryl group or a monovalent heterocyclic group, and these groups each optionally have a substituent. The plurality of $T^{DA}$ may be the same or different.]

[Chemical Formula 5]

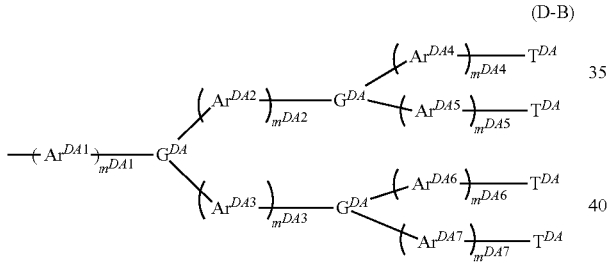

(D-B)

[wherein,
$m^{DA1}$, $m^{DA2}$, $m^{DA3}$, $m^{DA4}$, $m^{DA5}$, $m^{DA6}$ and $m^{DA7}$ each independently represent an integer of 0 or more.
$G^{DA}$ represents a nitrogen atom, an aromatic hydrocarbon group or a heterocyclic group, and these groups each optionally have a substituent. The plurality of $G^{DA}$ may be the same or different.
$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and these groups each optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.
$T^{DA}$ represents an aryl group or a monovalent heterocyclic group, and these groups each optionally have a substituent. The plurality of $T^{DA}$ may be the same or different.]

[Chemical Formula 6]

(D-C)

[wherein,
$m^{DA1}$ represents an integer of 0 or more.
$Ar^{DA1}$ represents an arylene group or a divalent heterocyclic group, and these groups each optionally have a substituent. When a plurality of $Ar^{DA1}$ are present, they may be the same or different.
$T^{DA}$ represents an aryl group or a monovalent heterocyclic group, and these groups each optionally have a substituent.].

[6] The composition according to [5], wherein the group represented by the formula (D-A) is a group represented by the formula (D-A1), a group represented by the formula (D-A2), a group represented by the formula (D-A3) or a group represented by the formula (D-A4):

[Chemical Formula 7]

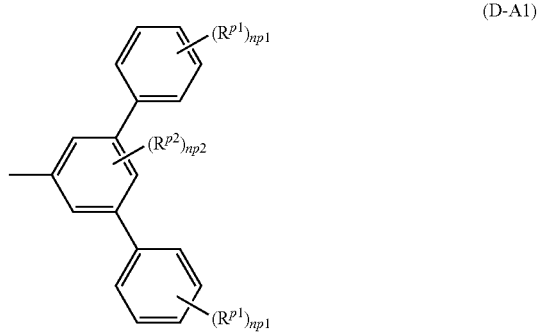

(D-A1)

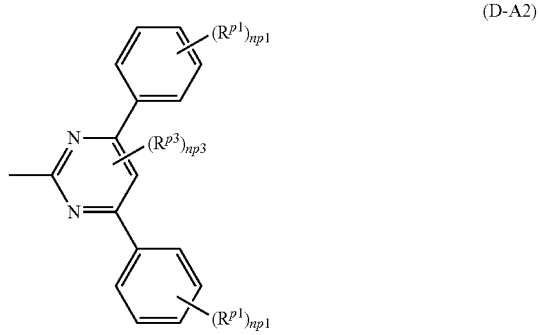

(D-A2)

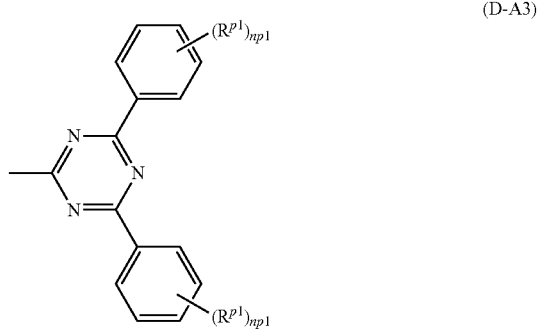

(D-A3)

-continued

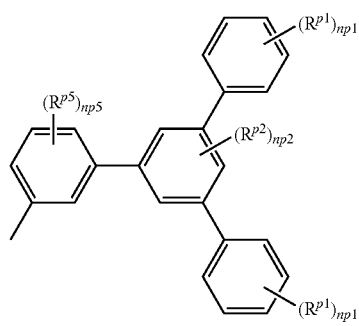
(D-A4)

[wherein, $R^{p1}$, $R^{p2}$, $R^{p3}$ and $R^{p5}$ each independently represent an alkyl group, a cycloalkyl group, an alkoxy group, a cycloalkoxy group or a halogen atom. When a plurality of $R^{p1}$, $R^{p2}$ and $R^{p5}$ are present, they may be the same or different at each occurrence.

np1 represents an integer of 0 to 5, np2 represents an integer of 0 to 3, np3 represents 0 or 1, and np5 represents an integer of 0 to 4. The plurality of np1 may be the same or different.].

[7] The composition according to [5], wherein the group represented by the formula (D-B) is a group represented by the formula (D-B1), a group represented by the formula (D-B2) or a group represented by the formula (D-B3):

[Chemical Formula 8]

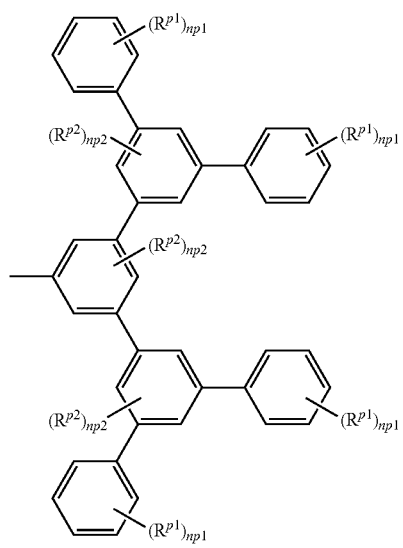
(D-B1)

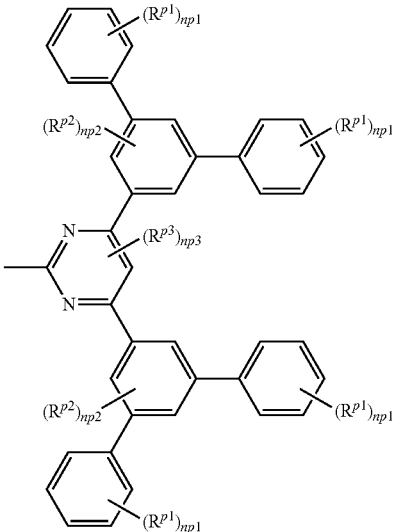
(D-B2)

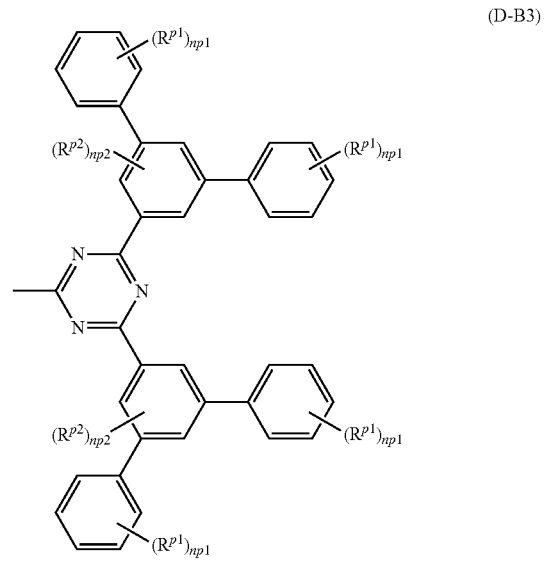
(D-B3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 and np2 may be the same or different at each occurrence.].

[8] The composition according to [5], wherein the group represented by the formula (D-C) is a group represented by the formula (D-C1), a group represented by the formula (D-C2), a group represented by the formula (D-C3) or a group represented by the formula (D-C4):

[Chemical Formula 9]

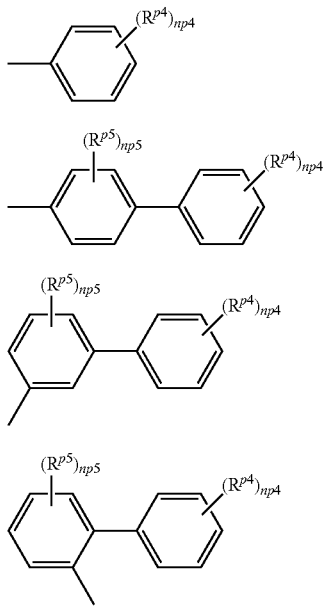

[wherein, $R^{p4}$ and $R^{p5}$ each independently represent an alkyl group, a cycloalkyl group, an alkoxy group, a cycloalkoxy group or a halogen atom. When a plurality of $R^{p4}$ and $R^{p5}$ are present, they may be the same or different at each occurrence.

np4 represents an integer of 0 to 5, and np5 represents an integer of 0 to 4.].

[9] The composition according to any one of [1] to [8], wherein all of $n^1$ groups $Ar^1$ are groups represented by the formula (1-A).

[10] The composition according to any one of [1] to [9], wherein the phosphorescent compound is a metal complex represented by the formula (M):

[Chemical Formula 10]

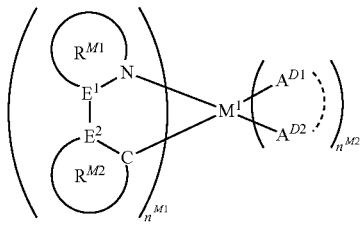

[wherein, $M^1$ represents an iridium atom or a platinum atom.

$n^{M1}$ represents an integer of 1 or more, $n^{M2}$ represents an integer of 0 or more, and $n^{M1}+n^{M2}$ is 2 or 3. $n^{M1}+n^{M2}$ is 3 when $M^1$ is an iridium atom, while $n^{M1}+n^{M2}$ is 2 when $M^1$ is a platinum atom.

$E^1$ and $E^2$ each independently represent a carbon atom or a nitrogen atom. At least one of $E^1$ and $E^2$ is a carbon atom.

The ring $R^{M1}$ represents an aromatic heterocyclic ring, and this ring optionally has a substituent. When a plurality of the substituents are present, they may be the same or different and may be combined together to form a ring together with the atoms to which they are attached. When a plurality of the rings $R^{M1}$ are present, they may be the same or different.

The ring $R^{M2}$ represents an aromatic hydrocarbon ring or an aromatic heterocyclic ring, and these rings each optionally have a substituent. When a plurality of the substituents are present, they may be the same or different and may be combined together to form a ring together with the atoms to which they are attached. When a plurality of the rings $R^{M2}$ are present, they may be the same or different.

The substituent which the ring $R^{M1}$ optionally has and the substituent which the ring $R^{M2}$ optionally has may be combined together to form a ring together with the atoms to which they are attached.

-$A^{D1}$---$A^{D2}$- represents an anionic bidentate ligand, and $A^{D1}$ and $A^{D2}$ each independently represent a carbon atom, an oxygen atom or a nitrogen atom bonding to an iridium atom, and these atoms may be an atom constituting a ring. When a plurality of -$A^{D1}$---$A^{D2}$- are present, they may be the same or different.].

[11] The composition according to [10], wherein the metal complex represented by the formula (M) is a metal complex represented by the formula Ir-1, a metal complex represented by the formula Ir-2, a metal complex represented by the formula Ir-3, a metal complex represented by the formula Ir-4 or a metal complex represented by the formula Ir-5:

[Chemical Formula 11]

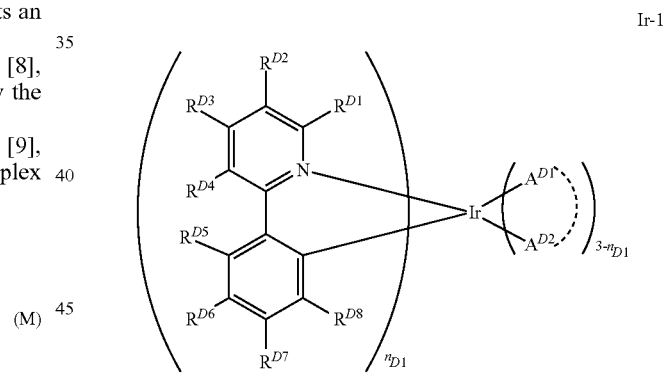

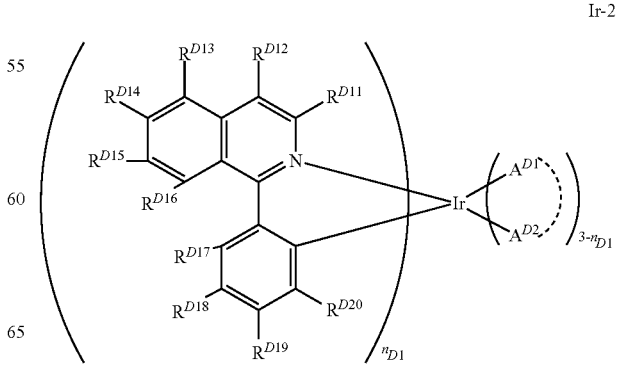

-continued

[Chemical Formula 12]

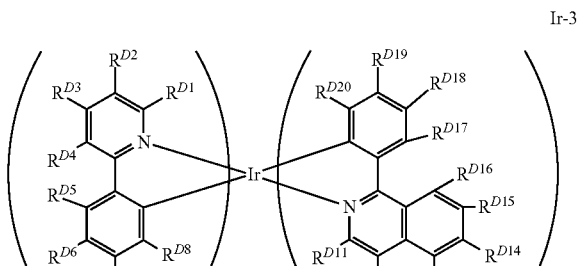

Ir-3

[Chemical Formula 13]

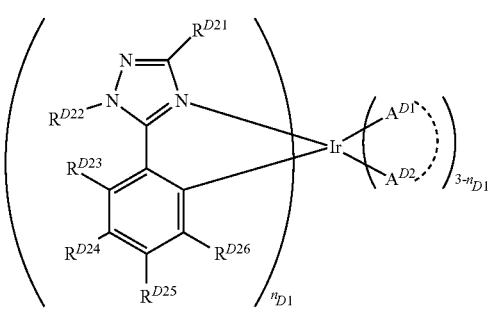

Ir-4

Ir-5

[wherein,
$R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$, and $R^{D37}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, $R^{D20}$, $R^{D21}$, $R^{D22}$, $R^{D23}$, $R^{D24}$, $R^{D25}$, $R^{D26}$, $R^{D31}$, $R^{D32}$, $R^{D33}$, $R^{D34}$, $R^{D35}$, $R^{D36}$, and $R^{D37}$ are present, they may be the same or different at each occurrence.

-$A^{D1}$---$A^{D2}$- represents the same meaning as described above.

$n_{D1}$ represents 1, 2 or 3, and $n_{D2}$ represents 1 or 2.].

[12] The composition according to any one of [1] to [11], further comprising at least one material selected from the group consisting of a hole transporting material, a hole injection material, an electron transporting material, an electron injection material, a light emitting material and an antioxidant.

[13] The composition according to any one of [1] to [12], further comprising a solvent.

[14] A light emitting device comprising the composition according to any one of [1] to [12].

Effect of the Invention

The present invention can provide a composition which is useful for production of a light emitting device excellent in light emission efficiency. Further, the present invention can provide a light emitting device comprising this composition.

MODES FOR CARRYING OUT THE INVENTION

Suitable embodiments of the present invention will be illustrated in detail below.

<Explanation of Common Term>

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

A solid line representing a bond to a central metal in a formula representing a metal complex denotes a covalent bond or a coordinate bond.

"Polymer compound" denotes a polymer having molecular weight distribution and having a polystyrene-equivalent number average molecular weight of $1 \times 10^3$ to $1 \times 10^8$.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes, for example, groups bonding to an aryl group or a monovalent heterocyclic group via a carbon-carbon bond.

"Tow molecular weight compound" denotes a compound having no molecular weight distribution and having a molecular weight of $1 \times 10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group, and groups obtained by substituting a hydrogen atom in these groups with a cycloalkyl group, an alkoxy group, a cycloalkoxy group, an aryl group, a fluorine atom or the like, and the alkyl group having a substituent includes a trifluoromethyl group, a pentafluoroethyl group, a perfluorobutyl group, a perfluorohexyl group, a perfluorooctyl group, a 3-phenylpropyl group, a 3-(4-methylphenyl) propyl group, a 3-(3,5-di-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent, and example s thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauryloxy group, and groups obtained by substituting a hydrogen atom in these groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 6 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidinyl group, a quinolinyl group, an isoquinolinyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

[Chemical Formula 14]

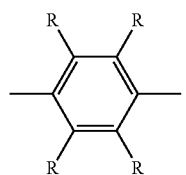
(A-1)

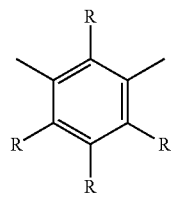
(A-2)

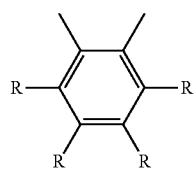
(A-3)

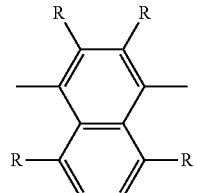
(A-4)

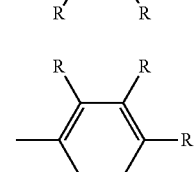
(A-5)

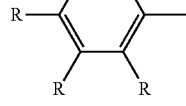

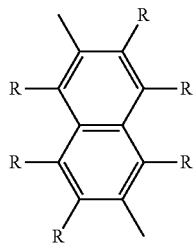
(A-6)

[Chemical Formula 15]

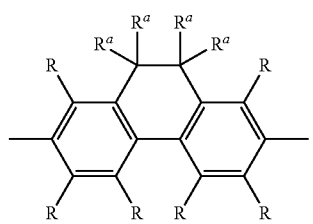
(A-7)

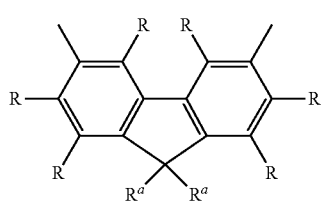
(A-8)

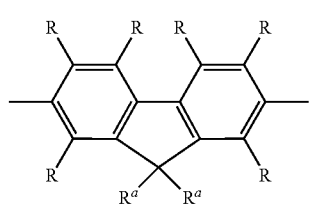
(A-9)

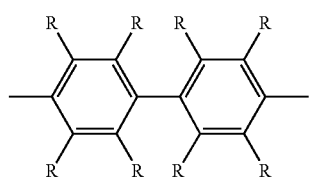
(A-10)

[Chemical Formula 16]

(A-11)

(A-12)
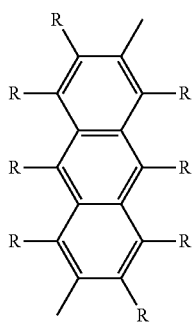

(A-13)
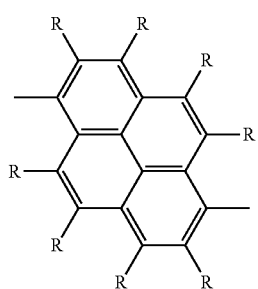

(A-14)
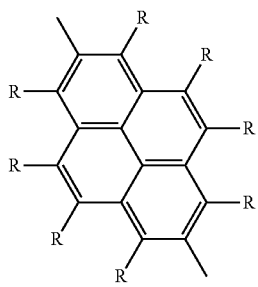

(A-15)
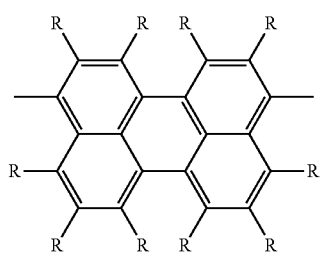

[Chemical Formula 17]

(A-16)
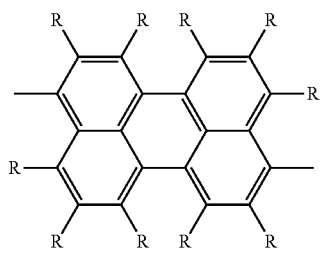

(A-17)
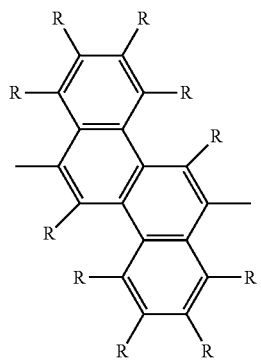

(A-18)
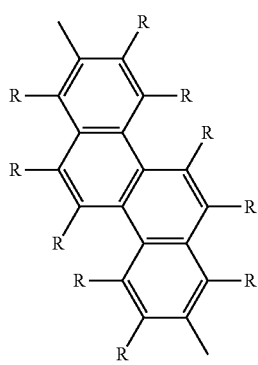

(A-19)

(A-20)
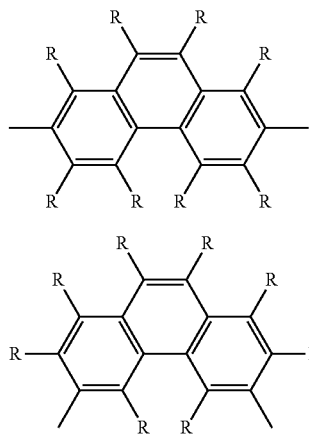

[wherein, R and $R^a$ each independently represent a hydrogen atom, an alkyl group, a cycloalkyl group, an aryl group or a monovalent heterocyclic group. The plurality of R and $R^a$ each may be the same or different, and groups $R^a$ may be combined together to form a ring together with the atoms to which they are attached.]

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.
[Chemical Formula 18]
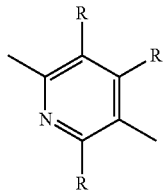
(AA-1)
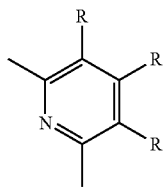
(AA-2)
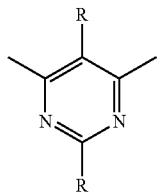
(AA-3)
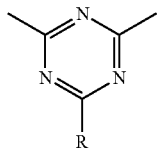
(AA-4)
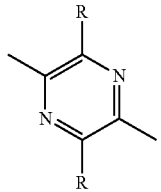
(AA-5)
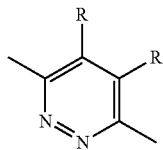
(AA-6)
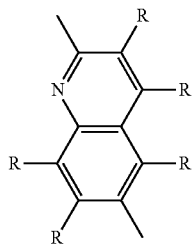
(AA-7)
[Chemical Formula 19]
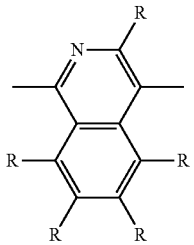
(AA-8)
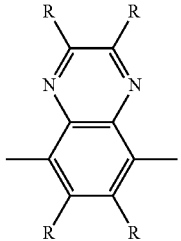
(AA-9)
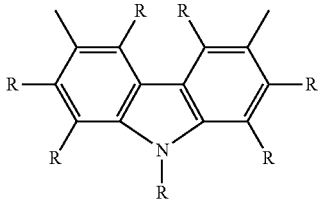
(AA-10)
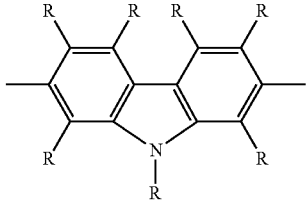
(AA-11)
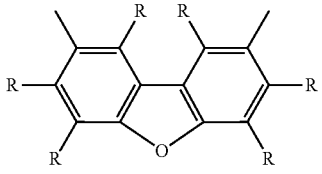
(AA-12)
[Chemical Formula 20]
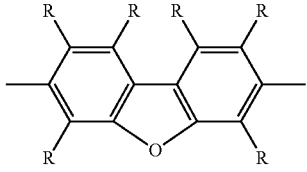
(AA-13)
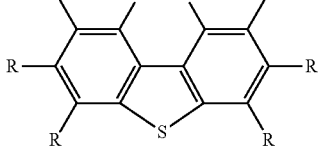
(AA-14)

-continued
(AA-15)
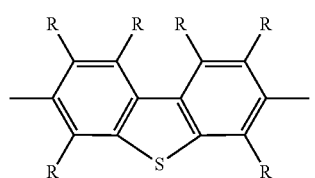
(AA-16)
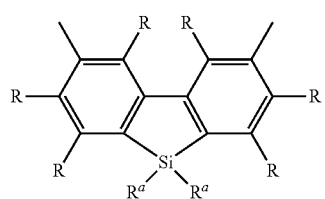
[Chemical Formula 21]
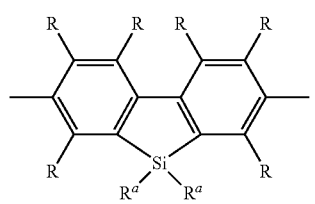
(AA-17)
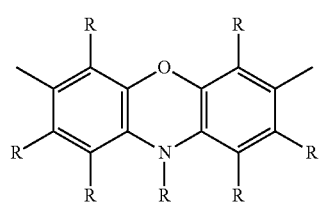
(AA-18)
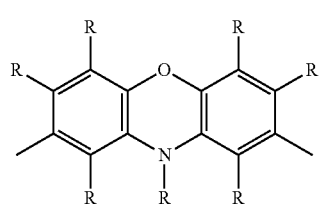
(AA-19)
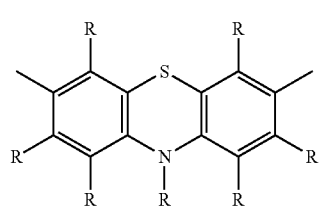
(AA-20)
[Chemical Formula 22]
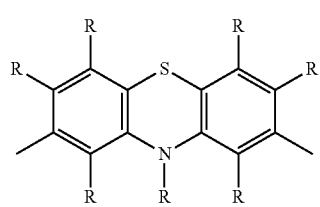
(AA-21)
-continued
(AA-22)
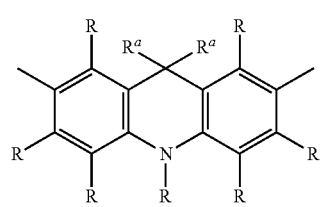
(AA-23)
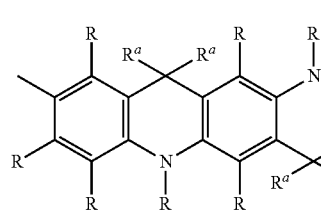
(AA-24)
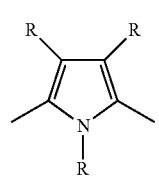
(AA-25)
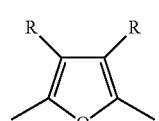
[Chemical Formula 23]
(AA-26)
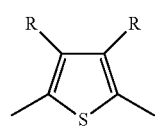
(AA-27)
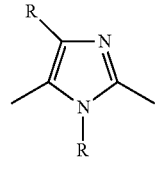
(AA-28)
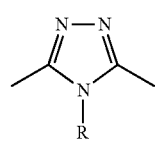
(AA-29)
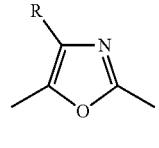
(AA-30)
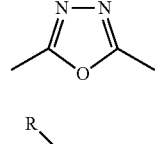
(AA-31)
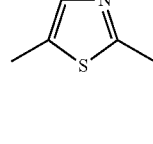

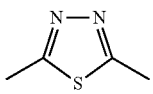
(AA-32)

[Chemical Formula 24]

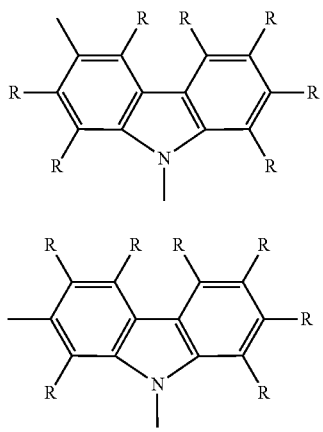
(AA-33)

(AA-34)

[wherein, R and $R^a$ represent the same meaning as described above.]

"Crosslinkable group" is a group capable of forming a new bond by being subjected to heating, ultraviolet irradiation, near ultraviolet irradiation, visible light irradiation, infrared irradiation, a radical reaction and the like, and the crosslinkable group is a group represented by any one of the formulae (B-1) to (B-17). These groups each optionally have a substituent.

[Chemical Formula 25]

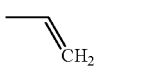
(B-1)

(B-2)

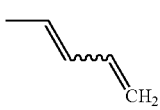
(B-3)

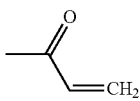
(B-4)

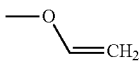
(B-5)

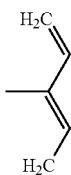
(B-6)

(B-7)

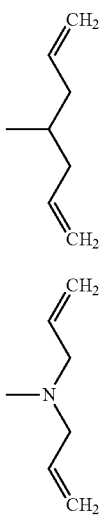
(B-8)

(B-9)

(B-10)

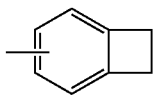
(B-11)

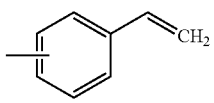
(B-12)

(B-13)

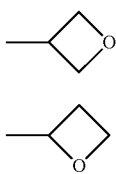
(B-14)

(B-15)

(B-16)

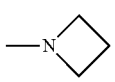
(B-17)

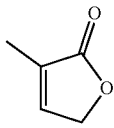

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Compound Represented by Formula (1)>

Next, the compound represented by the formula (1) contained in the composition of the present invention will be illustrated.

The aryl group represented by $R^1$ and $R^2$ is preferably a phenyl group, a naphthyl group, an anthracenyl group, a phenanthrenyl group, a dihydrophenanthrenyl group, a fluorenyl group or a pyrenyl group, more preferably a phenyl group, a naphthyl group or a fluorenyl group, further preferably a phenyl group, and these groups each optionally have a substituent.

The monovalent heterocyclic group represented by $R^1$ and $R^2$ is preferably a pyridyl group, a pyrimidinyl group, a triazinyl group, a quinolinyl group, an isoquinolinyl group, a dibenzofuranyl group, a dibenzothienyl group, a carbazolyl group, an azacarbazolyl group, a diazacarbazolyl group, a phenoxazinyl group or a phenothiazinyl group, more preferably a pyridyl group, a pyrimidinyl group, a triazinyl group, a carbazolyl group, an azacarbazolyl group or a diazacarbazolyl group, further preferably a pyridyl group, a pyrimidinyl group or a triazinyl group, and these groups each optionally have a substituent.

In the substituted amino group represented by $R^1$ and $R^2$, the substituent which the amino group has is preferably an aryl group or a monovalent heterocyclic group, and these groups each optionally further have a substituent. The preferable ranges of the aryl group and the monovalent heterocyclic group as the substituent which the amino group has are the same as the preferable ranges of the aryl group and the monovalent heterocyclic group represented by $R^1$ and $R^2$.

The substituent which $R^1$ and $R^2$ optionally have is preferably an alkyl group, a cycloalkyl group, an aryl group, a monovalent heterocyclic group, an alkoxy group, a cycloalkoxy group, an aryloxy group or a substituted amino group, more preferably an alkyl group, a cycloalkyl group, an aryl group, a monovalent heterocyclic group or a substituted amino group, further preferably an alkyl group, a cycloalkyl group, an aryl group or a monovalent heterocyclic group, particularly preferably an alkyl group, a cycloalkyl group or an aryl group, and these groups each optionally further have a substituent.

$R^1$ and $R^2$ are preferably a group represented by the formula (D-A), a group represented by the formula (D-B) or a group represented by the formula (D-C), because the light emitting device comprising the composition of the present invention is excellent in light emission efficiency.

$m^{DA1}$, $m^{DA2}$, $m^{DA3}$, $m^{DA4}$, $m^{DA5}$, $m^{DA6}$ and $m^{DA7}$ represent usually an integer of 10 or less, preferably an integer of 5 or less, more preferably 0 or 1. It is preferable that $m^{DA1}$, $m^{DA2}$, $m^{DA3}$, $m^{DA4}$, $m^{DA5}$, $m^{DA6}$ and $m^{DA7}$ are the same integer.

$G^{DA}$ is preferably a group represented by the formulae (GDA-11) to (GDA-15), more preferably a group represented by the formulae (GDA-11) to (GDA-14), further preferably a group represented by the formula (GDA-11).

[Chemical Formula 26]

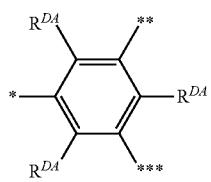
(GDA-11)

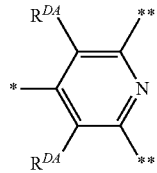
(GDA-12)

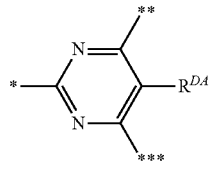
(GDA-13)

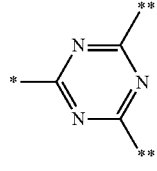
(GDA-14)

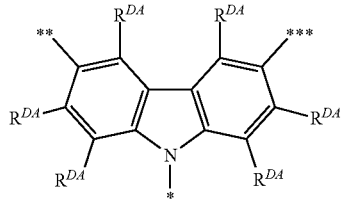
(GDA-15)

[wherein,

* represents a bond to $Ar^{DA1}$ in the formula (D-A), $Ar^{DA1}$ in the formula (D-B), $Ar^{DA2}$ in the formula (D-B) or $Ar^{DA3}$ in the formula (D-B).

** represents a bond to $Ar^{DA2}$ in the formula (D-A), $Ar^{DA2}$ in the formula (D-B), $Ar^{DA4}$ in the formula (D-B) or $Ar^{DA6}$ in the formula (D-B).

*** represents a bond to $Ar^{DA3}$ in the formula (D-A), $Ar^{DA3}$ in the formula (D-B), $Ar^{DA5}$ in the formula (D-B) or $Ar^{DA7}$ in the formula (D-B).

$R^{DA}$ represents a hydrogen atom, an alkyl group, a cycloalkyl group, an alkoxy group, a cycloalkoxy group, an aryl group or a monovalent heterocyclic group, and these groups each optionally further have a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or a cycloalkyl group, and these groups each optionally have a substituent.

$Ar^{DA1}$, $Ar^{DA2}$, $Ar^{DA3}$, $Ar^{DA4}$, $Ar^{DA5}$, $Ar^{DA6}$ and $Ar^{DA7}$ represent preferably a phenylene group, a fluorenediyl group or a carbazolediyl group, more preferably a group represented by the formula (A-1) to the formula (A-3), the formula (A-8), the formula (A-9), the formula (AA-10), the formula (AA-11), the formula (AA-33) or the formula (AA-34), further preferably a group represented by the formula (ArDA-1) to the formula (ArDA-5), particularly preferably a group represented by the formula (ArDA-1) to the formula (ArDA-3), especially preferably a group represented by the formula (ArDA-1), and these groups each optionally have a substituent.

[Chemical Formula 27]

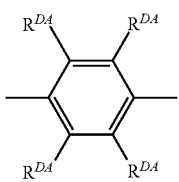 (ArDA-1)

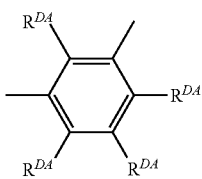 (ArDA-2)

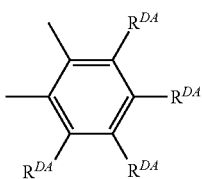 (ArDA-3)

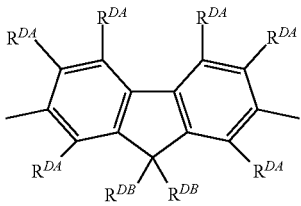 (ArDA-4)

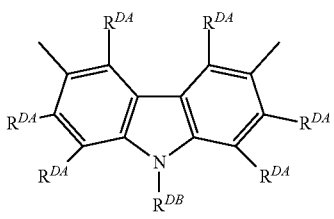 (ArDA-5)

[wherein, $R^{DA}$ represents the same meaning as described above.

$R^{DB}$ represents a hydrogen atom, an alkyl group, a cycloalkyl group, an aryl group or a monovalent heterocyclic group, and these groups each optionally have a substituent. When a plurality of $R^{DB}$ are present, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group, and these groups each optionally have a substituent.

$T^{DA}$ is preferably a group represented by the formula (TDA-1) to the formula (TDA-3), more preferably a group represented by the formula (TDA-1).

[Chemical Formula 28]

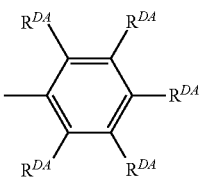 (TDA-1)

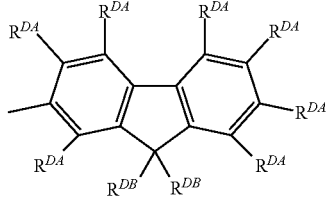 (TDA-2)

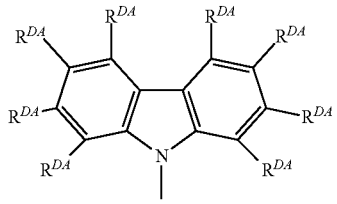 (TDA-3)

[wherein, $R^{DA}$ and $R^{DB}$ represent the same meaning as described above.]

The group represented by the formula (D-A) is preferably a group represented by the formula (D-A1) to the formula (D-A4), more preferably a group represented by the formulae (D-A1) to the formula (D-A3), further preferably a group represented by the formula (D-A1).

The group represented by the formula (D-B) is preferably a group represented by the formula (D-B1) to the formula (D-B3), more preferably a group represented by the formula (D-B1).

The group represented by the formula (D-C) is preferably a group represented by the formula (D-C1) to the formula (D-C4), more preferably a group represented by the formula (D-C1) to the formula (D-C3), further preferably a group represented by the formula (D-C1) or the formula (D-C2), particularly preferably a group represented by the formula (D-C1).

np1 is preferably 0 or 1, more preferably 1. np2 is preferably 0 or 1, more preferably 0. np3 is preferably 0. np4 is preferably 0 to 2. np5 is preferably 0 to 2, more preferably 0.

$R^{p1}$, $R^{p2}$, $R^{p3}$, $R^{p4}$ and $R^{p5}$ are preferably an alkyl group or a cycloalkyl group.

The group represented by the formula (D-A) includes, for example, groups represented by the formulae (D-A-1) to (D-A-12).
[Chemical Formula 29]
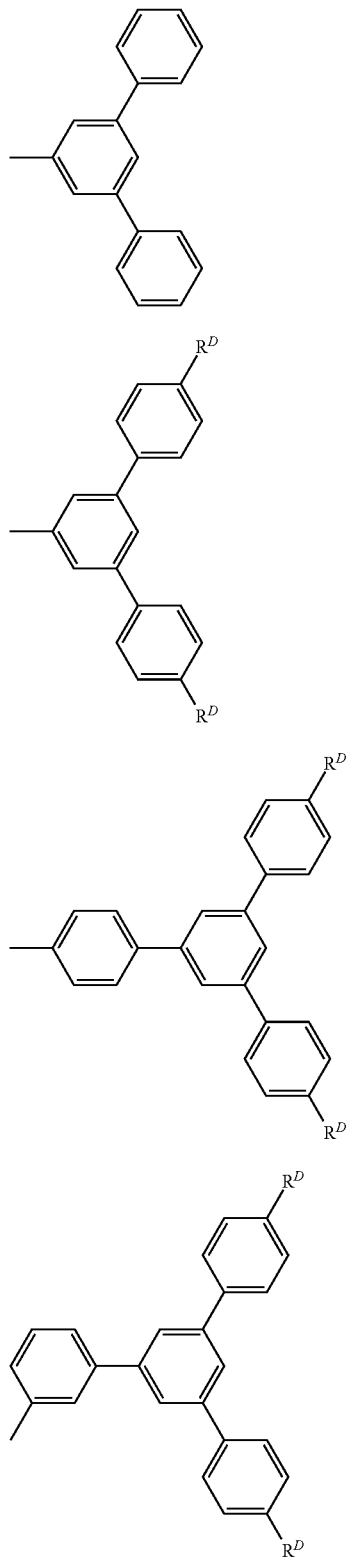
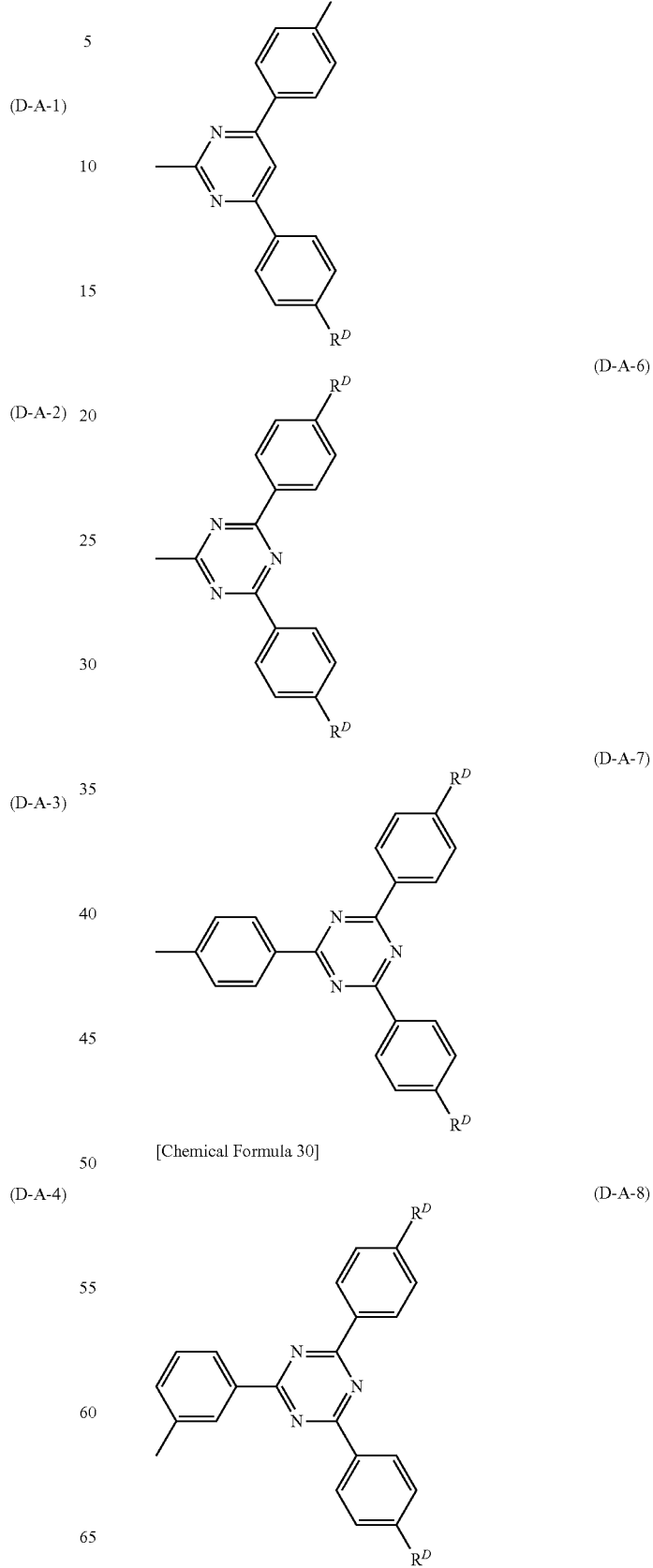
[Chemical Formula 30]

(D-A-9)

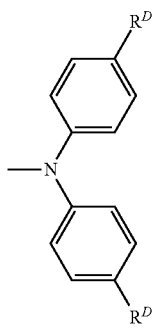

(D-A-12)

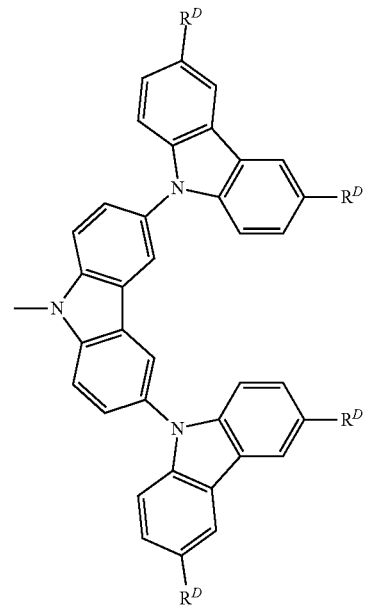

(D-A-10)

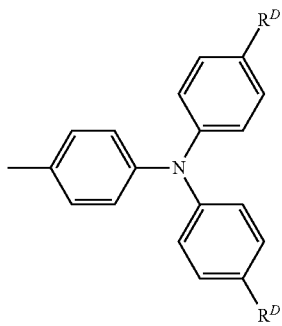

[wherein, $R^D$ represents a methyl group, an ethyl group, an isopropyl group, a tert-butyl group, a hexyl group, a 2-ethylhexyl group, a tert-octyl group, a cyclohexyl group, a methoxy group, a 2-ethylhexyloxy group or a cyclohexyloxy group. When a plurality of $R^D$ are present, they may be the same or different.]

The group represented by the formula (D-B) includes, for example, groups represented by the formulae (D-B-1) to (D-B-4).

[Chemical Formula 31]

(D-B-1)

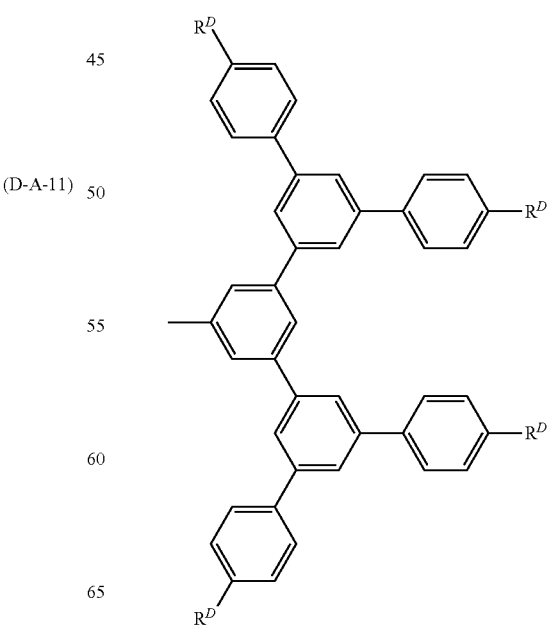

(D-A-11)

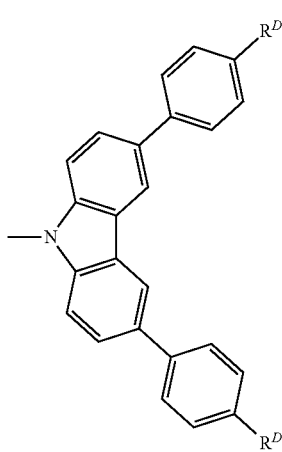

(D-B-2)
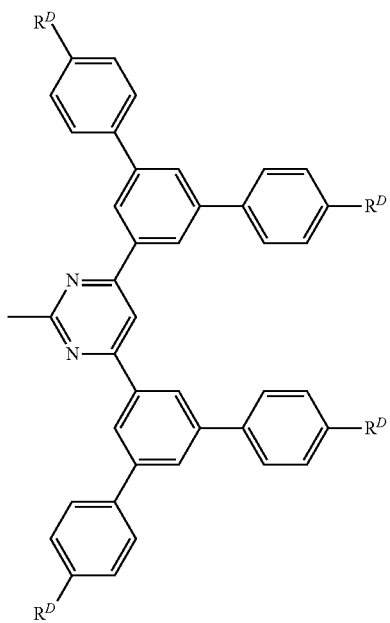
(D-B-4)
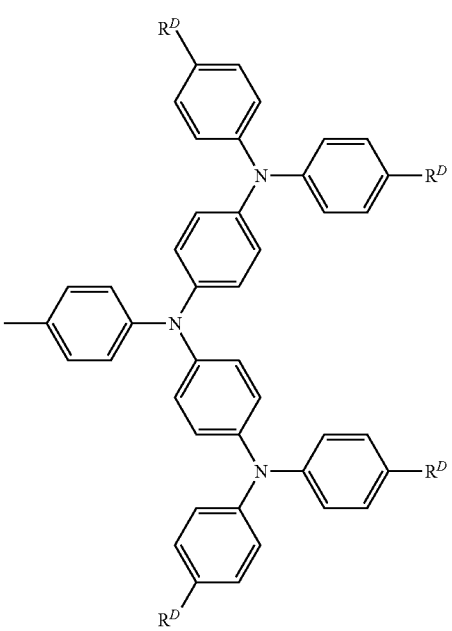
[wherein, $R^D$ represents the same meaning as described above.]
The group represented by the formula (D-C) includes, for example, groups represented by the formulae (D-C-1) to (D-C-13).
[Chemical Formula 32]
(D-C-1)
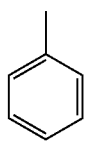
(D-C-2)
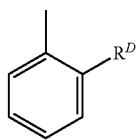
(D-C-3)
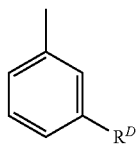
(D-C-4)
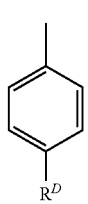
(D-B-3)
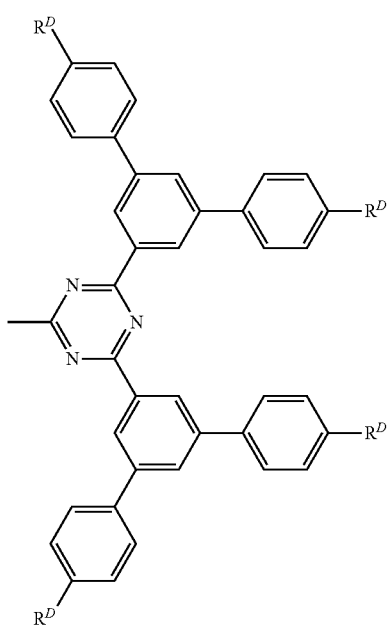

(D-C-5) 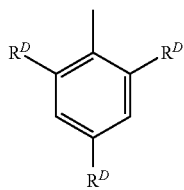

(D-C-6) 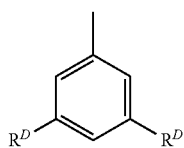

(D-C-7) 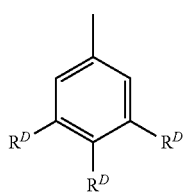

(D-C-8) 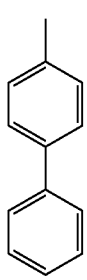

(D-C-9) 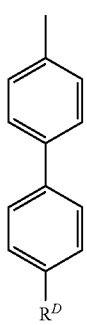

(D-C-10) 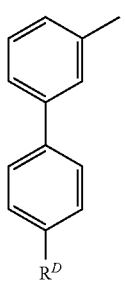

(D-C-11) 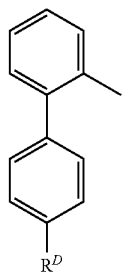

(D-C-12) 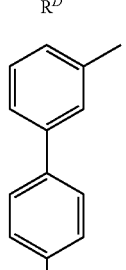

(D-C-13) 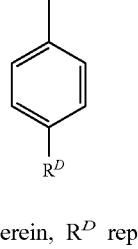

[wherein, $R^D$ represents the same meaning as described above.]

$R^D$ is preferably a methyl group, an ethyl group, an isopropyl group, a tert-butyl group, a hexyl group, a 2-ethylhexyl group or a tert-octyl group, more preferably a tert-butyl group.

$R^1$ and $R^2$ is preferably a substituted amino group or an aryl group optionally having a substituent, more preferably an aryl group optionally having a substituent, further preferably a group represented by the formula (D-A1), the formula (D-B1) or the formula (D-C1) to the formula (D-C4), particularly preferably a group represented by the formula (D-A1), the formula (D-B1) or the formula (D-C1) to the formula (D-C3), especially preferably a group represented by the formula (D-A1), the formula (D-B1) or the formula (D-C1), especially more preferably a group represented by the formula (D-B1) or the formula (D-C1), because the light emitting device comprising the composition of the present invention is more excellent in light emission efficiency.

$n^1$ is preferably an integer of 1 to 10, more preferably an integer of 1 to 7.

The arylene group represented by $Ar^1$ is more preferably a group represented by the formula (A-1), the formula (A-2), the formula (A-6) to the formula (A-10), the formula (A-19) or the formula (A-20), further preferably a group represented by the formula (A-1), the formula (A-2), the formula (A-7), the formula (A-9) or the formula (A-19), and these groups each optionally have a substituent. At least one $Ar^1$ is a group represented by the formula (1-A).

The divalent heterocyclic group represented by $Ar^1$ is more preferably a group represented by the formula (AA-1) to the formula (AA-4), the formula (AA-10) to the formula (AA-15), the formula (AA-18) to the formula (AA-21), the formula (AA-33) or the formula (AA-34), further preferably a group represented by the formula (AA-4), the formula (AA-10), the formula (AA-12), the formula (AA-14), the formula (AA-18), the formula (AA-20) or the formula (AA-33), particularly preferably a group represented by the formula (AA-4), the formula (AA-10), the formula (AA-12), the formula (AA-14) or the formula (AA-33), and these groups each optionally have a substituent. At least one $Ar^1$ is a group represented by the formula (1-A)

The preferable range of the substituent which the group represented by $Ar^1$ optionally has is the same as the preferable range of the substituent which $R^1$ and $R^2$ optionally have.

When two or more $Ar^1$ are present and when the two or more $Ar^1$ are groups represented by the formula (1-A), they may be the same or different.

$Ar^1$ is preferably a group represented by the formula (i-A), because the light emitting device comprising the composition of the present invention is excellent in light emission efficiency. That is, it is preferable that all of $n^1$ groups $Ar^1$ are groups represented by the formula (1-A)

[Group Represented by the Formula (1-A)]

Next, the group represented by the formula (1-A) will be illustrated.

It is preferable that one of $R^{2A}$ and $R^{3A}$ is a connecting bond, and it is more preferable that $R^{2A}$ is a connecting bond.

It is preferable that one of $R^{6A}$ and $R^{7A}$ is a connecting bond, and it is more preferable that $R^{7A}$ is a connecting bond.

It is preferable that one of $R^{2A}$ and $R^{3A}$ is a connecting bond and one of $R^{6A}$ and $R^{7A}$ is a connecting bond, and it is more preferable that $R^{2A}$ is a connecting bond and $R^{7A}$ is a connecting bond.

When $R^{1A}$ to $R^{8A}$ are other than a connecting bond, $R^{1A}$ to $R^{8A}$ are preferably a hydrogen atom, an alkyl group, a cycloalkyl group, an alkoxy group, an aryl group or a monovalent heterocyclic group, more preferably a hydrogen atom, an alkyl group, a cycloalkyl group or an aryl group, further preferably a hydrogen atom or an alkyl group, particularly preferably a hydrogen atom, and these groups each optionally have a substituent.

The preferable ranges of the aryl group, the monovalent heterocyclic group and the substituted amino group represented by $R^{1A}$ to $R^{8A}$ are the same as the preferable ranges of the aryl group, the monovalent heterocyclic group and the substituted amino group represented by $R^1$ and $R^2$.

The preferable range of the substituent which R to R optionally have is the same as the preferable range of the substituent which $R^1$ and $R^2$ optionally have.

It is preferable that $R^{1A}$ and $R^{2A}$, $R^{2A}$ and $R^{3A}$, $R^{3A}$ and $R^{4A}$, $R^{4A}$ and $R^{5A}$, $R^{5A}$ and $R^{6A}$, $R^{6A}$ and $R^{7A}$, and $R^{7A}$ and $R^{8A}$ each are not combined together to form a ring together with the carbon atoms to which they are attached $R^{91A}$ is preferably an alkyl group optionally having a substituent or a cycloalkyl group optionally having a substituent, more preferably an alkyl group optionally having a substituent, further preferably an alkyl group having no substituent, because the light emitting device comprising the composition of the present invention is more excellent in light emission efficiency.

The preferable ranges of the aryl group and the monovalent heterocyclic group represented by $R^{92A}$ are the same as the preferable ranges of the aryl group and the monovalent heterocyclic group represented by $R^1$ and $R^2$.

The aryl group and the monovalent heterocyclic group represented by $R^{92A}$ are preferably groups represented by the formula (D-A) to the formula (D-C). When $R^{92A}$ is a group represented by the formula (D-A) or the formula (D-B) and $m^{DA1}$ is 0, $G^{DA}$ bonded to $Ar^{DA2}$ and $Ar^{DA3}$ in the formulae (D-A) and (D-B) is an aromatic hydrocarbon group or a heterocyclic group, and these groups each optionally have a substituent.

$R^{92A}$ is preferably an aryl group optionally having a substituent, more preferably a group represented by the formula (D-A1), the formula (D-B1) or the formula (D-C1) to the formula (D-C4), further preferably a group represented by the formula (D-A1), the formula (D-B1) or the formula (D-C1) to the formula (D-C3), particularly preferably a group represented by the formula (D-A1), the formula (D-B1) or the formula (D-C1), especially preferably a group represented by the formula (D-C1), because the light emitting device comprising the composition of the present invention is more excellent in light emission efficiency.

The preferable range of the substituent which $R^{91A}$ and $R^{92A}$ optionally have is the same as the preferable range of the substituent which $R^1$ and $R^2$ optionally have.

The group represented by the formula (1-A) is preferably a group represented by the formula (1-A-A1) or the formula (1-A-A2), more preferably a group represented by the formula (1-A-A1), because the driving voltage of the light emitting device comprising the composition of the present invention is lower.

[Chemical Formula 33]

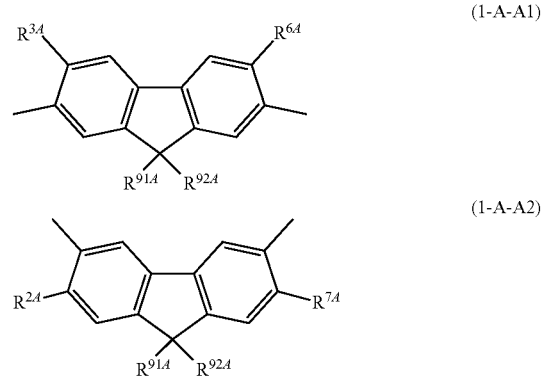

[wherein, $R^{2A}$, $R^{3A}$, $R^{6A}$, $R^{7A}$, $R^{91A}$ and $R^{92A}$ represent the same meaning as described above.]

The group represented by the formula (1-A) includes, for example, groups represented by the formula (1-A-1) to the formula (1-A-19), and is preferably a group represented by the formula (1-A-1) to the formula (1-A-16), more preferably a group represented by the formula (1-A-1) to the formula (1-A-11), further preferably a group represented by the formula (1-A-1) to the formula (1-A-8).

TABLE 1

| Formula | $R^{1A}$ | $R^{2A}$ | $R^{3A}$ | $R^{4A}$ | $R^{5A}$ | $R^{6A}$ | $R^{7A}$ | $R^{8A}$ | $R^{91A}$ | $R^{92A}$ |
|---|---|---|---|---|---|---|---|---|---|---|
| (1-A-1) | H | connecting bond | H | H | H | H | connecting bond | H | Me | formula (D-C-6) |
| (1-A-2) | H | connecting bond | H | H | H | H | connecting bond | H | $C_8H_{17}$ | formula (D-C-3) |
| (1-A-3) | H | connecting bond | H | H | H | H | connecting bond | H | i-Pr | formula (D-C-1) |
| (1-A-4) | H | connecting bond | H | H | H | H | connecting bond | H | t-Bu | formula (D-C-1) |
| (1-A-5) | H | connecting bond | H | H | H | H | connecting bond | H | Me | formula (D-C-10) |
| (1-A-6) | H | connecting bond | H | H | H | H | connecting bond | H | Me | formula (D-A-2) |
| (1-A-7) | H | connecting bond | H | H | H | H | connecting bond | H | Et | formula (D-A-4) |
| (1-A-8) | H | connecting bond | H | H | H | H | connecting bond | H | Me | formula (D-B-1) |
| (1-A-9) | H | connecting bond | Me | H | H | Me | connecting bond | H | Me | formula (D-C-4) |
| (1-A-10) | H | connecting bond | formula (D-C-1) | H | H | formula (D-C-1) | connecting bond | H | Me | formula (D-C-4) |
| (1-A-11) | Me | connecting bond | H | Me | Me | H | connecting bond | Me | Me | formula (D-C-6) |

TABLE 2

| Formula | $R^{1A}$ | $R^{2A}$ | $R^{3A}$ | $R^{4A}$ | $R^{5A}$ | $R^{6A}$ | $R^{7A}$ | $R^{8A}$ | $R^{91A}$ | $R^{92A}$ |
|---|---|---|---|---|---|---|---|---|---|---|
| (1-A-12) | H | H | connecting bond | H | H | connecting bond | H | H | Me | formula (D-C-4) |
| (1-A-13) | H | H | connecting bond | H | H | connecting bond | H | H | Me | formula (D-C-9) |
| (1-A-14) | H | H | connecting bond | H | H | connecting bond | H | H | Me | formula (D-A-1) |
| (1-A-15) | H | Me | connecting bond | H | H | connecting bond | Me | H | Me | formula (D-C-3) |
| (1-A-16) | Me | H | connecting bond | Me | Me | connecting bond | H | Me | Me | formula (D-C-3) |
| (1-A-17) | connecting bond | H | H | H | H | H | H | H | connecting bond | formula (D-C-6) |
| (1-A-18) | H | H | H | connecting bond | connecting bond | H | H | H | Me | formula (D-C-6) |
| (1-A-19) | connecting bond | H | H | H | connecting bond | H | H | H | Me | formula (D-C-6) |

The compound represented by the formula (1) includes, for example, compounds represented by the formula (1-1) to the formula (1-19), and is preferably a compound represented by the formula (1-1) to the formula (1-15), more preferably a compound represented by the formula (1-1) to the formula (1-8), further preferably a compound represented by the formula (1-1) to the formula (1-6).

TABLE 3

| Formula | $R^1$ | $-[Ar^1]_{n^1}-$ | $R^2$ |
|---|---|---|---|
| (1-1) | formula (D-B-1) | -formula (1-A-1)- | formula (D-B-1) |
| (1-2) | formula (D-A-1) | -[-formula (1-A-5)-]$_2$- | formula (D-A-1) |
| (1-3) | formula (D-C-4) | -[-formula (1-A-6)-]$_3$- | formula (D-C-4) |
| (1-4) | formula (D-C-7) | -[-formula (1-A-4)-]$_5$- | formula (D-C-7) |
| (1-5) | formula (D-C-1) | -[-formula (1-A-2)-]$_7$- | formula (D-C-1) |
| (1-6) | formula (D-C-10) | -[-formula (1-A-1)-]$_{10}$- | formula (D-C-10) |
| (1-7) | formula (D-A-2) | -formula (1-A-2)-formula (1-A-1)-formula (1-A-2)- | formula (D-A-2) |

TABLE 3-continued

| Formula | $R^1$ | $-[Ar^1]_{n^1}-$ | $R^2$ |
|---|---|---|---|
| (1-8) | formula (D-A-4) | -formula (1-A-2)-formula (1-A-1)-formula (1-A-2)-formula (1-A-1)-formula (1-A-2) | formula (D-A-4) |
| (1-9) | formula (D-A-9) | -formula (1-A-2) — ⟨ring⟩ — formula (1-A-9) — ⟨ring⟩ — formula (1-A-2) | formula (D-C-9) |
| (1-10) | formula (D-A-4) | -formula (1-A-10) ⟨fluorene with two p-tolyl groups⟩ formula (1-A-10) ------ | formula (D-A-4) |
| (1-11) | formula (D-A-11) | -formula (1-A-12)- | formula (D-A-11) |
| (1-12) | formula (D-A-5) | -formula (1-A-4)- | formula (D-A-8) |
| (1-13) | formula (D-A-6) | -formula (1-A-3)- | formula (D-B-3) |
| (1-14) | formula (D-A-10) | -formula (1-A-1)- | formula (D-B-4) |
| (1-15) | formula (D-C-1) | -formula (1-A-17)-formula (1-A-18)-formula (1-A-19)- | formula (D-C-1) |
| (1-16) | formula (D-A-9) | -formula (1-A-1)- | formula (D-A-9) |
| (1-17) | formula (D-A-5) | -formula (1-A-1)- | formula (D-A-5) |
| (1-18) | formula (D-B-1) | -formula (1-A-1)-formula (AA-18)-formula-(1-A-1)- | formula (D-B-1) |
| (1-19) | formula (D-A-6) | ⟨fluorene with methyl and phenyl substituents⟩ -formula (AA-33) ------ | formula (D-C-1) |

In the composition of the present invention, the compound represented by the formula (1) may be used singly or two or more of the compounds represented by the formula (1) may be used in combination.

<Production Method of Compound Represented by Formula (1)>

Next, the production method of the compound represented by the formula (1) will be illustrated.

The compound represented by the formula (1) can be synthesized by using known coupling reactions and the like using a transition metal catalyst such as the Suzuki reaction, the Buchwald reaction, the Stille reaction, the Negishi reaction and the Kumada reaction.

[Production Method of Compound (1')]

First, the production method of the compound represented by the formula (1) in which $n^1$ is 2 or more (in the present specification, referred to as "the compound (1')") will be illustrated.

For example, the compound (1') can be synthesized by reacting a compound represented by the formula (1'-1), a compound represented by the formula (1'-2), a compound represented by the formula (1'-3) and a compound represented by the formula (1'-4) by using a known coupling reaction and the like.

[Chemical Formula 34]

$$Z^{C1}-Ar^1-Z^{C2} \qquad (1'\text{-}1)$$

$$Z^{C3}-Ar^1-Z^{C4} \qquad (1'\text{-}2)$$

$$R^1-Z^{C5} \qquad (1'\text{-}3)$$

$$R^2-Z^{C6} \qquad (1'\text{-}4)$$

[wherein, $Ar^1$, $R^1$ and $R^2$ represent the same meaning as described above. The plurality of $Ar^1$ may be the same or different.

$Z^{C1}$ to $Z^{C6}$ each independently represent a group selected from the group consisting of Group A of substituent and Group B of substituent.]

<Group A of Substituent>

A chlorine atom, a bromine atom, an iodine atom and a group represented by $-O-S(=O)_2R^{C1}$ (wherein, $R^{C1}$ represents an alkyl group, a cycloalkyl group or an aryl group, and these groups each optionally have a substituent).

<Group B of Substituent>

A group represented by $-B(OR^{C2})_2$ (wherein, $R^{C2}$ represents a hydrogen atom, an alkyl group, a cycloalkyl group or an aryl group, and these groups each optionally have a substituent. The plurality of $R^{C2}$ may be the same or different and may be combined together to form a cyclic structure together with the oxygen atoms to which they are attached);

a group represented by —BF$_3$Q' (wherein, Q' represents Li, Na, K, Rb or Cs);

a group represented by —MgY' (wherein, Y' represents a chlorine atom, a bromine atom or an iodine atom);

a group represented by —ZnY'' (wherein, Y'' represents a chlorine atom, a bromine atom or an iodine atom); and a group represented by —Sn(R$^{C3}$)$_3$ (wherein, R$^{C3}$ represents a hydrogen atom, an alkyl group, a cycloalkyl group or an aryl group, and these groups each optionally have a substituent. The plurality of R$^{C3}$ may be the same or different and may be combined together to form a cyclic structure together with the tin atom to which they are attached.).

As the group represented by —B(OR$^{C2}$)$_2$, groups represented by the following formulae (W-1) to (W-10) are exemplified.

[Chemical Formula 35]

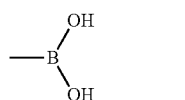
(W-1)

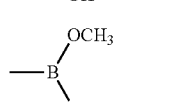
(W-2)

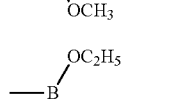
(W-3)

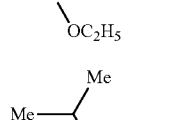
(W-4)

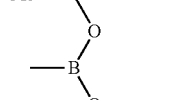
(W-5)

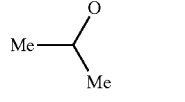
(W-6)

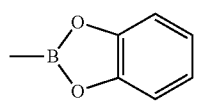
(W-7)

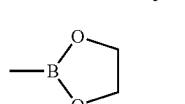
(W-8)

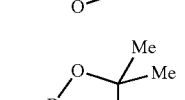
(W-9)

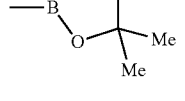
(W-10)

[Synthesis Methods 1,2]

For example, a compound represented by the formula (1'-5) or a compound represented by the formula (1'-6) can be synthesized by coupling-reacting the compound represented by the formula (1'-1) and the compound represented by the formula (1'-2) once or two or more-times.

[Chemical Formula 36]

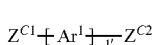
(1'-5)

(1'-6)

[wherein, Ar$^1$, Z$^{C1}$, Z$^{C2}$ and Z$^{C3}$ represent the same meaning as described above. n1' represents an integer of 2 to 15.]

For example, a compound represented by the formula (1'-7) can be synthesized by coupling-reacting the compound represented by the formula (1'-5) and the compound represented by the formula (1'-3 T hereafter, a compound (1') can be synthesized by coupling-reacting the compound represented by the formula (1'-7) and the compound represented by the formula (1'-4) (hereinafter, referred to as "synthesis method 1")

[Chemical Formula 37]

(1'-7)

[wherein, Ar$^1$, Z$^{C2}$, R$^1$ and n1' represent the same meaning as described above.]

For example, a compound represented by the formula (1'-8) can be synthesized by coupling-reacting the compound represented by the formula (1'-6) and the compound represented by the formula (1'-3). Thereafter, the compound (1') can be synthesized by coupling-reacting the compound represented by the formula (1'-8) and the compound represented by the formula (1'-4) (hereinafter, referred to as "synthesis method 2")

[Chemical Formula 38]

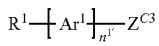
(1'-8)

[wherein, Ar$^1$, Z$^{C3}$, R$^1$ and n1' represent the same meaning as described above.]

In the synthesis method 1, for example, when Z$^{C1}$ and Z$^{C2}$ are groups selected from Group A of substituent, groups selected from Group B of substituent are selected as $Z^{C3}$, $Z^{C4}$, $Z^{C5}$ and $Z^{C6}$. For example, when $Z^{C1}$ and $Z^{C2}$ are groups selected from Group B of substituent, groups selected from Group A of substituent are selected as $Z^{C3}$, $Z^{C4}$, $Z^{C5}$ and $Z^{C6}$.

In the synthesis method 2, for example, when $Z^{C1}$, $Z^{C2}$ and $Z^{C6}$ are groups selected from Group A of substituent, groups selected from Group B of substituent are selected as $Z^{C3}$, $Z^{C4}$ and $Z^{C5}$ For example, when $Z^{C1}$, $Z^{C2}$ and $Z^{C6}$ are groups selected from Group B of substituent, groups selected from Group A of substituent are selected as $Z^{C3}$, $Z^{C4}$ and $Z^{C5}$.

[Synthesis Method 3 (Production Method of Compound (1″))]

Next, the production method of the compound represented by the formula (1) in which $n^1$ is 1 (in the present specification, referred to as "the compound (1″)".) will be illustrated.

For example, the compound (1″) can be synthesized by reacting the compound represented by the formula (1'-1), the compound represented by the formula (1'-2) and the compound represented by the formula (1'-3) by using a known coupling reaction and the like.

For example, a compound represented by the formula (1'-9) can be synthesized by coupling-reacting the compound represented by the formula (1'-1) and the compound represented by the formula (1'-3). Thereafter, the compound (1″) can be synthesized by coupling-reacting the compound represented by the formula (1'-9) and the compound represented by the formula (1'-4) (hereinafter, referred to as "synthesis method 3".).

[Chemical Formula 39]

$$R^1\text{—}Ar^1\text{—}Z^{C2} \quad (1'\text{-}9)$$

[wherein, $Ar^1$, $Z^{C2}$ and $R^1$ represent the same meaning as described above.]

In the synthesis method 3, for example, when $Z^{C1}$ and $Z^{C2}$ are groups selected from Group A of substituent, groups selected from. Group B of substituent are selected as $Z^{C3}$ and $Z^{C4}$. For example, when $Z^{C1}$ and $Z^{C2}$ are groups selected from Group B of substituent, groups selected from Group A of substituent are selected as $Z^{C3}$ and $Z^{C4}$.

[Common Explanation of Production Method of Compound (1') and Compound (1″)]

The group selected from Group A of substituent is preferably a bromine atom, an iodine atom or a trifluoromethanesulfonyloxy group because the coupling reaction progresses easily.

The group selected from Group B of substituent is preferably a group represented by —$B(OR^{C2})_2$, more preferably a group represented by the formula (W-7).

The coupling reaction is usually conducted in a solvent. The solvent includes, for example, alcohol solvents such as methanol, ethanol, propanol, ethylene glycol, glycerin, 2-methoxyethanol and 2-ethoxyethanol; ether solvents such as diethyl ether, tetrahydrofuran (tHF), dioxane, cyclopentyl methyl ether and diglyme; halogen-based solvents such as methylene chloride and chloroform; nitrile solvents such as acetonitrile and benzonitrile; hydrocarbon solvents such as hexane, decalin, toluene, xylene and mesitylene; amide solvents such as N,N-dimethylformamide and N,N-dimethylacetamide; acetone, dimethyl sulfoxide and water.

In the coupling reaction, the reaction time is usually 30 minutes to 150 hours and the reaction temperature is usually from the melting point to the boiling point of a solvent present in the reaction system.

In the coupling reaction, a catalyst such as a palladium catalyst may be used for promoting the reaction. The palladium catalyst includes, for example, palladium acetate, bis(triphenylphosphine)palladium(II) dichloride, tetrakis (triphenylphosphine)palladium(0) [1,1'-bis(diphenyl phosphino) ferrocene]dichloropalladium(II) and tris(dibenzylideneacetone)dipalladium(0)

The palladium catalyst may be used together with a phosphorus compound such as triphenylphosphine, tri (o-tolyl)phosphine, tri (tert-butyl)phosphine, tricyclohexylphosphine and 1,1'-bis(diphenylphosphino)ferrocene.

In the coupling reaction, a palladium catalyst and a base may be used in combination, when necessary.

When the coupling reaction is conducted twice or more, they may be reacted under the same condition or may be reacted under different conditions.

The compounds, the catalysts and the solvents used in each reaction explained in <Production method of compound represented by formula (1)> may each be used singly or two or more of them may be used together.

The compounds represented by the formula (1'-1) to the formula (1'-4) are available from Aldrich, Luminescence Technology Corp. and the like.

The compounds can be produced also by known methods described in documents such as International Publication WO2002/045184, JP-A No. 2012-144722, International Publication WO2002/067343 and International Publication WO2004/039912.

<Phosphorescent Compound>

Next, the phosphorescent compound contained in the composition of the present invention will be illustrated.

"The phosphorescent compound" usually denotes a compound which shows a phosphorescent property at room temperature (25° C.), and is preferably a metal complex which shows light emission from the triplet excited state at room temperature. This metal complex which shows light emission from the triplet excited state has a central metal atom and a ligand.

The central metal atom includes, for example, metal atoms having an atomic number of 40 or more, having spin-orbital interaction in the complex, and capable of causing intersystem crossing between the singlet state and the triplet state. The metal atom includes, for example, a ruthenium atom, a rhodium atom, a palladium atom, an iridium atom and a platinum atom, and it is preferably an iridium atom or a platinum atom because the light emitting device comprising the composition of the present invention is excellent in light emission efficiency.

The ligand includes, for example, neutral or anionic monodentate ligands or neutral or anionic polydentate ligands forming at least one bond selected from the group consisting of the coordinate bond and the covalent bond between the central metal atom. The bond between the central metal atom and the ligand includes, for example, a metal-nitrogen bond, a metal-carbon bond, a metal-oxygen bond, a metal-phosphorus bond, a metal-sulfur bond and a metal-halogen bond. The polydentate ligand usually means a bidentate or more and hexadentate or less ligand.

[Metal Complex Represented by Formula (M)]

The phosphorescent compound is preferably a metal complex represented by the formula (M).

$M^1$ is preferably an iridium atom, because the light emitting device comprising the composition of the present invention is more excellent in light emission efficiency.

When M¹ is an iridium atom, $n^{M1}$ is preferably 2 or 3, more preferably 3.

When M¹ is a platinum atom, $n^{M1}$ is preferably 2.

$E^1$ and $E^2$ preferably represent a carbon atom.

The ring $R^{M1}$ is preferably a 5- or 6-membered aromatic heterocyclic ring having 1 to 4 nitrogen atoms as the constituent atom, more preferably a pyridine ring, a diazabenzene ring, a triazine ring, a quinoline ring, an isoquinoline ring, a diazole ring or a triazole ring, further preferably a pyridine ring, a pyrimidine ring, a quinoline ring, an isoquinoline ring, an imidazole ring or a triazole ring, and these rings each optionally have a substituent.

The ring $R^{M2}$ is preferably a 5- or 6-membered aromatic hydrocarbon ring or a 5- or 6-membered aromatic heterocyclic ring, more preferably a benzene ring, a naphthalene ring, a fluorene ring, a phenanthrene ring, a pyridine ring, a diazabenzene ring, a triazine ring, a pyrrole ring, a furan ring or a thiophene ring, further preferably a benzene ring, a naphthalene ring, a fluorene ring, a phenanthrene ring, a pyridine ring or a diazabenzene ring, particularly preferably a benzene ring, a pyridine ring or a pyrimidine ring, especially preferably a benzene ring, and these rings each optionally have a substituent.

The substituent which the ring $R^{M1}$ and the ring $R^{M2}$ optionally have is preferably an alkyl group, a cycloalkyl group, an aryl group, a monovalent heterocyclic group, an alkoxy group, a cycloalkoxy group, an aryloxy group or a substituted amino group, more preferably an alkyl group, a cycloalkyl group, an aryl group, a monovalent heterocyclic group or a substituted amino group, further preferably an alkyl group, a cycloalkyl group, an aryl group or a monovalent heterocyclic group, particularly preferably an alkyl group, a cycloalkyl group or an aryl group, and these groups each optionally further have a substituent.

The substituent which the ring $R^{M1}$ optionally has and the substituent which the ring $R^{M2}$ optionally has may be combined together to form a ring together with the atoms to which they are attached, but it is preferable that they do not form a ring.

The aryl group, the monovalent heterocyclic group or the substituted amino group as the substituent which the ring $R^{M1}$ and the ring $R^{M2}$ optionally have is preferably a group represented by the formula (D-A), the formula (D-B) or the formula (D-C), because the light emitting device of the present invention is more excellent in light emission efficiency.

It is preferable that at least one ring selected from the group consisting of the ring $R^{M1}$ and the ring $R^{M2}$ has a substituent, because excellent solubility is obtained.

The substituent which at least one ring selected from the group consisting of the ring $R^{M1}$ and the ring $R^{M2}$ has is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1), the formula (D-B3) or the formula (D-C1) to the formula (D-C3), especially preferably an alkyl group or a group represented by the formula (D-A1), the formula (D-B1), the formula (D-C1) or the formula (D-C2), especially more preferably a group represented by the formula (D-A1), the formula (D-B1), the formula (D-C1) or the formula (D-C2), because synthesis of the metal complex represented by the formula (M) is easy, and these groups each optionally have a substituent.

The anionic bidentate ligand represented by -$A^{D1}$---$A^{D2}$- includes, for example, ligands represented by the following formulae.

[Chemical Formula 40]

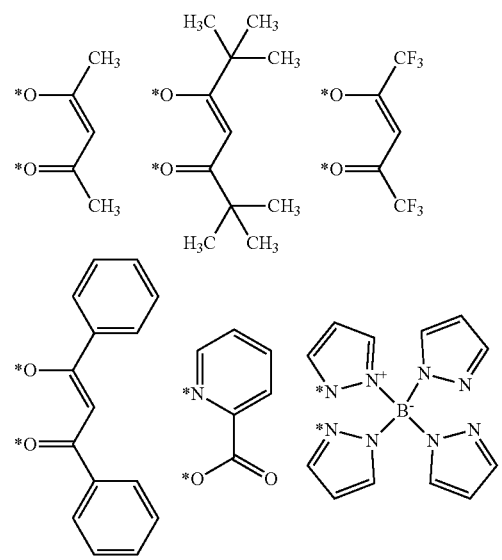

[wherein, * represents a site binding to M¹.]

The metal complex represented by the formula (M) is preferably a metal complex represented by the formula Ir-1 to the formula Ir-5, more preferably a metal complex represented by the formula Ir-1 to the formula Ir-3, further preferably a metal complex represented by the formula Ir-1 or the formula Ir-2.

In the metal complex represented by the formula Ir-1, at least one of $R^{D1}$ to $R^{D8}$ is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula (D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1), the formula (D-B3) or the formula (D-C1) to the formula (D-C3) especially preferably an alkyl group or a group represented by the formula (D-A1), the formula (D-B1), the formula (D-C1) or the formula (D-C2), especially more preferably a group represented by the formula (D-A1), the formula (D-B1), the formula (D-C1) or the formula (D-C2), because synthesis of the metal complex represented by the formula Ir-1 is easy, and these groups each optionally have a substituent.

In the metal complex represented by the formula Ir-2, at least one of $R^{D11}$ to $R^{D20}$ is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula (D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1, the formula (D-B3) or the formula (D-C1) to the formula (D-C3), especially preferably an alkyl group or a group represented by the formula (D-A1), the formula (D-B1), the formula (D-C1) or the formula (D-C2), especially more preferably a group represented by the formula (D-A1), the formula (D-B1), the formula (D-C1) or the formula (D-C2), because synthesis of the metal complex represented by the formula Ir-2 is easy, and these groups each optionally have a substituent.

In the metal complex represented by the formula Ir-3, at least one of $R^{D1}$ to $R^{D8}$ and $R^{D11}$ to $R^{D20}$ is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula (D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1), the formula (D-B3) or the formulae (D-C1) to (D-C3), especially preferably an alkyl group or a group represented by the formula (D-A1), the formula (D-B1) the formula (D-C1) or the formula (D-C2), especially more preferably a group represented by the formula (D-A1), the formula (D-B1), the formula (D-C1) or the formula (D-C2) because the metal complex represented by the formula Ir-3 is easy, and these groups each optionally have a substituent.

In the metal complex represented by the formula Ir-4, at least one of $R^{21}$ to $R^{D26}$ is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula (D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1), the formula (D-B3) or the formula (D-C1) to the formula (D-C3), especially preferably an alkyl group or a group represented by the formula (D-A1), the formula (D-B1), the formula (D-C1) or the formula (D-C2), especially more preferably a group represented by the formula (D-A1), the formula (D-B1), the formula (D-C1) or the formula (D-C2), because the metal complex represented by the formula Ir-4 is easy, and these groups each optionally have a substituent.

In the metal complex represented by the formula Ir-5, at least one of $R^{D31}$ to $R^{D37}$ is preferably an alkyl group, a cycloalkyl group or a group represented by the formula (D-A) to the formula (D-C), more preferably an alkyl group or a group represented by the formula (D-A) to the formula (D-C), further preferably an alkyl group or a group represented by the formula (D-A1) to the formula (D-A4), the formula (D-B1) to the formula (D-B3) or the formula (D-C1) to the formula (D-C4). Of them, it is particularly preferably an alkyl group or a group represented by the formula (D-A1), the formula (D-A3), the formula (D-B1), the formula (D-B3) or the formula (D-C1) to the formula (D-C3), especially preferably an alkyl group or a group represented by the formula (D-A1), the formula (D-B1), the formula (D-C1) or the formula (D-C2), especially more preferably a group represented by the formula (D-A1), the formula (D-B1), the formula (D-C1) or the formula (D-C2), because the metal complex represented by the formula Ir-5 is easy, and these groups each optionally have a substituent.

The metal complex represented by the formula Ir-1 is preferably a metal complex represented by the formula Ir-11 to the formula Ir-13. The metal complex represented by the formula Ir-2 is preferably a metal complex represented by the formula Ir-21. The metal complex represented by the formula Ir-3 is preferably a metal complex represented by the formula Ir-31 to the formula Ir-33. The metal complex represented by the formula Ir-4 is preferably a metal complex represented by the formula Ir-41 to the formula Ir-43. The metal complex represented by the formula Ir-5 is preferably a metal complex represented by the formula Ir-51 to the formula Ir-53.

[Chemical Formula 41]

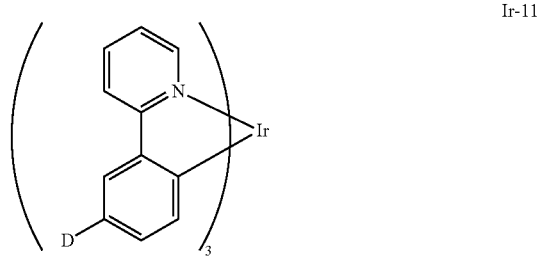

Ir-11

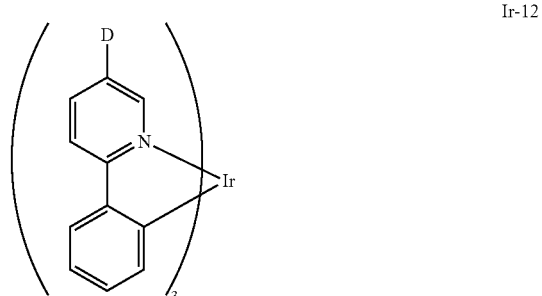

Ir-12

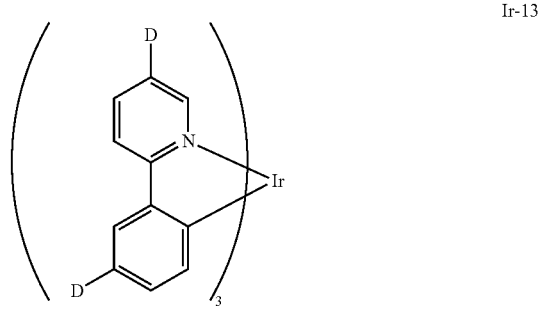

Ir-13

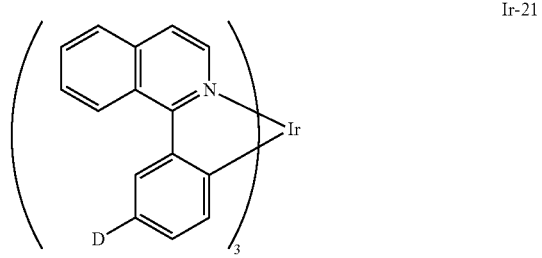

Ir-21

[Chemical Formula 42]

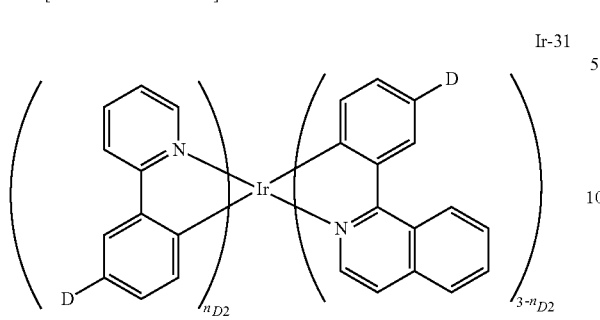

Ir-31

Ir-32

[Chemical Formula 43]

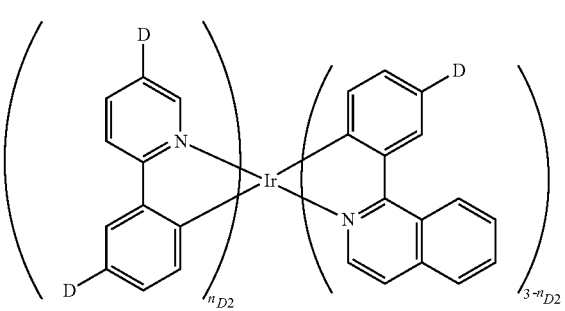

Ir-33

[Chemical Formula 44]

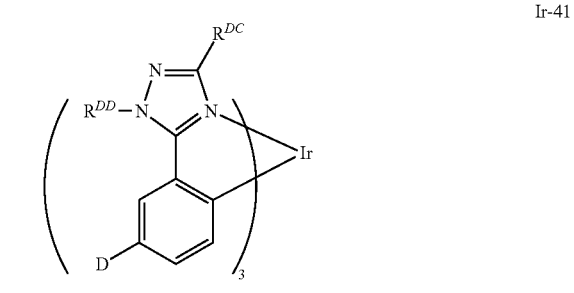

Ir-41

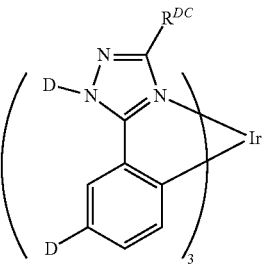

Ir-42

Ir-43

[Chemical Formula 45]

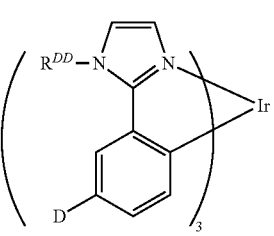

Ir-51

Ir-52

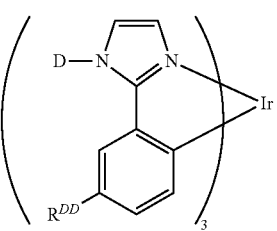

Ir-53

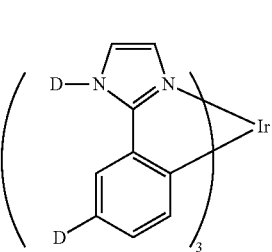

[wherein, $n_{D2}$ represents 1 or 2.

D represents a group represented by the formula (D-A) to the formula (D-C). The plurality of D may be the same or different.

$R^{DC}$ represents a hydrogen atom, an alkyl group, a cycloalkyl group, an aryl group or a monovalent heterocyclic group, and these groups each optionally have a substituent. The plurality of $R^{DC}$ may be the same or different.

$R^{DD}$ represents an alkyl group, a cycloalkyl group, an aryl group or a monovalent heterocyclic group, and these groups each optionally have a substituent. The plurality of $R^{DD}$ may be the same or different.]

The phosphorescent compound includes, for example, metal complexes shown below.

[Chemical Formula 46]
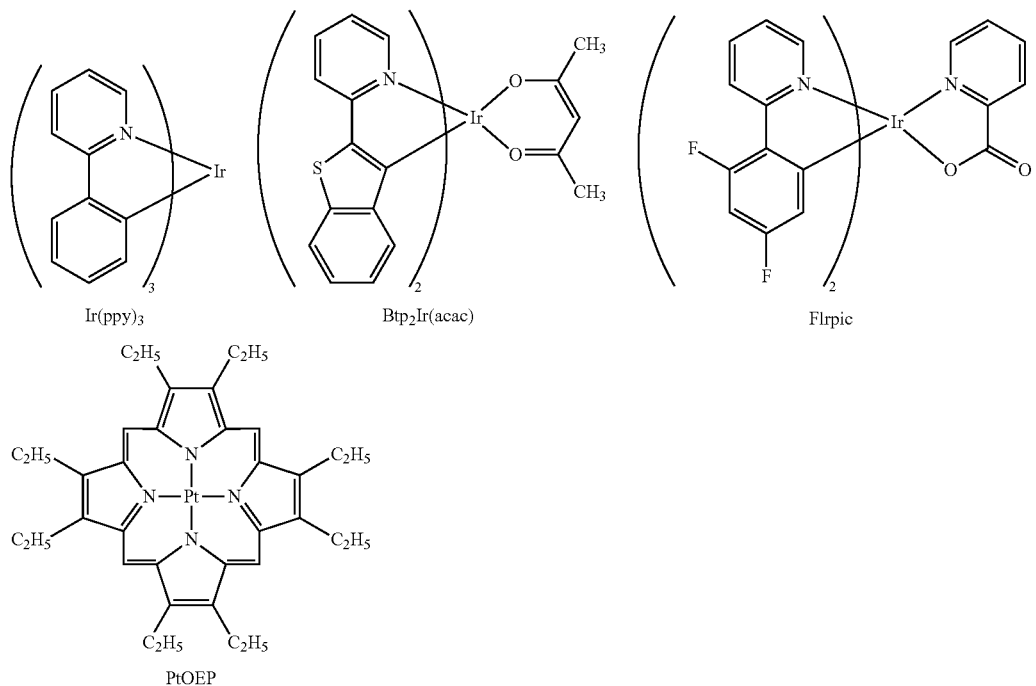
[Chemical Formula 47]
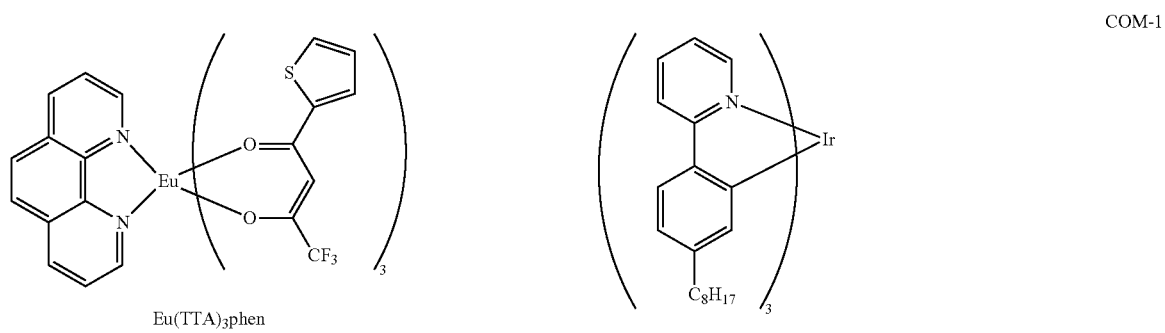
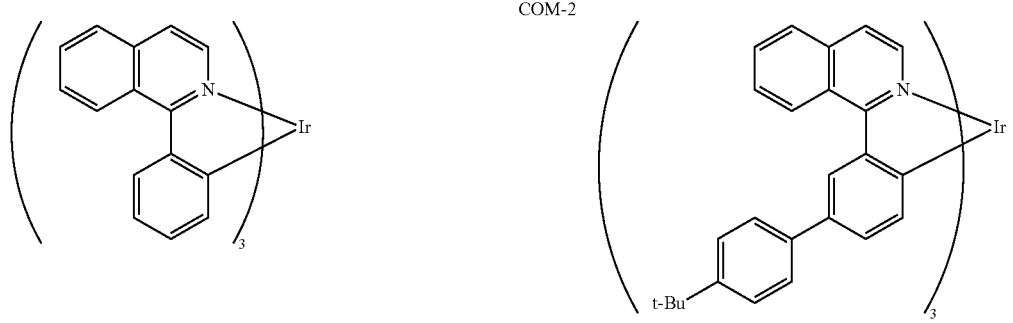

-continued
[Chemical Formula 48]
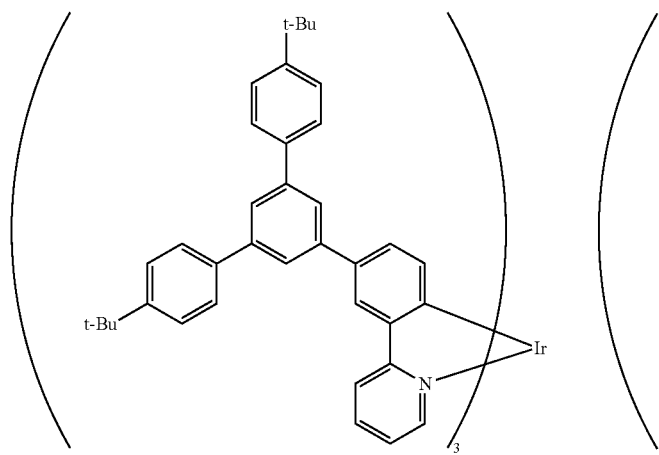
COM-4
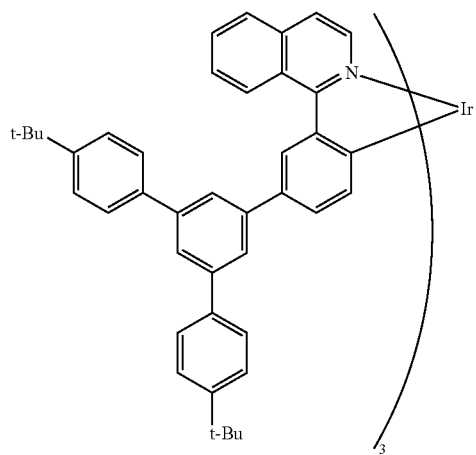
COM-5
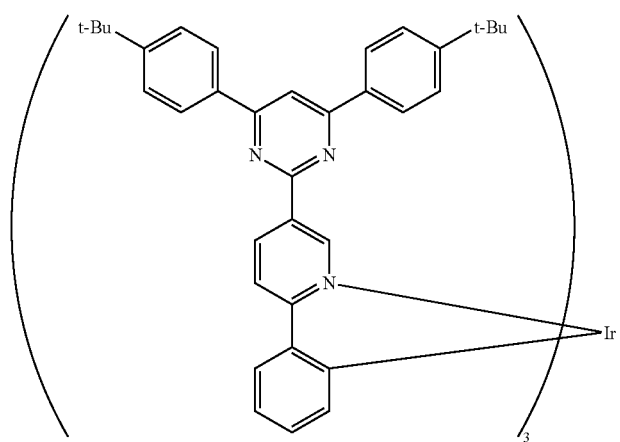
COM-6
[Chemical Formula 49]
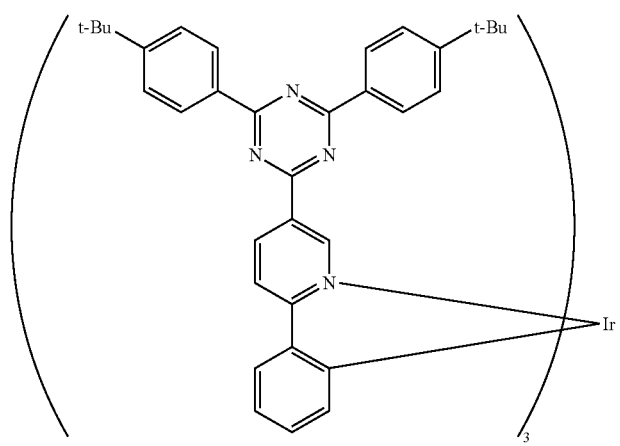
COM-7

-continued
COM-8
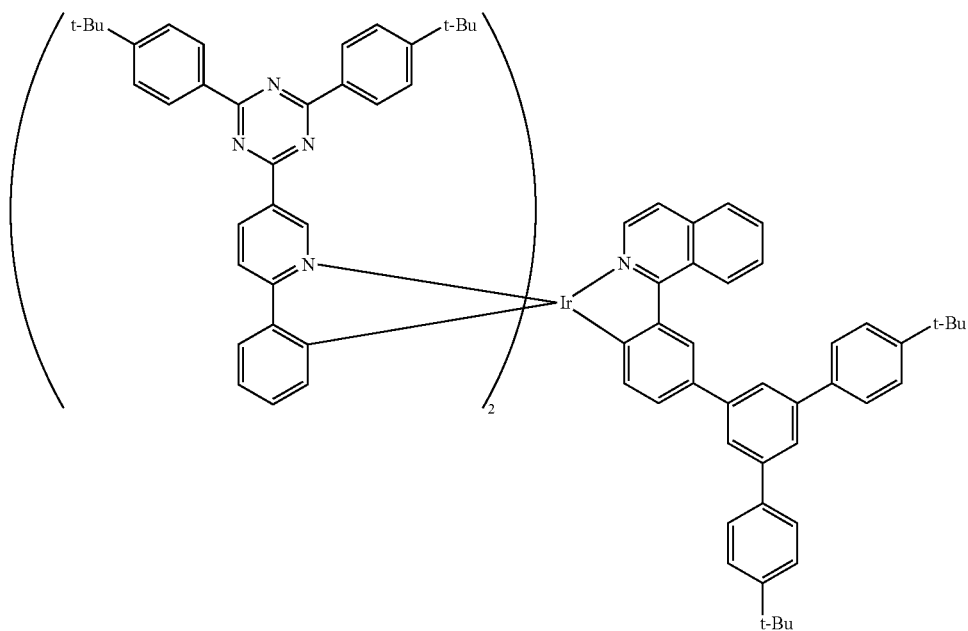
[Chemical Formula 50]
COM-9        COM-10
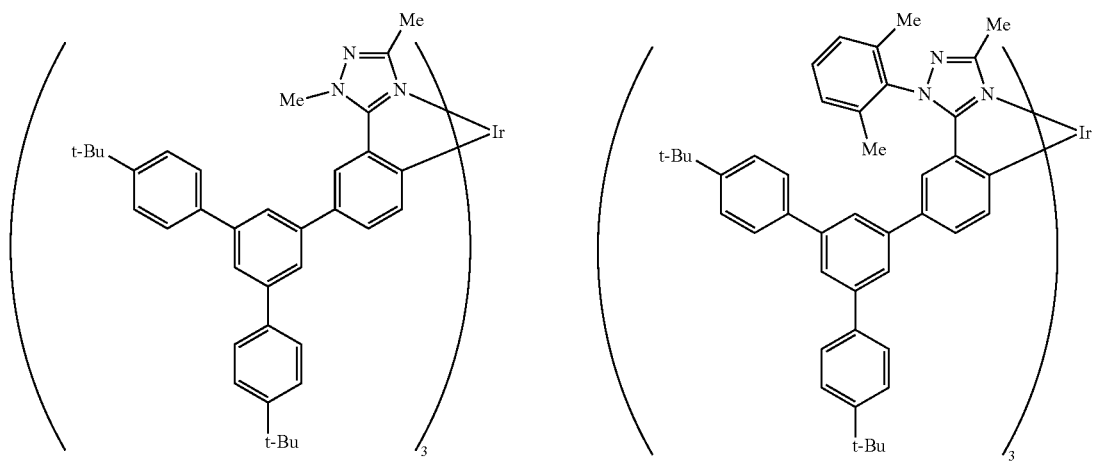
COM-11        COM-12
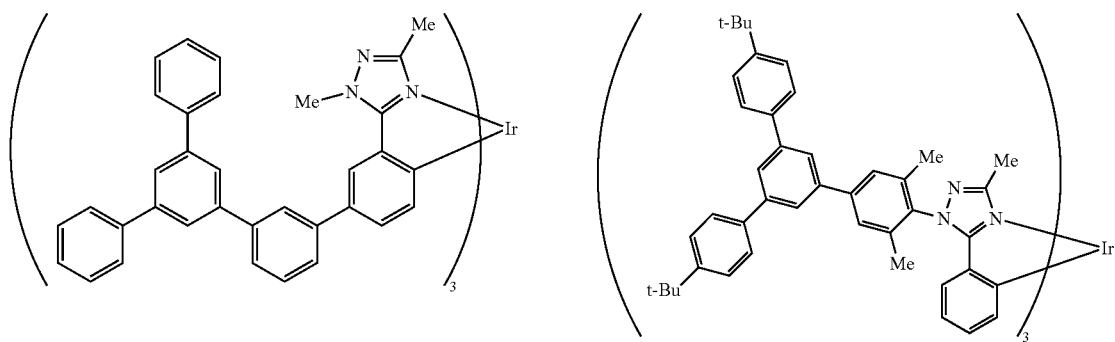

COM-13
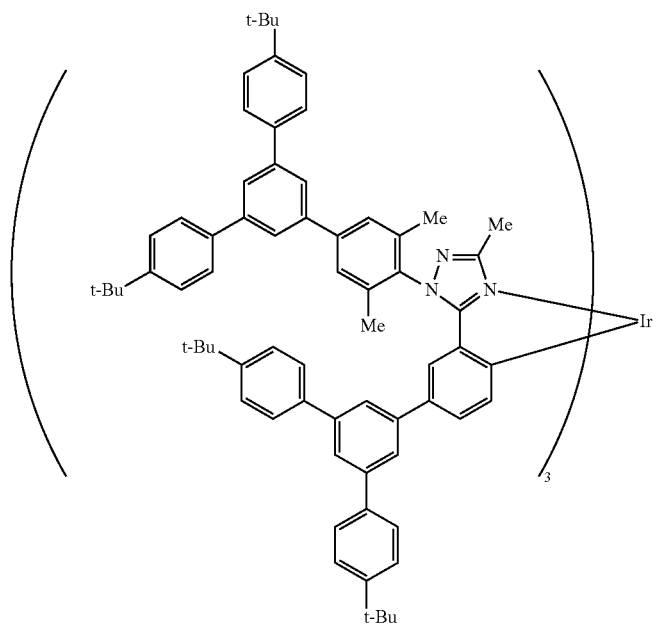
[Chemical Formula 51]
COM-14  COM-15
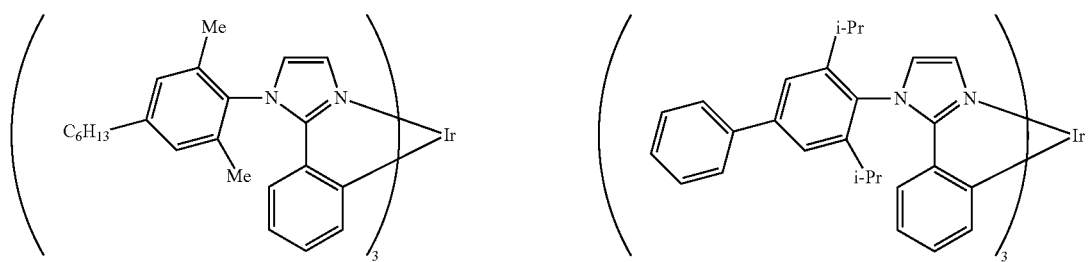
COM-16  COM-17
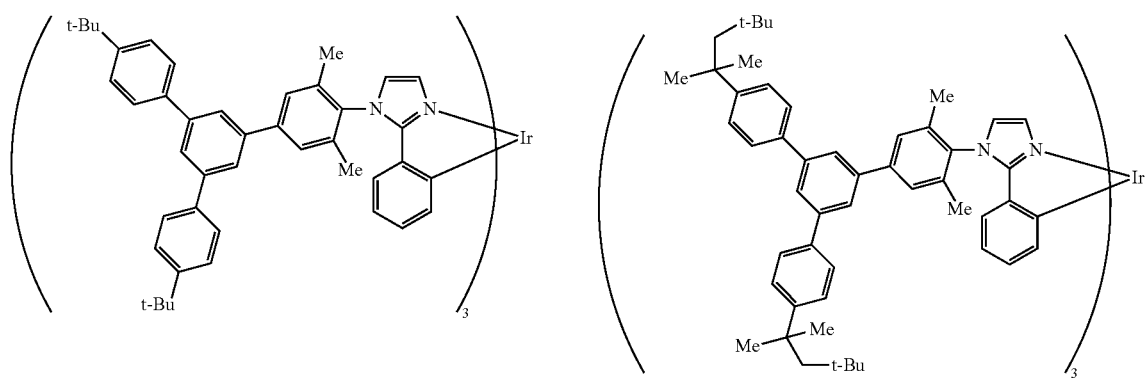

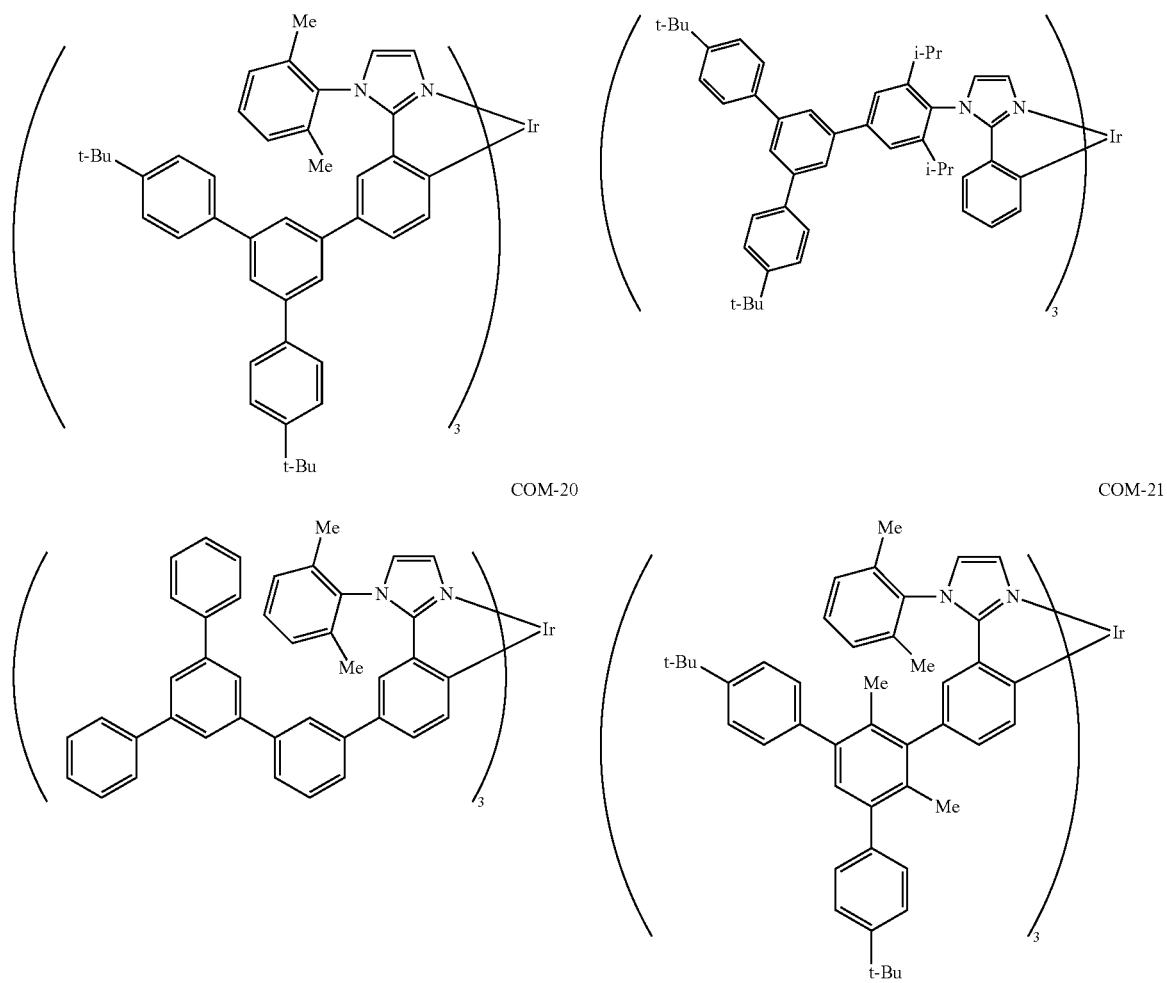

The phosphorescent compound is available from Aldrich, Luminescence Technology Corp., American Dye Source and the like.

The phosphorescent compound can be produced also by known methods described in documents such as Journal of the American Chemical Society, Vol. 107, 1431-1432 (1985), Journal of the American Chemical Society, Vol. 106, 6647-6653 (1984), International Publication WO2011/024761, International Publication WO2002/44189 and JP-A No. 2006-1.88673.

In the composition of the present invention, the content of the phosphorescent compound is usually 0.01 to 95 parts by weight, preferably 0.05 to 80 parts by weight, more preferably 0.1 to 60 parts by weight, further preferably 1 to 40 parts by weight, particularly preferably 10 to 30 parts by weight when the sum of the compound represented by the formula (1) and the phosphorescent compound is 100 parts by weight.

In the composition of the present invention, the phosphorescent compound may be used singly or two or more of the phosphorescent compounds may be used in combination.

It is preferable that the lowest excited triplet state ($T_1$) of the compound represented by the formula (1) has energy level equivalent to or higher than $T_1$ of the phosphorescent compound, because the light emitting device produced by using the composition of the present invention is excellent in light emission efficiency.

It is preferable that the compound represented by the formula (1) is one showing solubility in a solvent which is capable of dissolving the phosphorescent compound, because the light emitting device produced by using the composition of the present invention can be fabricated by a solution application process.

<Other Components>

The composition of the present invention may further comprise at least one material selected from the group consisting of a hole transporting material, a hole injection material, an electron transporting material, an electron injection material, a light emitting material (differing from a phosphorescent compound), and an antioxidant. The hole transporting material, the hole injection material, the electron transporting material and the electron injection material differ from a compound represented by the formula (1)

The composition of the present invention may further comprise a solvent.

The composition comprising a compound represented by the formula (1), a phosphorescent compound and a solvent (hereinafter, referred to as "ink") is suitable for fabrication of a light emitting device by using printing methods such as an inkjet printing method and a nozzle printing method.

The viscosity of the ink may be adjusted depending on the kind of the printing method, and when a solution goes through a discharge apparatus such as in an inkjet printing method, the viscosity is preferably in the range of 1 to 20 mPa·s at 25° C. because clogging in discharging and curved aviation are less likely to occur.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as tetrahydrofuran, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol and derivatives thereof; alcohol solvents such as isopropylalcohol and cyclohexanol; sulfoxide solvents such as dimethyl sulfoxide; and amide solvents such as N-methyl-2-pyrrolidone and N,N-dimethylformamide.

In the ink, the compounding amount of the solvent is usually 1000 to 100000 parts by weight, preferably 2000 to 20000 parts by weight when the total content of a compound represented by the formula (1) and a phosphorescent compound is 100 parts by weight.

The solvent may be used singly or two or more solvents may be used in combination.

[Hole Transporting Material]

The hole transporting material is classified into a low molecular weight compound and a polymer compound, and is preferably a polymer compound, more preferably a polymer compound having a crosslinkable group.

The polymer compound includes, for example, 6 polyvinylcarbazole and derivatives thereof; polyarylene having an aromatic amine structure in the side chain or main chain (for example, polytriphenylamine and fluorene-triphenylamine copolymer) and derivatives thereof. The polymer compound may also be a compound in which an electron accepting portion is linked. The electron accepting portion includes, for example, fullerene, tetrafluorotetracyanoquinodimethane, tetracyanoethylene and trinitrofluorenone, and is preferably fullerene.

In the composition of the present invention, the compounding amount of the hole transporting material is usually 0.1 to 1000 parts by weight, preferably 1 to 400 parts by weight, more preferably 5 to 150 parts by weight when the total content of a compound represented by the formula (1) and a phosphorescent compound is 100 parts by weight.

In the composition of the present invention, the hole transporting material may be used singly or two or more hole transporting materials may be used in combination.

[Electron Transporting Material]

The electron transporting material is classified into a low molecular weight compound and a polymer compound. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof.

The polymer compound includes, for example, polyphenylene (for example, polyphenylene and polyfluorene) and derivatives thereof. The polymer compound may be doped with a metal.

In the composition of the present invention, the compounding amount of the electron transporting material is usually 0.1 to 1000 parts by weight, preferably 1 to 400 parts by weight, more preferably 5 to 150 parts by weight when the total content of a compound represented by the formula (1) and a phosphorescent compound is 100 parts by weight.

In the composition of the present invention, the electron transporting material may be used singly or two or more electron transporting materials may be used in combination.

[Hole Injection Material and Electron Injection Material]

The hole injection material and the electron injection material are each classified into a low molecular weight compound and a polymer compound. The hole injection material and the electron injection material optionally have a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyarylene, polyarylenevinylene, polyheteroarylene, polyheteroarylenevinylene and derivatives thereof, and conductive polymers such as a polymer comprising an aromatic amine structure in the main chain or side chain, and is preferably polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the side chain or main chain.

In the composition of the present invention, the compounding amounts of the hole injection material and the electron injection material are each usually 0.1 to 1000 parts by weight, preferably 1 to 4-100 parts by weight, more preferably 5 to 150 parts by weight when the total content of a compound represented by the formula (1) and a phosphorescent compound is 100 parts by weight.

In the composition of the present invention, the hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1 \times 10^{-5}$ S/cm to $1 \times 10^{3}$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

[Light Emitting Material]

The light emitting material (differing from a phosphorescent compound) is classified into a low molecular weight compound and a polymer compound. The light emitting material optionally has a crosslinkable group.

The low molecular weight compound includes, for example, naphthalene and derivatives thereof, anthracene and derivatives thereof, and perylene and derivatives thereof.

The polymer compound includes, for example, polymer compounds comprising arylene groups such as a phenylene group, a naphthalenediyl group, a fluorenediyl group, a phenanthrenediyl group, dihydrophenanthrenediyl group, an anthracenediyl group and a pyrenediyl group, aromatic amine residues such as a group formed by removing from an aromatic amin two hydrogen atoms, or divalent heterocyclic groups such as a carbazolediyl group, a phenoxazinediyl group and a phenothiazinediyl group.

In the composition of the present invention, the compounding amount of the light emitting material is usually 0.1 to 1000 parts by weight, preferably 0.1 to 400 parts by weight when the total content of a compound represented by the formula (1) and a phosphorescent compound is 100 parts by weight.

The light emitting material may be used singly or two or more light emitting materials may be used in combination.

[Antioxidant]

The antioxidant may advantageously be one which is soluble in the same solvent as for the polymer compound of the present invention and does not disturb light emission and charge transportation, and the examples thereof include phenol antioxidants and phosphorus-based antioxidants.

In the composition of the present invention, the compounding amount of the antioxidant is usually 0.001 to 10 parts by weight when the total content of a compound represented by the formula (1) and a phosphorescent compound is 100 parts by weight.

The antioxidant may be used singly or two or more antioxidants may be used in combination.

<Film

The film comprises the composition of the present invent ion.

The film is suitable as a light emitting layer in a light emitting device.

The film can be fabricated, for example, by using a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method or a nozzle coating method, using the ink.

The thickness of the film is usually 1 nm to 10 µm.

<Light Emitting Device>

The light emitting device of the present invention is a light emitting device comprising the composition of the present invention.

The constitution of the light emitting device of the present invention has, for example, electrodes consisting of an anode and a cathode, and a layer comprising the composition of the present invention disposed between the electrodes.

[Layer Constitution]

The layer comprising the composition of the present invention is usually at least one selected from a light emitting layer, a hole transporting layer, a hole injection layer, an electron transporting layer and an electron injection layer, preferably a light emitting layer. These layers comprise a light emitting material, a hole transporting material, a hole injection material, an electron transporting material and an electron injection material, respectively. These layers can be formed by the same method as the above-described film fabrication using inks prepared by dissolving a light emitting material, a hole transporting material, a hole injection material, an electron transporting material and an electron injection material, respectively, in the solvent described above.

The light emitting device comprises a light emitting layer between an anode and a cathode. The light emitting device of the present invention preferably comprises at least one of a hole injection layer and a hole transporting layer between an anode and a light emitting layer from the standpoint of hole injectability and hole transportability, and preferably comprises at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the above-described hole transporting materials, electron transporting materials, light emitting materials, hole injection materials and electron injection materials, respectively, in addition to the composition of the present invention.

When the material of a hole transporting layer, the material of an electron transporting layer and the material of a light emitting layer are soluble in a solvent which is used in forming a layer adjacent to the hole transporting layer, the electron transporting layer and the light emitting layer, respectively, in fabrication of a light emitting device, it is preferable that the materials have a crosslinkable group to avoid dissolution of the materials in the solvent. After forming the layers using the materials having a crosslinkable group, the layers can be insolubilized by crosslinking the crosslinkable group.

Methods of forming respective layers such as a light emitting layer, a hole transporting layer, an electron transporting layer, a hole injection layer and an electron injection layer in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order and the number of layers to be laminated and the thickness of each layer may be controlled in view of external quantum efficiency and luminance life.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium•tin•oxide (ITO) and indium•zinc•oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross orthogonally with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

In examples, the polystyrene-equivalent number-average molecular weight (Mn) and the polystyrene-equivalent weight-average molecular weight (Mw) of a polymer compound were determined by the following size exclusion chromatography (SEC) using tetrahydrofuran as a mobile phase. Measurement conditions of SEC are as described below.

A polymer compound to be measured was dissolved in tetrahydrofuran at a concentration of about 0.05 wt %, and 10 μl of the solution was injected into SEC. A mobile phase was flowed at a flow rate of 2.0 mL/min. As the column, PLgel MIXED-B (manufactured by Polymer Laboratories Ltd.) was used. As the detector, an UV-VIS detector (manufactured by Shimadzu Corp., tradename: SPD-10Avp) was used.

LC-MS was measured by the following method.

A measurement sample was dissolved in chloroform or tetrahydrofuran so as to give a concentration of about 2 mg/mL, and about 1 μL of the solution was injected into LC-MS (manufactured by Agilent Technologies, tradename: 1100LCMSD). As the mobile phase of LC-MS, acetonitrole and tetrahydrofuran were used while changing the ratio thereof, and flowed at a flow rate of 0.2 mL/min. As the column, L-column 2 ODS (3 μm) (manufactured by Chemicals Evaluation and Research institute, Japan, internal diameter: 2.1 mm, length: 100 mm, particle size: 3 μm) was used.

TLC-MS was measured by the following method.

A measurement sample was dissolved in any solvent of toluene, tetrahydrofuran or chloroform at any concentration, and the solution was applied on a TLC plate for DART (manufactured by Techno Applications Co., tradename: YSK5-100), and TLC-MS was measured using TLC-MS (manufactured by JEOL Ltd., tradename: JHS-T100TD1 (The AccuTOF TLC)). The temperature of a helium gas in measurement was controlled in the range of 200 to 400° C.

NMR was measured by the following method.

Five to ten milligrams of a measurement sample was dissolved in about 0.5 mL of deuterated chloroform (CDCl$_3$), deuterated tetrahydrofuran, deuterated dimethyl sulfoxide, deuterated acetone, deuterated N,N-dimethylformamide, deuterated toluene, deuterated methanol, deuterated ethanol, deuterated 2-propanol or deuterated methylene chloride, and NMR was measured using an NMR apparatus (manufactured by Agilent Technologies, tradename: INOVA300 or MERCURY 400VX).

As the index of the purity of a compound, the value of high performance liquid chromatography (HPLC) area percentage was used. This value is a value at UV=254 nm by HPLC (manufactured by Shimadzu Corp., tradename: LC-20A), unless otherwise stated. In this operation, a compound to be measured was dissolved in tetrahydrofuran or chloroform so as to give a concentration of 0.01 to 0.2 wt %, and 1 to 10 μL of the solution was injected into HPLC, depending on the concentration. As the mobile phase of HPLC, acetonitrile and tetrahydrofuran were used while changing the ratio of acetonitrile/tetrahydrofuran from 100/0 to 0/100 (volume ratio), and flowed at a flow rate of 1.0 mL/min. As the column, Kaseisorb LC ODS 2000 (manufactured by Tokyo Chemical Industry Co., Ltd.) or an ODS column having the equivalent performance was used. As the detector, a photodiode array detector (manufactured by Shimadzu Corp., tradename: SPD-M20A) was used.

<Synthesis Examples M1 to M12> Synthesis of Compounds M1 to M12

A compound M1 was synthesized according to a method described in JP-A No. 2011-174062.

A compound M2 was synthesized according to a method described in International Publication WO2002/045184.

A compound M3 was synthesized according to a method described in International Publication WO2005/049546.

A compound M4 was synthesized according to a method described in JP-A No. 2008-106241.

A compound M5 was synthesized according to a method described in JP-A No. 2015-086215.

A compound M6 was synthesized according to a method described in International Publication WO2009/131255.

A compound M7 was synthesized according to a method described in JP-A No. 2004-143419.

A compound M8 was synthesized according to a method described in JP-A No. 2010-189630.

A compound M9 was synthesized according to a method described in international Publication WO2012/086671.

A compound M10 was synthesized according to a method described in JP-A No. 2010-189630.

A compound M11 was synthesized according to a method described in International Publication WO2015/145871.

A compound M12 was synthesized according to a method described in International Publication WO02013/146806.

[Chemical Formula 52]

compound M1

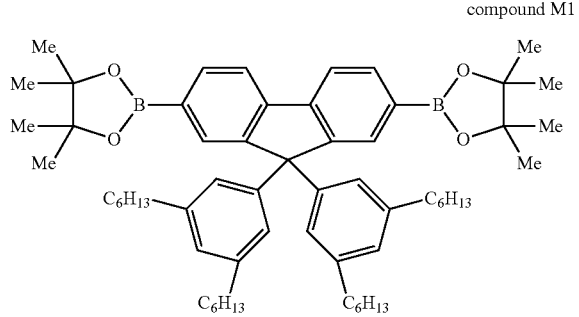

compound M2

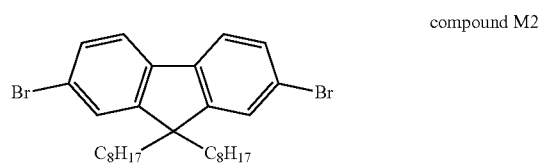

compound M3
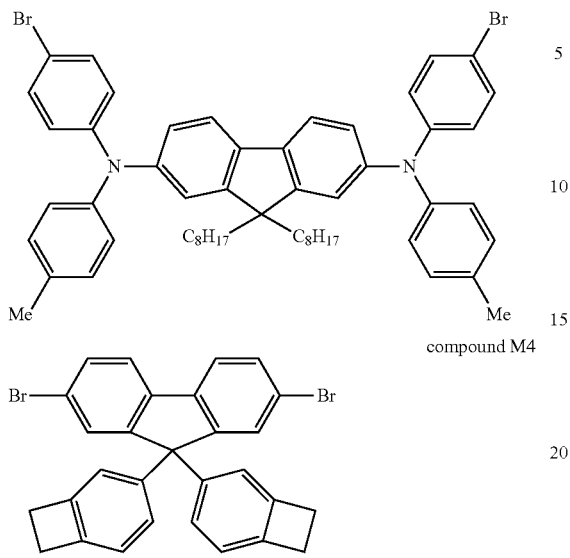
compound M4
[Chemical Formula 53]
compound M5
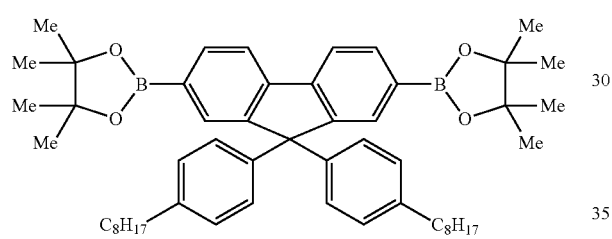
compound M6
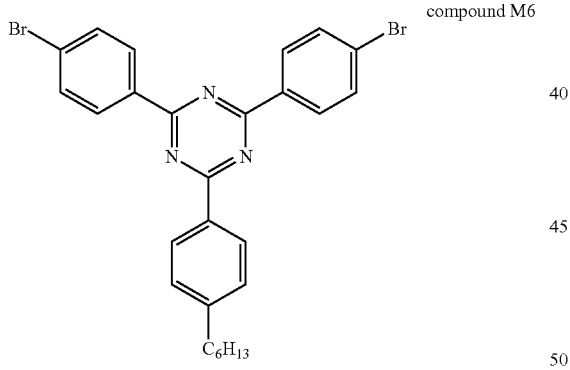
compound M7
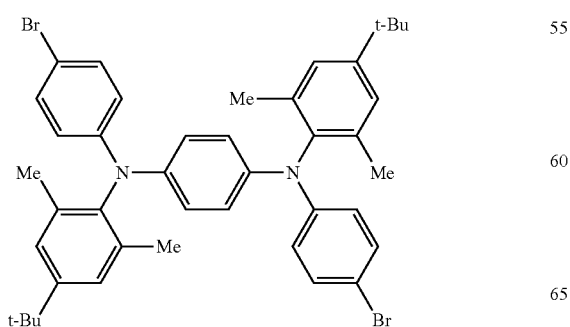
[Chemical Formula 54]
compound M8
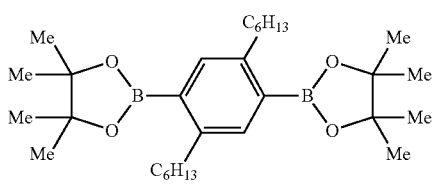
compound M9
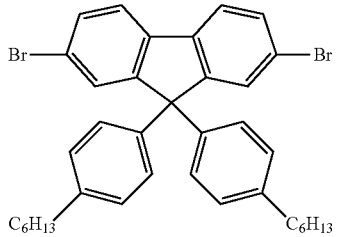
compound M10
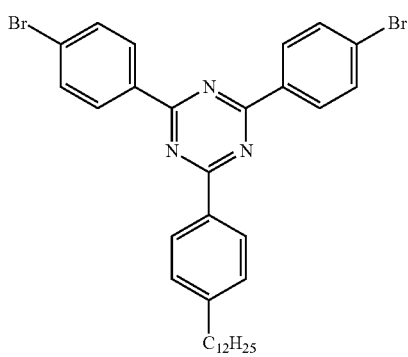
[Chemical Formula 55]
compound M11
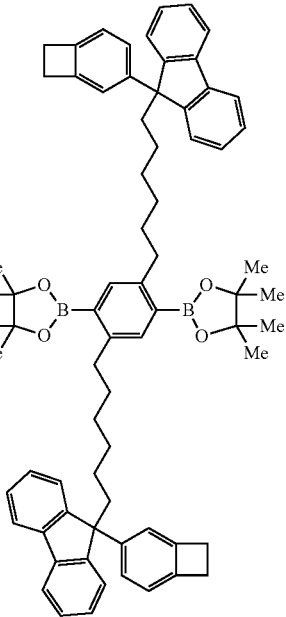

compound M12

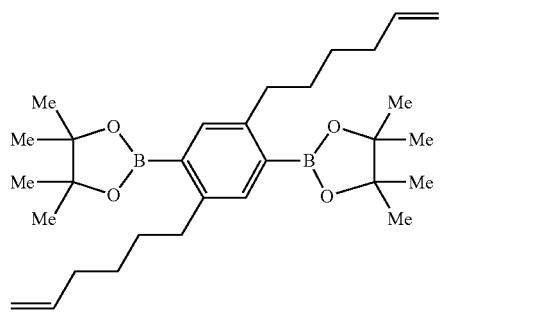

<Synthesis Example HTL1> Synthesis of Polymer Compound HTL-1

An inert gas atmosphere was prepared in a reaction vessel, then, the compound M1 (2.69 g), the compound M2 (0.425 g), the compound M3 (1.64 g), the compound M4 (0.238 g) dichlorobis(triphenylphosphine) palladium (2.1 mg) and toluene (62 ml) were added, and the mixture was heated at 105° C.

Into the resultant reaction liquid was dropped a 20 wt % tetraethylammonium hydroxide aqueous solution (10 ml), and the mixed liquid was refluxed for 4.5 hours.

To the resultant reaction mixture were added phenylboronic acid (36.8 mg) and dichlorobis(triphenylphosphine) palladium (2.1 mg), and the mixture was refluxed for 16.5 hours.

To the resultant reaction mixture was added a sodium diethyldithiocarbamate aqueous solution, and the mixture was stirred at 80° C. for 2 hours. After cooling, the reaction liquid was washed twice with water, twice with a 3 wt % acetic acid aqueous solution and twice with water, and the resultant solution was dropped into methanol, to observe generation of a precipitate. The precipitate was dissolved in toluene, and purified by passing through an alumina column and a silica gel column in this order.

The resultant solution was dropped into methanol, the mixed liquid was stirred, then, the resultant precipitate was isolated by filtration and dried, to obtain 0.3.12 g of a polymer compound HTL-1. The polymer compound HTL-1 had an Mn of $7.8 \times 10^4$ and an Mw of $2.6 \times 10^5$.

The polymer compound HTL-1 is a copolymer constituted of a constitutional unit derived from the compound M1, a constitutional unit derived from the compound M2, a constitutional unit derived from the compound M3 and a constitutional unit derived from the compound M4 at a molar ratio of 50:12.5:30:7.5 according to the theoretical values calculated from the amounts of the charged raw materials.

<Synthesis Example HTL2> Synthesis of Polymer Compound HTL-2

A polymer compound HTL-2 was synthesized according to a method described in International Publication WO2015/145871 using the compound M11, the compound M12 and the compound M3. The polymer compound HTL-2 had an Mn of $2.3 \times 10^4$ and an Mw of $1.2 \times 10^5$.

The polymer compound HTL-2 is a copolymer constituted of a constitutional unit derived from the compound M11, a constitutional unit derived from the compound M12 and a constitutional unit derived from the compound M3 at a molar ratio of 45:5:50 according to the theoretical values calculated from the amounts of the charged raw materials.

<Synthesis Example HP1> Synthesis of Polymer Compound HP-1

An inert gas atmosphere was prepared in a reaction vessel, then, the compound M5 (4.77 g), the compound M9 (0.773 g), the compound M2 (1.97 g), the compound M6 (0.331 g), the compound M7 (0.443 g) and toluene (67 ml) were added, and the mixture was stirred while heating at 105° C.

To the resultant reaction mixture was added bis(triphenylphosphine) palladium(II) dichloride (4.2 mg), then, a 20 wt % tetraethylammonium hydroxide aqueous solution (20 ml) was dropped, then, the mixture was stirred for 3 hours under reflux.

To the resultant reaction mixture were added phenylboronic acid (0.077 g), bis(triphenylphosphine)palladium(II) dichloride (4.2 mg), toluene (60 ml) and a 20 wt % tetraethylammonium hydroxide aqueous solution (20 ml), and the mixture was stirred for 24 hours under reflux.

The organic layer and the aqueous layer of the resultant reaction mixture were separated, then, to the resultant organic layer were added sodium N,N-diethyldithiocarbamate trihydrate (3.33 g) and ion exchanged water (67 ml), and the mixture was stirred at 85° C. for 2 hours. The organic layer and the aqueous layer of the resultant reaction mixture were separated, then, the resultant organic layer was washed twice with ion exchanged water (78 ml), twice with a 3 wt % acetic acid aqueous solution (78 ml) and twice with ion exchanged water (78 ml) in this order. The organic layer and the aqueous layer of the resultant washed material were separated, then, the resultant organic layer was cropped into methanol to cause precipitation of a solid which was then isolated by filtration and dried, to obtain a solid. This solid was dissolved in toluene, and the resultant solution was allowed to pass through a silica gel column and an alumina column through which toluene had passed previously. The resultant solution was dropped into methanol to cause precipitation of a solid which was then isolated by filtration and dried, to obtain a polymer compound HP-1 (4.95 g). The polymer compound HP-1 had an Mn of $1.4 \times 10^5$ and an Mw of $4.1 \times 10^5$.

The polymer compound HP-1 is a copolymer constituted of a constitutional unit derived from the compound M5, a constitutional unit derived from the compound M9, a constitutional unit derived from the compound M2, a constitutional unit derived from the compound M6 and a constitutional unit derived from the compound M7 at a molar ratio of 50:10:30:5:5 according to the theoretical values calculated from the amounts of the charged raw materials.

<Synthesis Example HP2> Synthesis of Polymer Compound HP-2

A polymer compound HP-2 was synthesized according to a method described in JP-A No. 2012-036388 using the compound M8, the compound M9 and the compound M10. The polymer compound HP-2 had an Mn of $9.6 \times 10^4$ and an Mw of $2.2 \times 10^5$.

The polymer compound HP-2 is a copolymer constituted of a constitutional unit derived from the compound MS, a constitutional unit derived from the compound M9 and a constitutional unit derived from the compound M10 at a molar ratio of 50:40:10 according to the theoretical values calculated from the amounts of the charged raw materials.

<Synthesis Examples G1 to G4> Synthesis of Phosphorescent Compounds G1 to G4

A phosphorescent compound G1 was synthesized according to a method described in JP-A No. 2013-237789. A phosphorescent compound G2 was synthesized according to a method described in International Publication WO2009/

131255. A phosphorescent compound G3 was synthesized based on a method described in International Publication WO2011/032626. A phosphorescent compound G4 was synthesized according to a method described in JP-A No. 2014-224101.
[Chemical Formula 56]
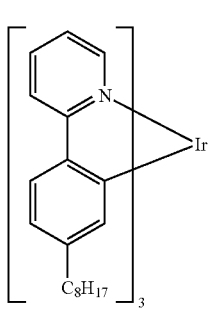
Phosphorescent compound G1
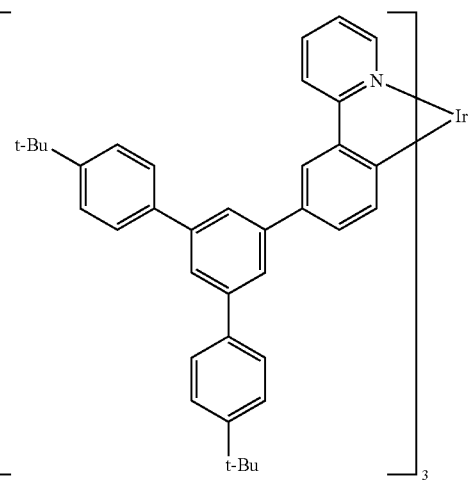
Phosphorescent compound G2
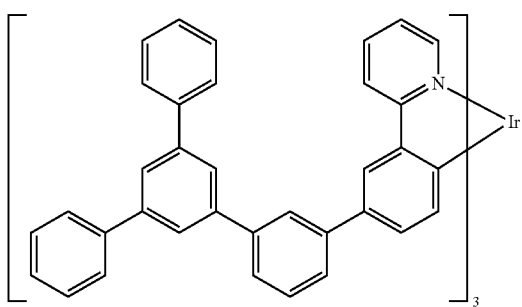
Phosphorescent compound G3
[Chemical Formula 57]
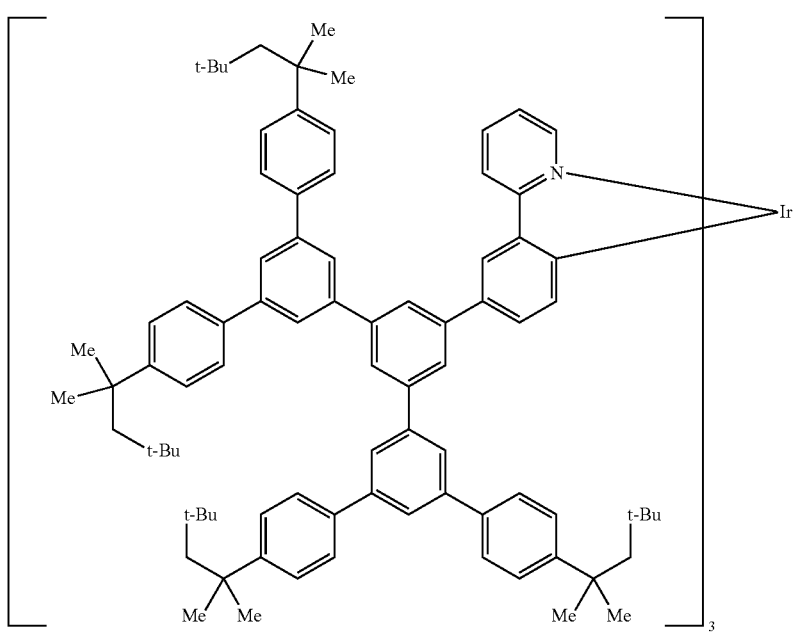
Phosphorescent compound G4

<Synthesis Examples R1 and R2> Synthesis of Phosphorescent Compounds R1 and R2

A phosphorescent compound R1 was synthesized based on a method described in international Publication WO2002/44189. A phosphorescent compound R2 was synthesized based on a method described in JP-A No. 2006-188673.

[Chemical Formula 58]

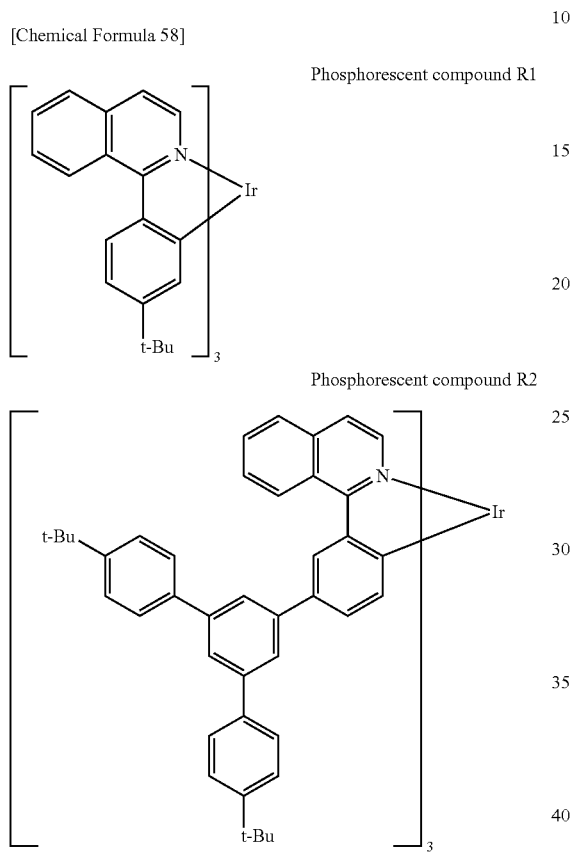

<Synthesis Example B1> Synthesis of Phosphorescent Compound B1

A phosphorescent compound B1 was synthesized based on a method described in International Publication WO2006/121811 and JP-A No. 2013-048190.

[Chemical Formula 59]

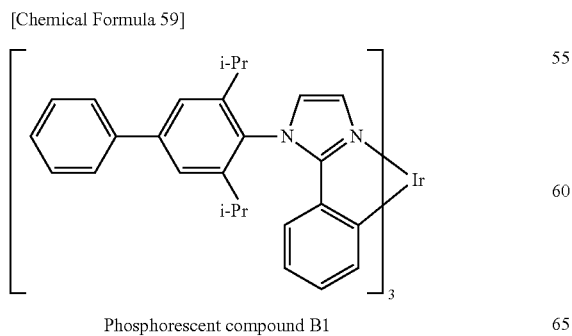

Phosphorescent compound B1

<Synthesis Example H1> Synthesis of Compound H1
[Chemical Formula 60]
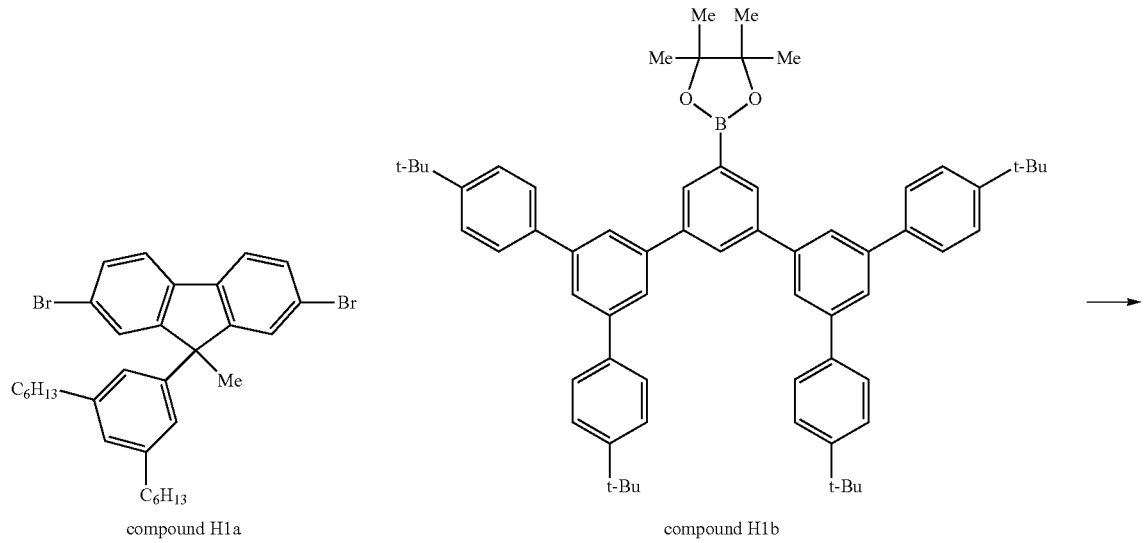
compound H1a        compound H1b
compound H1

A nitrogen atmosphere was prepared in a reaction vessel, then, a compound H1a (5.00 g) synthesized according to a method described in JP-A No. 2012-144722, a compound H1b (4.94 g) synthesized according to a method described in JP-A No. 2015-110751, dichlorobis(triphenylphosphine)palladium(II) (0.121 g), a 20 wt % tetraethylammonium hydroxide aqueous solution (2.53 g) and toluene (200 ml) were added, and the mixture was stirred at 55° C. for 2 hours. The resultant reaction mixture was cooled down to room temperature, then, ion exchanged water was added, and the mixed liquid was filtrated through a filter paved with Celite. The aqueous layer was removed from the resultant filtrate, then, the resultant organic layer was concentrated under reduced pressure. To the resultant concentrate were added hexane, toluene and activated carbon, and the mixture was stirred at room temperature for 1 hour, then, filtrated through a filter paved with Celite, and the resultant filtrate was concentrated under reduced pressure, to obtain a solid. This solid was purified by silica gel column chromatography (a mixed solvent of hexane and toluene, and, a mixed solvent of hexane and ethyl acetate), and further washed with acetone, then, dried under reduced pressure, to obtain a compound H1 (1.1 g). The compound H1 had an HPLC area percentage value of 99.5% or more.

LC-MS (ESI, positive): m/z=1937 $[M]^+$

<Synthesis Examples H2a and H3a> Synthesis of Compounds H2a and H3a

An argon atmosphere was prepared in a reaction vessel, then, a compound H1c (35.9 g) synthesized according to a method described in JP-A No. 2012-144722, a compound H1d (6.91 g) synthesized based on a method described in JP-A No. 2012-144'722, tetrakis(triphenylphosphine) palladium (0) (120 mg), a 20 wt % tetraethylammonium hydroxide aqueous solution (20 ml), toluene (85 ml), tert-butyl alcohol (55 ml), ion exchanged water (30 ml) and tetrahydrofuran (40 ml) were added, and the mixture was stirred at 85° C. for 2 hours. The resultant reaction mixture was cooled down to room temperature, and the aqueous layer was removed. The resultant organic layer was washed with saturated saline, then, dried over anhydrous sodium sulfate, and filtrated. The resultant filtrate was concentrated under reduced pressure, to obtain a coarse product. This coarse product was purified by silica gel column chromatography (a mixed solvent of hexane and ethyl acetate), and further purified by silica gel (ODS) column chromatography (a mixed solvent of tetrahydrofuran and acetonitrile), to obtain a compound H2a (9.87 g) and a compound H3a (2.11 g), respectively. This operation was repeated, to obtain a necessary amount of the compound H2a and a necessary amount of the compound H3a, respectively.

The NMR measurement results of the compound H2a were as described below.

$^1$H-NMR (300 MHz, CDCl$_3$): δ=0.68-0.93 (m, 24H), 1.02-1.36 (m, 48H), 1.48-1.61 (m, 6H), 2.37-2.61 (m, 12H), 6.88-7.06 (m, 8H), 7.07-7.18 (m, 4H), 7.34 (s, 2H), 7.38-7.49 (m, 6H), 7.51-7.64 (m, 6H), 7.68-7.80 (m, 4H)

[Chemical Formula 61]

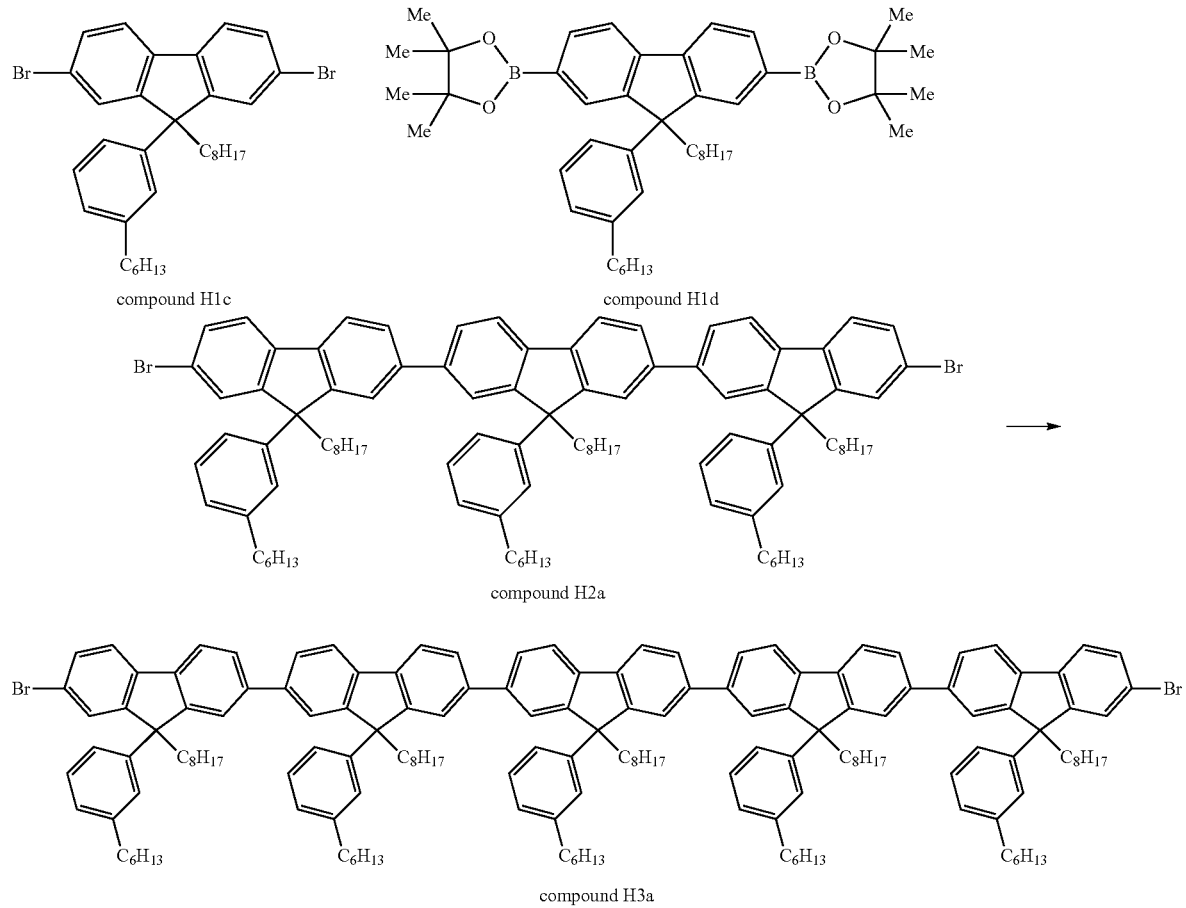

The NMR measurement results of the compound H3a were as described below.

$^1$H-NMR (300 MHz, CDCl$_3$): δ=0.67-0.95 (m, 40H), 1.03-1.37 (m, 80H), 1.48-1.63 (m, 10H), 2.35-2.62 (m, 20H), 6.88-7.07 (m, 12H), 7.07-7.18 (m, 8H), 7.34 (s, 2H), 7.39-7.49 (m, 10H), 7.50-7.65 (m, 10H), 7.68-7.84 (m, 8H)

<Synthesis Example H2b> Synthesis of Compound H2b

[Chemical Formula 62]

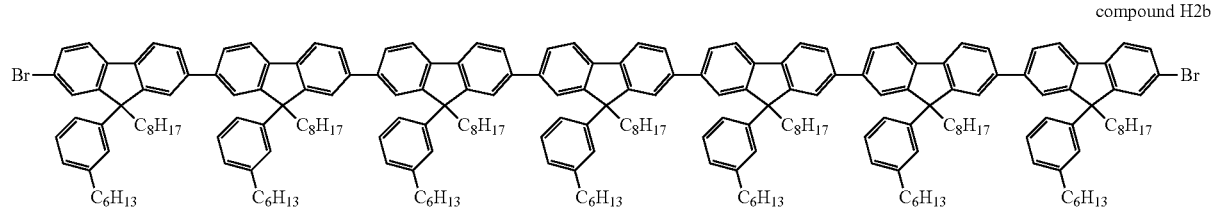

compound H2b

An argon atmosphere was prepared in a reaction vessel, then, the compound H2a (4.70 g), a compound H1d (0.55 g) synthesized based on a method described in JP-A No. 2012-144722, tetrakis(triphenylphosphine)palladium(0) (10 mg), a 20 wt % tetraethylammonium hydroxide aqueous solution (2 ml), toluene (7 ml), tert-butyl alcohol (5 ml), ion exchanged water (2 ml) and tetrahydrofuran (3 ml) were added, and the mixture was stirred at 85° C. for 2 hours. The resultant reaction mixture was cooled down to room temperature, and the aqueous layer was removed. The resultant organic layer was washed with saturated saline, then, dried over anhydrous sodium sulfate, and filtrated. The resultant filtrate was concentrated under reduced pressure, to obtain a coarse product. This coarse product was purified twice by silica gel (ODS) column chromatography (a mixed solvent of tetrahydrofuran and acetonitrile), to obtain a compound H2b (1.66 g). This operation was repeated, to obtain a necessary amount of the compound H2b.

The NMR measurement results of the compound B12b were as described below.

$^1$H-NHR (300 MHz, CDCl$_3$): δ=0.66-0.95 (m, 56H), 1.00-1.35 (m, 112H), 1.48-1.60 (m, 14H), 2.38-2.64 (m, 28H), 6.89-7.06 (m, 16H), 7.07-7.18 (m, 12H), 7.34 (s, 2H), 7.38-7.50 (m, 14H), 7.51-7.64 (m, 14H), 7.68-7.84 (m, 12H)

<Synthesis Example H2> Synthesis of Compound H2

An argon atmosphere was prepared in a reaction vessel, then, the compound H2b (4.70 g), phenylboronic acid (0.32 g), tetrakis(triphenylphosphine)palladium(0) (8 mg), a 20 wt % tetraethylammonium hydroxide aqueous solution (1 ml), toluene (6 ml), tert-buty alcohol (4 ml), ion exchanged water (2 ml) and tetrahydrofuran (3 ml) were added, and the mixture was stirred for 5 hours at 85° C. The resultant reaction mixture was cooled down to room temperature, then, ethyl acetate was added and extraction was performed. The resultant organic layer was dried over anhydrous sodium sulfate, then, filtrated. The resultant filtrate was concentrated under reduced pressure, to obtain a coarse product. This coarse product was purified by silica gel (ODS) column chromatography (a mixed solvent of tetrahydrofuran and acetonitrile), and further, crystallized using hexane and ethanol. The resultant solid was washed with ethanol and dried under reduced pressure, to obtain a compound H2 (1.23 g). The compound H2 had an HPLC area percentage value of 99.5% or more.

The NMR measurement results of the compound H2 were as described below.

$^1$H-NMR (300 MHz, CDCl$_3$): δ=0.66-0.96 (m, 56H), 1.00-1.35 (m, 112H), 1.45-1.64 (m, 14H), 2.38-2.64 (m, 28H), 6.92-7.06 (m, 14H), 7.07-7.20 (m, 14H), 7.27-7.36 (m, 2H), 7.37-7.51 (m, 18H), 7.52-7.66 (m, 18H), 7.70-7.88 (m, 14H).

[Chemical Formula 63]

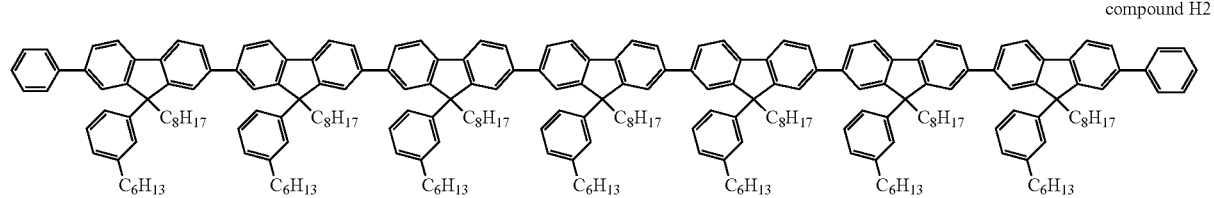

compound H2

<Synthesis Example H3> Synthesis of Compound H3

[Chemical Formula 64]

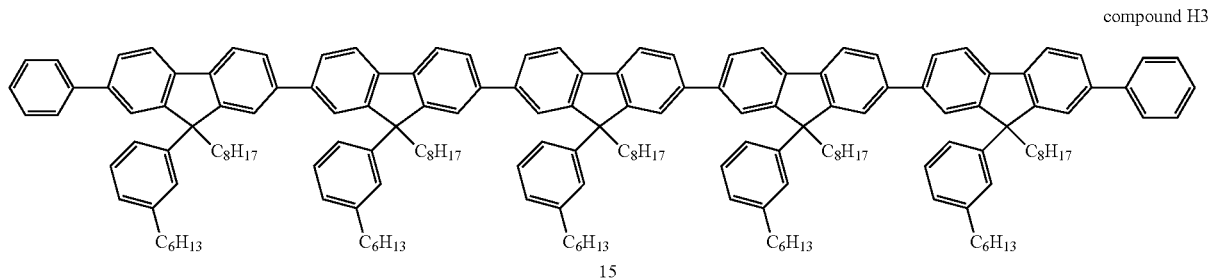

compound H3

An argon atmosphere was prepared in a reaction vessel, then, the compound H3a (2.11 g), phenylboronic acid (0.44 g), tetrakis(triphenylphosphine)palladium(0) (10 mg), a 20 wt % tetraethylammonium hydroxide aqueous solution (2 ml), toluene (8 ml), tert-butyl alcohol (5 ml), ion exchanged water (3 ml) and tetrahydrofuran (4 ml) were added, and the mixture was stirred for 8 hours at 85° C. The resultant reaction mixture was cooled down to room temperature, then, ethyl acetate was added and extraction was performed. The resultant organic layer was dried over anhydrous sodium sulfate, then, filtrated through a filter paved with Celite. The resultant filtrate was concentrated under reduced pressure, to obtain a coarse product. This coarse product was purified by silica gel (ODS) column chromatography (a mixed solvent of tetrahydrofuran and acetonitrile), and further, crystallized using hexane and ethanol. The resultant solid was washed with ethanol and dried under reduced pressure, to obtain a compound H3 (1.52 g). The compound H3 had an HPLC area percentage value of 99.5% or more.

The NMR measurement results of the compound H3 were as described below.

$^1$H-NMR (300 MHz, CDCl$_3$): δ=0.67-0.96 (m, 40H), 1.01-1.37 (m, 80H), 1.45-1.64 (m, 10H), 2.34-2.64 (m, 20H), 6.93-7.07 (m, 10H), 7.08-7.19 (m, 10), 7.27-7.36 (m, 2H), 7.37-7.51 (m, 14H), 7.53-7.64 (m, 14H), 7.72-7.84 (m, 10H)

<Synthesis Example H4> Synthesis of Compound 1-4

A compound H4 was synthesized based on a method described in International Publication WO2013/108022.

[Chemical Formula 65]

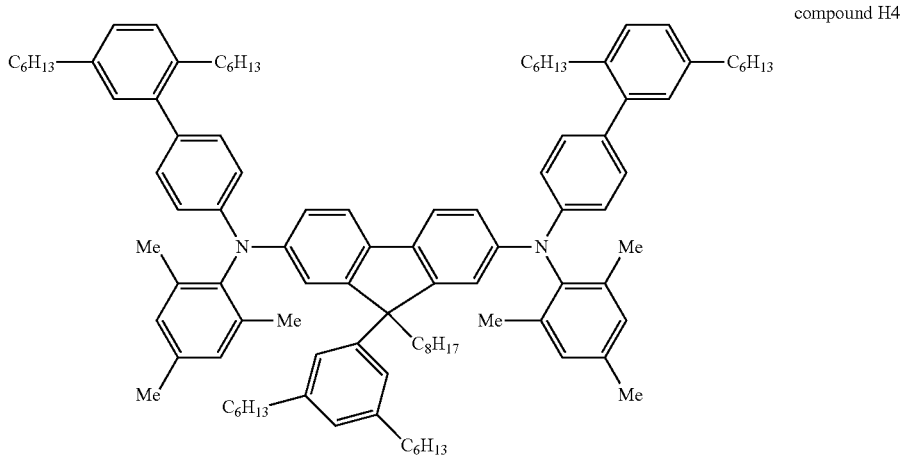

compound H4

<Synthesis Example H5> Synthesis of Compound H5

(Synthesis of Compound H5-1b)

[Chemical Formula 66]

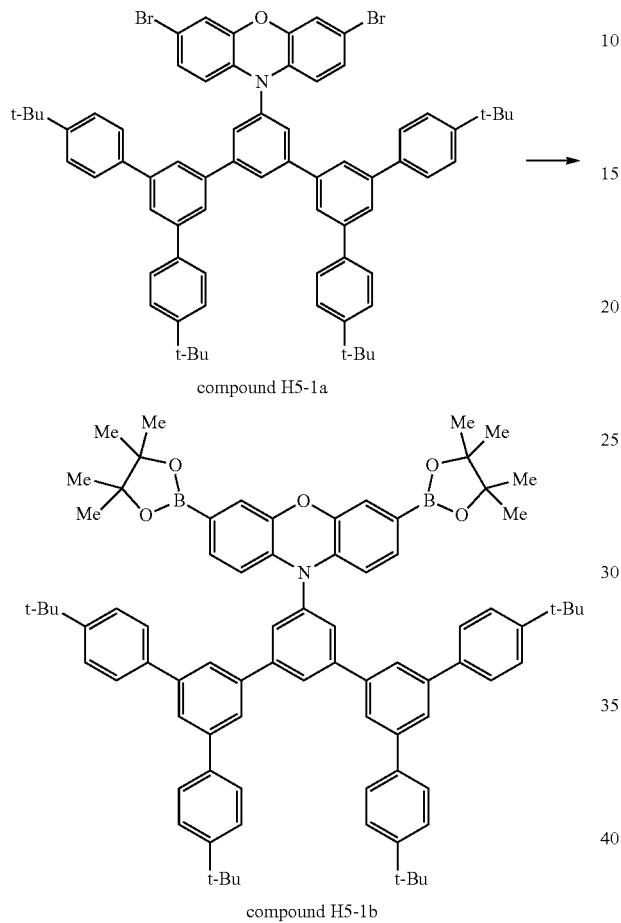

compound H5-1a compound H5-1b

A nitrogen atmosphere was prepared in a reaction vessel, then, a compound H5-1a (50.0 g) synthesized according to a method described in JP-A No. 2010-031259, bis(pinacolato)diboron (26.6 g), [1,1'-bis(diphenylphosphino) ferrocene]palladium (II) dichloride dichloromethane complex (PdCl$_2$ (dppf).CH$_2$12, 1.49 g), potassium acetate (26.8 g) and 1,4-dioxane (350 ml) were added, and the mixture was stirred for 4 hours under reflux with heating. The resultant reaction mixture was cooled down to room temperature, then, ethyl acetate was added. The resultant reaction liquid was washed with ion exchanged water. The resultant organic layer was dried over anhydrous sodium sulfate, then, filtrated, and the resultant filtrate was concentrated under reduced pressure, to obtain a solid. This solid was purified by silica gel column chromatography (a mixed solvent of hexane and toluene), then, re-crystallized using a mixed solvent of toluene and ethyl acetate and dried, to obtain a compound H5-1b (12.5 g, white solid). The compound H5-1b had an HPLC area percentage value of 99.5% or more.

LC-MS (ESI, positive): m/z=1192 [M]$^+$ (Synthesis of Compound H5-2b)

[Chemical Formula 67]

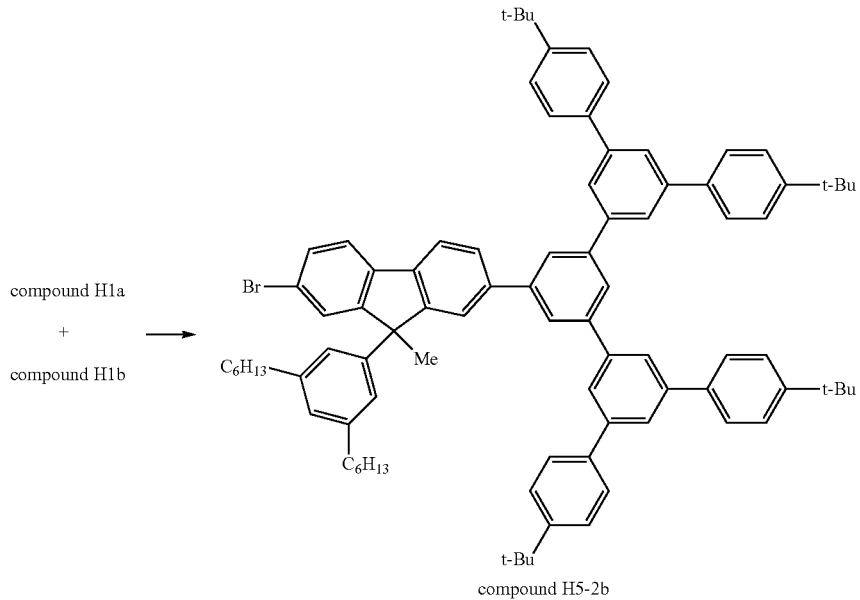

compound H1a
+
compound H1b
→
compound H5-2b

A nitrogen atmosphere was prepared in a reaction vessel, then, a compound H1a (5.00 g) synthesized according to a method described in JP-A No. 201.2-144722, a compound H1b (4.94 g) synthesized according to a method described in JP-A No. 2015-110751, dichlorobis(triphenylphosphine) palladium(II) (0.121 g), a 20 wt % tetraethylammonium hydroxide aqueous solution (2.53 g) and toluene (200 ml) were added, and the mixture was stirred at 55° C. for 2 hours. The resultant reaction mixture was cooled down to room temperature, then, ion exchanged water was added, and the mixed liquid was filtrated through a filter paved with Celite. The aqueous layer was removed from the resultant filtrate, then, the resultant organic layer was concentrated under reduced pressure. To the resultant concentrate were added hexane, toluene and activated carbon, and the mixture was stirred at room temperature for 1 hour, then, filtrated through a filter paved with Celite, and the filtrate was concentrated under reduced pressure, to obtain a solid. This solid was purified by silica gel column chromatography (a mixed solvent of hexane and toluene, and, a mixed solvent of hexane and ethyl acetate), to obtain a coarse product. This coarse product was washed with a mixed solvent of acetone and hexane, to obtain a solid. To this solid were added hexane, toluene and activated carbon, and the mixture was stirred at room temperature for 1 hour, then, filtrated through a filter paved with silica gel and Celite, and the resultant filtrate was concentrated under reduced pressure, to obtain a compound H5-2b (2.5 g). The compound H5-2b had an HPLC area percentage value of 99.25%.

LC-MS (ESI, positive): m/z=1259[M]

(Synthesis of Compound H5)

[Chemical Formula 68]
compound H5
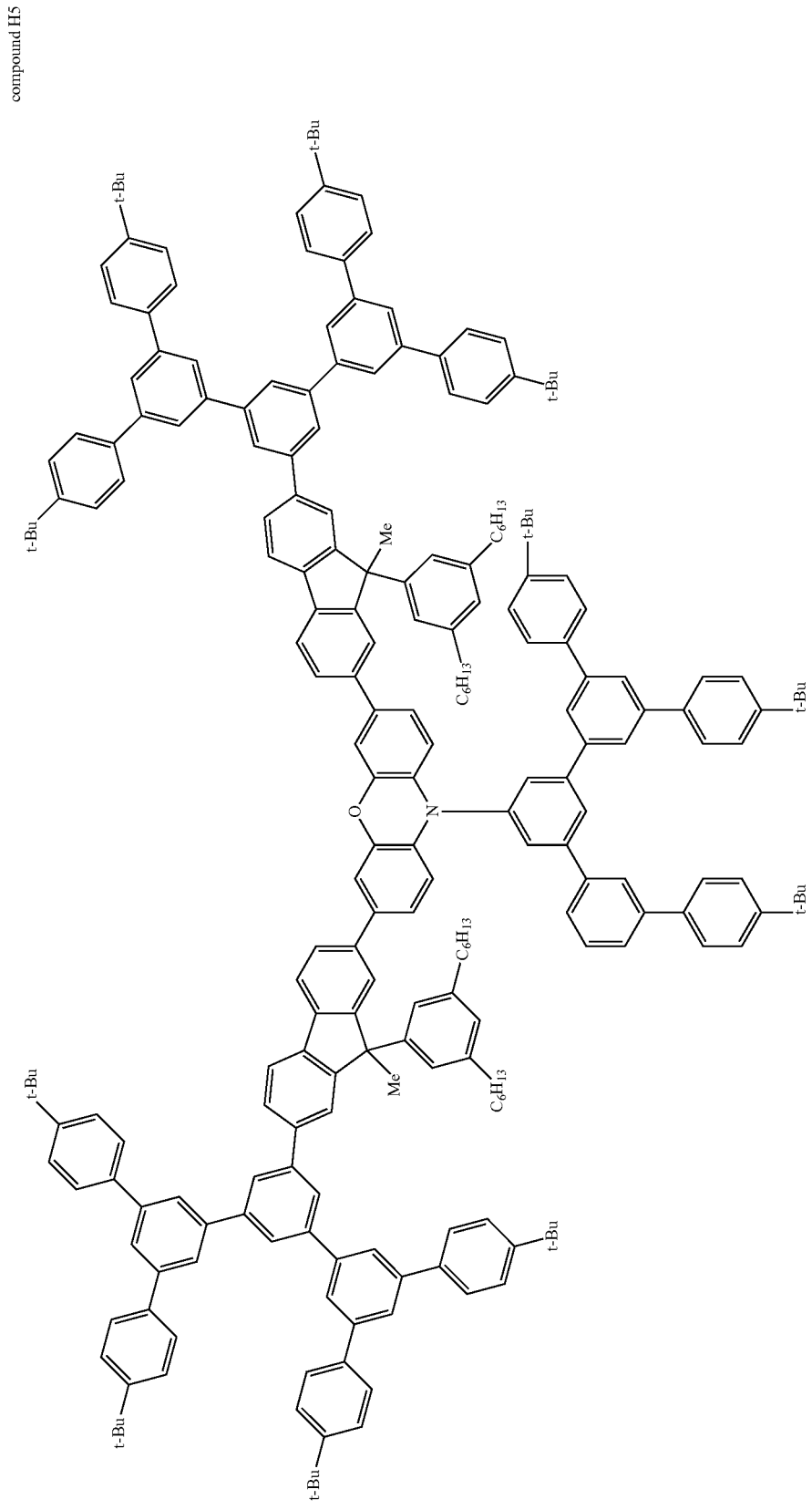

A nitrogen atmosphere was prepared in a reaction vessel, then, the compound H5-2b (2.45 g), the compound H5-1b (1.16 g), dichlorobis(triphenylphosphine)palladium(II) (55 mg), a 20 wt % tetraethylammonium hydroxide aqueous solution (1.15 g) and toluene (25 ml) were added, and the mixture was stirred at 55° C. for 2 hours. The resultant reaction mixture was cooled down to room temperature, then, ion exchanged water was added, and the mixed liquid was filtrated through a filter paved with Celite. The aqueous layer was removed from the resultant filtrate, then, the resultant organic layer was concentrated under reduced pressure. To the resultant concentrate were added toluene and activated carbon, and the mixture was stirred for 1 hour at 40° C., then, filtrated through a filter paved with Celite, and the resultant filtrate was concentrated under reduced pressure, to obtain a solid. This solid was purified by silica gel column chromatography (a mixed solvent of hexane and toluene), and further washed with methanol, then, dried, to obtain a compound H5 (0.83 g). The compound H5 had an HPLC area percentage value of 99.5% or more.

$^1$H-NMR (300 MHz, CDCl$_3$): δ=0.75 (t, 12H), 1.17-1.59 (m, 140H), 1.95 (s, 6H), 2.44 (t, 8H), 6.20 (d, 2H), 6.77-7.01 (m, 10H), 7.39-7.91 (m, 86H), 8.13 (s, 1H) LC-MS (ESI, positive): m/z=3297 [M]$^+$ <Synthesis Example H6> Synthesis of Compound H6

A compound H6 was synthesized based on a method described in International Publication WO2013/191088.

[Chemical Formula 69]

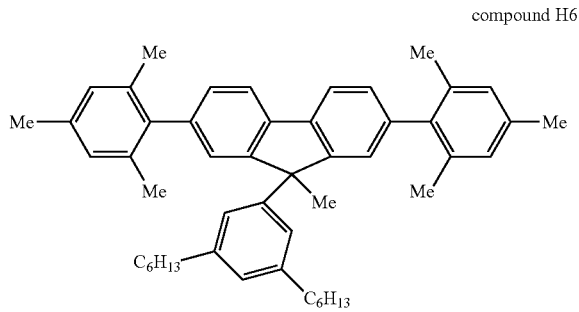

compound H6

<Synthesis Example ET1> Synthesis of Polymer Compound ET1

(Synthesis of Polymer Compound ET1a)

A polymer compound ET1a was synthesized according to a method disclosed in JP-A No. 2012-33845, using a compound ET1-1 synthesized according to a method disclosed in JP-A No. 2012-33845 and a compound ET1-2 synthesized according to a method disclosed in JP-A No. 2012-33845.

[Chemical Formula 70]

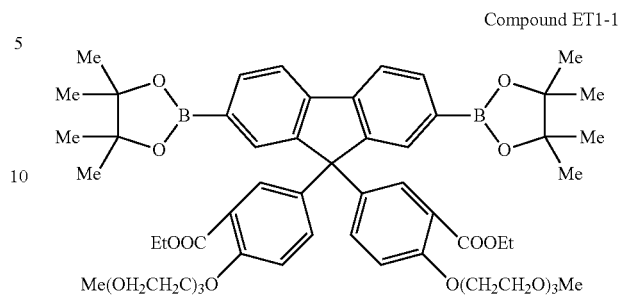

Compound ET1-1

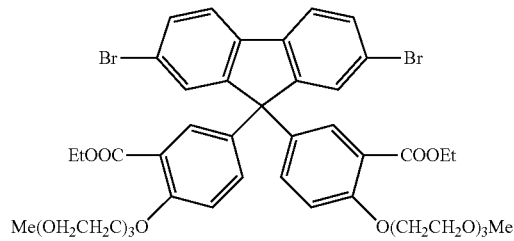

Compound ET1-2

The polymer compound ET1a had a Mn of 5.2×10$^4$.

The polymer compound ET1a is a copolymer constituted of a constitutional unit derived from a compound ET1-1 and a constitutional unit derived from a compound ET1-2 at a molar ratio of 50:50, according to theoretical values calculated from the amounts of charged raw materials.

(Synthesis of Polymer Compound ET1)

An inert gas atmosphere was prepared in a reaction vessel, then, a polymer compound ET1a (200 mg), tetrahydrofuran (20 ml) and ethanol (20 ml) were added, and the mixture was heated at 55° C. To the resultant mixture was added cesium hydroxide (200 mg) dissolved in water (2 ml), and the mixture was stirred at 55° C. for 6 hours. The resultant reaction mixture was cooled down to room temperature, then, concentrated under reduced pressure, to obtain a solid. The resultant solid was washed with water, then, dried under reduced pressure, to obtain a polymer compound ET1 (150 mg, pale-yellow solid). It was confirmed that a signal derived from an ethyl group of an ethyl ester portion of a polymer compound ET1a disappeared completely, by the NMR spectrum of the resultant polymer compound ET1.

[Chemical Formula 71]

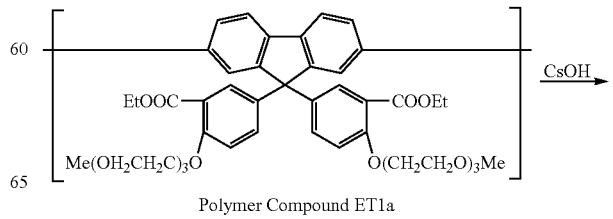

Polymer Compound ET1a

Polymer Compound ET1

Example D1

(Fabrication of Light Emitting Device D1)

An ITO film with a thickness of 45 nm was attached to glass substrate by a sputtering method, to form an anode. A polythiophene•sulfonic acid type hole injection agent AQ-1200 (manufactured by Plextronics) was spin-coated on the anode, to form a film with a thickness of 50 nm, and the film was heated on a hot plate at 170° C. for 15 minutes under an air atmosphere, to form a hole injection layer.

The polymer compound HTL-1 was dissolved in xylene at a concentration of 0.7 wt %. The resultant xylene solution was spin-coated on the hole injection layer, to form a film with a thickness of 20 nm, and the film was heated on a hot plate at 18000 for 60 minutes under a nitrogen gas atmosphere, to form a hole transporting layer.

The compound H1 and the phosphorescent compound G1 (compound H1/phosphorescent compound G1=70 wt %/30 wt %) were dissolved in chlorobenzene at a concentration of 2.0 wt. The resultant chlorobenzene solution was spin-coated on the hole transporting layer, to form a film with a thickness of 60 nm, and the film was heated at 130° C. for 10 minutes under a nitrogen gas atmosphere, to form a light emitting layer.

The substrate carrying thereon the light emitting layer formed was placed in a vapor deposition machine and the pressure in the machine was reduced to $1.0 \times 10^{-4}$ Pa or less, then, as the cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D1.

(Evaluation)

Voltage was applied to the light emitting device D1, to observe EL emission. Light emission efficiency at 100 cd/m was 9.18 cd/A. Light emission efficiency at 1000 cd/m$^2$ was 10.96 cd/A.

Example D2

(Fabrication of Light Emitting Device D2)

A light emitting device D2 was fabricated in the same manner as in Example D1, except that the compound H1 and the phosphorescent compound G2 (compound H1/phosphorescent compound G2=70 wt %/30 wt %) were used instead of the compound H1 and the phosphorescent compound G1 (compound H1/phosphorescent compound G1=70 wt %/30 wt %) in Example D1.

(Evaluation)

Voltage was applied to the light emitting device D2, to observe EL emission. Light emission efficiency at 10$^0$ cd/m$^2$ was 11.65 cd/A. Light emission efficiency at 1000 cd/m$^2$ was 17.12 cd/A.

Example D3

(Fabrication of Light Emitting Device D3)

A light emitting device D3 was fabricated in the same manner as in Example D1, except that the compound H1 and the phosphorescent compound G3 (compound H1/phosphorescent compound G3=70 wt %/30 wt %) were used instead of the compound H1 and the phosphorescent compound G1 (compound H1/phosphorescent compound G1=70 wt %/30 wt %) in Example D1.

(Evaluation)

Voltage was applied to the light emitting device D3, to observe EL emission. Light emission efficiency at 100 cd/m$^2$ was 22.65 cd/A. Light emission efficiency at 1000 cd/m$^2$ was 25.23 cd/A.

Example D4

(Fabrication of Light Emitting Device D4)

A light emitting device D4 was fabricated in the same manner as in Example D1, except that the compound H1 and the phosphorescent compound G4 (compound H1/phosphorescent compound G4=70 wt %/30 wt %) were used instead of the compound H1 and the phosphorescent compound G1 (compound H1/phosphorescent compound G1=70 wt %/30 wt %) in Example D1.

(Evaluation)

Voltage was applied to the light emitting device D4, to observe EL emission. Light emission efficiency at 100 cd/m$^2$ was 23.49 cd/A. Light emission efficiency at 1000 cd/m was 22.82 cd/A.

Comparative Example CD1

(Fabrication of Light Emitting Device CD1)

A light emitting device CD1 was fabricated in the same manner as in Example D1, except that "a compound HC1 and the phosphorescent compound G1 (compound HC1/phosphorescent compound G1=70 wt %/30 wt %) were dissolved in chlorobenzene at a concentration of 0.9 wt %." instead of "the compound H1 and the phosphorescent compound G1 (compound H1/phosphorescent compound G1=70 wt %/30 wt %) were dissolved in chlorobenzene at a concentration of 2.0 wt %." in Example D1.

The compound HC1 was synthesized based on a method described in Journal of Polymer Science, Part A: Polymer Chemistry, vol. 50, pp. 696-710, 2012.

[Chemical Formula 72]

compound HC1

(Evaluation)

Voltage was applied to the light emitting device CD1, to observe EL emission. Light emission efficiency at 100 cd/m$^2$ was 0.02 cd/A. Voltage was applied up to 12 V, but 1000 cd/m$^2$ was not attained.

Comparative Example CD2

(Fabrication of Light Emitting Device CD2)

A light emitting device CD2 was fabricated in the same manner as in Example D1, except that "a compound HC2 and the phosphorescent compound G1 (compound HC2/phosphorescent compound G1=70 wt %/30 wt %) were dissolved in chlorobenzene at a concentration of 2.5 wt %." instead of "the compound H1 and the phosphorescent compound G1 (compound H1/phosphorescent compound G1=70 wt %/30 wt %) were dissolved in chlorobenzene at a concentration of 2.0 wt %." in Example D1.

The compound HC2 was synthesized based on a method described in International Publication WO2008/150828.

[Chemical Formula 73]

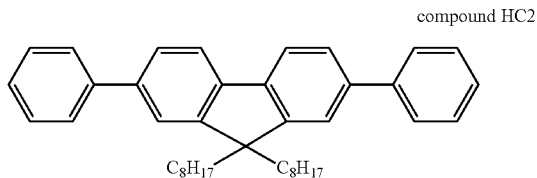

compound HC2

(Evaluation)

Voltage was applied to the light emitting device CD2, to observe EL emission. Light emission efficiency at 100=cd/m² was 0.07 cd/A. Voltage was applied up to 12 V, but 1000 cd/m² was not attained.

Comparative Example CD3

(Fabrication of Light Emitting Device CD3)

A light emitting device CD3 was fabricated in the same manner as in Example D1, except that a compound HC3 represented by the following formula and the phosphorescent compound G1 (compound HC3/phosphorescent compound G1=70 wt %/30 wt %) were used instead of the compound H1 and the phosphorescent compound G1 (compound H1/phosphorescent compound G1=70 wt %/30 wt %) in Example D1.

The compound HC3 was purchased from Luminescence Technology.

[Compound Formula 74]

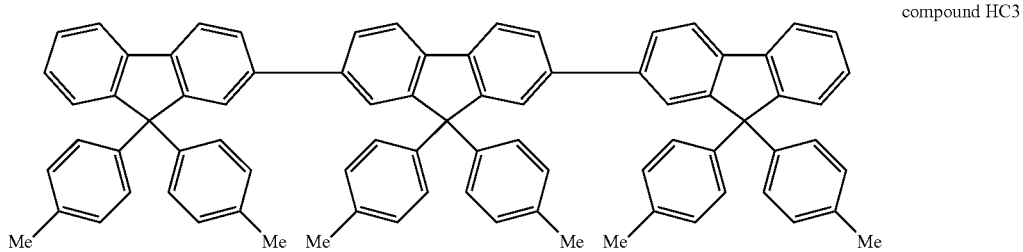

compound HC3

(Evaluation)

Voltage was applied to the light emitting device CD3, to observe EL emission. Voltage was applied to up to 12 V, but 100 cd/m² was not attained.

TABLE 4

| | light emitting device | light emitting layer composition | composition ratio (wt %) | light emission efficiency (cd/A) @100 cd/m² |
|---|---|---|---|---|
| Example D1 | D1 | H1/G1 | 70/30 | 9.18 |
| Example D2 | D2 | H1/G2 | 70/30 | 11.65 |
| Example D3 | D3 | H1/G3 | 70/30 | 22.65 |
| Example D4 | D4 | H1/G4 | 70/30 | 23.49 |
| Comparative Example CD1 | CD1 | HC1/G1 | 70/30 | 0.02 |
| Comparative Example CD2 | CD2 | HC2/G1 | 70/30 | 0.07 |

Example D5

(Fabrication of Light Emitting Device D5)

A light emitting device D5 was fabricated in the same manner as in Example D1, except that the compound 1-12 and the phosphorescent compound R1 (compound H2/phosphorescent compound R1=90 wt/10 wt %) were used instead of the compound H1 and the phosphorescent compound G1 (compound H1/phosphorescent compound G1=70 wt %/30 wt %) in Example D1.

(Evaluation)

Voltage was applied to the light emitting device D5, to observe EL emission. Light emission efficiency at 50 cd/m² was 2.32 cd/A. Light emission efficiency at 1000 cd/m² was 2.62 cd/A.

Example D6

(Fabrication of Light Emitting Device D6)

A light emitting device D6 was fabricated in the same manner as in Example D1, except that the compound H3 and the phosphorescent compound R1 (compound H3/phosphorescent compound R1=90 wt %/10 wt %) were used instead of the compound H1 and the phosphorescent compound G1 (compound H1/phosphorescent compound G1=70 wt %/30 wt %) in Example D1.

(Evaluation)

Voltage was applied to the light emitting device D6, to observe EL emission. Light emission efficiency at 50 cd/m² was 1.60 cd/A. Light emission efficiency at 1000 cd/m² was 2.14 cd/A.

Example D7

(Fabrication of Light Emitting Device D7)

A light emitting device D7 was fabricated in the same manner as in Example D1, except that the compound H2 and the phosphorescent compound R2 (compound H2/phosphorescent compound R2=90 wt % 10 wt %) were used instead of the compound H1 and the phosphorescent compound G1 (compound H1/phosphorescent compound G4==70 wt %/30 wt %) in Example D1.

(Evaluation)

Voltage was applied to the light emitting device D7, to observe EL emission. Light emission efficiency at 50 cd/m$^2$ was 3.14 cd/A. Light emission efficiency at 1000 cd/m$^2$ was 3.54 cd/A.

Example D8

(Fabrication of Light Emitting Device D8)

A light emitting device D8 was fabricated in the same manner as in Example D1, except that the compound H3 and the phosphorescent compound R2 (compound H3/phosphorescent compound R2=90 wt %/10 wt %) were used instead of the compound H1 and the phosphorescent compound G1 (compound H1/phosphorescent compound G1=70 wt %/30 wt %) in Example D1.

(Evaluation)

Voltage was applied to the light emitting device D8, to observe EL emission. Light emission efficiency at 50 cd/m$^2$ was 1.82 cd/A. Light emission efficiency at 1000 cd/m$^2$ was 2.32 cd/A.

Comparative Example CD4

(Fabrication of Light Emitting Device CD4)

A light emitting device CD4 was fabricated in the same manner as in Example D1, except that "the compound HC1 and the phosphorescent compound R1 (compound HC1/phosphorescent compound R1=90 wt %/10 wt %) were dissolved in chlorobenzene at a concentration of 1.5 wt %." instead of "the compound H1 and the phosphorescent compound G1 (compound H1/phosphorescent compound G1=70 wt %/30 wt %) were dissolved in chlorobenzene at a concentration of 2.0 wt %." in Example D1.

(Evaluation)

Voltage was applied to the light emitting device CD4, to observe EL emission. Voltage was applied up to 12 V, but 50 cd/m$^2$ was not attained.

Comparative Example CD5

(Fabrication of Light Emitting Device CD5)

A light emitting device CD5 was fabricated in the same manner as in Example D1, except that "the compound HC2 and the phosphorescent compound R1 (compound HC2/phosphorescent compound R1=90 wt %/10 wt %) were dissolved in chlorobenzene at a concentration of 2.5 wt %." instead of "the compound H1 and the phosphorescent compound G1 (compound H1/phosphorescent compound G1=70 wt %/30 wt %) were dissolved in chlorobenzene at a concentration of 2.0 wt %." in Example D1.

(Evaluation)

Voltage was applied to the light emitting device CD5, to observe EL emission. Voltage was applied up to 12 V, but 50 cd/m was not attained.

Comparative Example CD6

(Fabrication of Light Emitting Device CD6)

A light emitting device CD6 was fabricated in the same manner as in Example D1, except that "the compound HC3 and the phosphorescent compound R1 (compound HC3/phosphorescent compound R1=90 wt %/10 wt %) were dissolved in chlorobenzene at a concentration of 1.7 wt %." instead of "the compound H1 and the phosphorescent compound G1 (compound H1/phosphorescent compound G1=70 wt %/30 wt %) were dissolved in chlorobenzene at a concentration of 2.0 wt %." in Example D1.

(Evaluation)

Voltage was applied to the light emitting device CD6, to observe EL emission. Light emission efficiency at 50 cd/m$^2$ was 0.16 cd/A. Voltage was applied up to 12 V, but 1000 cd/m$^2$ was not attained.

TABLE 5

| | light emitting device | light emitting layer composition | composition ratio (wt %) | light emission efficiency (cd/A) @50 cd/m$^2$ |
|---|---|---|---|---|
| Example D5 | D5 | H2/R1 | 90/10 | 2.32 |
| Example D6 | D6 | H3/R1 | 90/10 | 1.60 |
| Example D7 | D7 | H2/R2 | 90/10 | 3.14 |
| Example D8 | D8 | H3/R2 | 90/10 | 1.82 |
| Comparative Example CD6 | CD6 | HC3/R1 | 90/10 | 0.16 |

Example D9

(Fabrication of Light Emitting Device D9)

An ITO film with a thickness of 45 nm was attached to a glass substrate by a sputtering method, to form an anode. A hole injection material ND-3202 (manufactured by Nissan Chemical industries, Ltd.) was spin-coated on the anode, to form a film with a thickness of 65 nm. The film was heated at 50° C. for 3 minutes under an air atmosphere, and further heated at 230° C. for 15 minutes, to form a hole injection layer.

The polymer compound HTL-1 was dissolved in xylene at a concentration of 0.7 wt %. The resultant xylene solution was spin-coated on the hole injection layer, to form a film with a thickness of 20 nm, and the film was heated on a hot plate at 180° C. for 60 minutes under a nitrogen gas atmosphere, to form a hole transporting layer.

The polymer compound HP-1, the compound H4 and the phosphorescent compound R1 (polymer compound HP-1/compound H4/phosphorescent compound R1=85 wt %/5 wt %/10 wt %) were dissolved in chlorobenzene at a concentration of 1.1 wt %. The resultant chlorobenzene solution was spin-coated on the hole transporting layer, to form a film with a thickness of 60 nm, and the film was heated at 150° C. for 10 minutes under a nitrogen gas atmosphere, to form a light emitting layer.

The substrate carrying thereon the light emitting layer formed was placed in a vapor deposition machine and the pressure in the machine was reduced to $1.0 \times 10^{-4}$ Pa or less, then, as the cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D9.

(Evaluation)

Voltage was applied to the light emitting device D9, to observe EL emission. Light emission efficiency at 3000 cd/m was 3.14 cd/A. Light emission efficiency at 5000 cd/m$^2$ was 3.18 cd/A.

Example D10

(Fabrication of Light Emitting Device D10)

A light emitting device D10 was fabricated in the same manner as in Example D9, except that the polymer compound HP-1, the compound H4 and the phosphorescent compound R2 (polymer compound HP-1/compound H4/phosphorescent compound R2=85, wt/5 wt %/10 wt %) were used instead of the polymer compound HP-1, the compound H4 and the phosphorescent compound R1 (polymer compound HP-1/compound H4/phosphorescent compound R1=85 wt %/5 wt %/10 wt %) in Example D9.

(Evaluation)

Voltage was applied to the light emitting device D10, to observe EL emission. Light emission efficiency at 3000 cd/m was 5.08 cd/A. Light emission efficiency at 5000 cd/m$^2$ was 4.67 cd/A.

Example D11

(Fabrication of Light Emitting Device D11)

A light emitting device D11 was fabricated in the same manner as in Example D9, except that the polymer compound HP-1, the compound H5 and the phosphorescent compound R1 (polymer compound HP-1/compound H5/phosphorescent compound R1=85 wt %/5 wt %/10 wt %) were used instead of the polymer compound HP-1, the compound H4 and the phosphorescent compound R1 (polymer compound HP-1/compound H4/phosphorescent compound R1=85 wt %/5 wt %/10 wt %) in Example D9.

(Evaluation)

Voltage was applied to the light emitting device D11, to observe EL emission. Light emission efficiency at 3000 cd/m$^2$ was 3.22 cd/A. Light emission efficiency at 5000 cd/m$^2$ was 3.17 cd/A.

Example D12

(Fabrication of Light Emitting Device D12)

A light emitting device D12 was fabricated in the same manner as in Example D9, except that the polymer compound HP-1, the compound H5 and the phosphorescent compound R1 (polymer compound HP-1/compound H5/phosphorescent compound R2=85 wt %/5 wt %/10 wt %) were used instead of the polymer compound HP-1, the compound H4 and the phosphorescent compound R1 (polymer compound HP-1/compound H4/phosphorescent compound R1=85 wt %/5 wt %/10 wt %) in Example D9.

(Evaluation)

Voltage was applied to the light emitting device D12, to observe EL emission. Light emission efficiency at 3000 cd/m$^2$ was 5.07 cd/A. Light emission efficiency at 5000 cd/m$^2$ was 4.63 cd/A.

Comparative Example CD7

(Fabrication of Light Emitting Device CD7)

A light emitting device CD7 was fabricated in the same manner as in Example D9, except that the polymer compound HP-1, a compound HC4 represented by the following formula and the phosphorescent compound R1 (polymer compound HP-1/compound HC4/phosphorescent compound R1=85 wt %/5 wt %/10 wt %) were used instead of the polymer compound HP-1, the compound H4 and the phosphorescent compound R1 (polymer compound HP-1/compound H4/phosphorescent compound R1=85 wt %/5 wt %/10 wt %) in Example D9.

The compound HC4 was synthesized based on a method described in International Publication WO2005/049546.

[Chemical Formula 75]

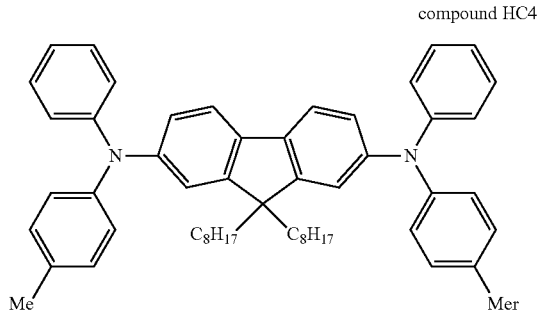

compound HC4

(Evaluation)

Voltage was applied to the light emitting device CD7, to observe EL emission Light emission efficiency at 3000 cd/m$^2$ was 1.91 cd/A. Voltage was applied up to 12 V, but 5000 cd/m$^2$ was not attained.

TABLE 6

| | light emitting device | light emitting layer composition | composition ratio (wt %) | light emission efficiency (cd/A) @3000 cd/m$^2$ |
|---|---|---|---|---|
| Example D9 | D9 | HP-1/H4/R1 | 85/5/10 | 3.14 |
| Example D10 | D10 | HP-1/H4/R2 | 85/5/10 | 5.08 |
| Example D11 | D11 | HP-1/H5/R1 | 85/5/10 | 3.22 |
| Example D12 | D12 | HP-1/H5/R2 | 85/5/10 | 5.07 |
| Comparative Example CD7 | CD7 | HP-1/HC4/R1 | 85/5/10 | 1.91 |

Example D13

(Fabrication of Light Emitting Device D13)

A light emitting device D13 was fabricated in the same manner as in Example D9, except that "the polymer compound HP-2, the compound 1-14 and the phosphorescent compound G1 (polymer compound HP-2/compound H/phosphorescent compound G1===65 wt %/5 wt %/30 wt %) were dissolved in chlorobenzene at a concentration of 1.6 wt %." instead of "the polymer compound HP-1, the compound H4 and the phosphorescent compound R1 (polymer compound HP-1/compound H4/phosphorescent compound R1=85 wt %/5 wt %/10 wt %) were dissolved in chlorobenzene at a concentration of 1.1 wt %." in Example D9.

(Evaluation)

Voltage was applied to the light emitting device D13, to observe EL emission. Light emission efficiency at 500 cd/m was 27.74 cd/A.

Example D14

(Fabrication of Light Emitting Device D14)

A light emitting device D14 was fabricated in the same manner as in Example D9, except that "the polymer compound HP-2, the compound H4 and the phosphorescent compound G2 (polymer compound HP-2/compound H4/phosphorescent compound G2=65 wt %/5 wt %/30 wt %) were dissolved in chlorobenzene at a concentration of 1.6 wt %." instead of "the polymer compound HP-1, the compound H4 and the phosphorescent compound R1 (polymer compound HP-1/compound H4/phosphorescent compound R1=85 wt %/5 wt %/10 wt %) were dissolved in chlorobenzene at a concentration of 1.1 wt %." in Example D9.

(Evaluation)

Voltage was applied to the light emitting device D14, to observe EL emission. Light emission efficiency at 500 cd/m² was 59.06 cd/A.

TABLE 7

| light emitting device | light emitting layer composition | composition ratio (wt %) | light emission efficiency (cd/A) @500 cd/m² |
|---|---|---|---|
| Example D13 | D13 | HP-2/H4/G1 | 65/5/30 | 27.74 |
| Example D14 | D14 | HP-2/H4/G2 | 65/5/30 | 59.06 |

Example D15

(Fabrication of Light Emitting Device D15)

An ITO film with a thickness of 45 nm was attached to a glass substrate by a sputtering method, to form an anode. A hole injection material ND-3202 (manufactured by Nissan Chemical Industries, Ltd.) was spin-coated on the anode, to form a film with a thickness of 35 nm. The film was heated on a hot plate at 50° C. for 3 minutes under an air atmosphere, and further heated at 230° C. for 15 minutes, to form a hole injection layer.

The polymer compound HTL-2 was dissolved in xylene at a concentration of 0.7 wt %. The resultant xylene solution was spin-coated on the hole injection layer to form a film with a thickness of 20 nm, and the film was heated on a hot plate at 180° C. for 60 minutes under a nitrogen gas atmosphere, to form a hole transporting layer.

A compound HM-1 represented by the following formula, the compound 1-16 and the phosphorescent compound B31 (compound HM-1/compound H6/phosphorescent compound B1=70 wt %/5 wt %/25 wt %) were dissolved in chlorobenzene at a concentration of 1.6 wt %. The resultant chlorobenzene solution was spin-coated on the hole transporting layer to form a film with a thickness of 75 nm, and the film was heated at 130° C. for 10 minutes under a nitrogen gas atmosphere, to form a light emitting layer.

The compound HM-1 was purchased from Luminescence Technology.

[Chemical Formula 76]

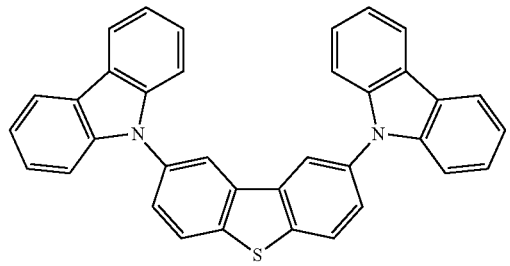

compound HM-1

The polymer compound ET1 was dissolved in 2,2,3,3,4,4,5,5-octafluoro-1-pentanol at a concentration of 0.25 wt %. The resultant 2,2,3,3,4,4,5,5-octafluoro-1-pentanol solution was spin-coated on the light emitting layer to form a film with a thickness of 10 nm, and the film was heated at 130° C. for 10 minutes under a nitrogen gas atmosphere, to form an electron transporting layer.

The substrate carrying thereon the electron transporting layer formed was placed in a vapor deposition machine and the pressure in the machine was reduced to $1.0 \times 10^{-4}$ Pa or less, then, as the cathode, sodium fluoride was vapor-deposited with a thickness of about 4 nm on the electron transporting layer, then, aluminum was vapor-deposited with a thickness of about 80 nm on the sodium fluoride layer. After vapor deposition, sealing was performed using a glass substrate, to fabricate a light emitting device D15.

(Evaluation)

Voltage was applied to the light emitting device D15, to observe EL emission. Light emission efficiency at 400 cd/m² was 5.67 cd/A. Light emission efficiency at 5000 cd/m was 5.95 cd/A.

Comparative Example CD8

(Fabrication of Light Emitting Device CD8)

A light emitting device CD8 was fabricated in the same manner as in Example D15, except that the compound HM-1, the compound HC2 and the phosphorescent compound B1 (compound HM-1/compound HC2/phosphorescent compound B1=70 wt %/5 wt %/25 wt % were used instead of the compound HM-1, the compound H6 and the phosphorescent compound B1 (compound HM-1/compound H6/phosphorescent compound B1=70 wt %/5 wt %/25 wt %) in Example D15.

(Evaluation)

Voltage was applied to the light emitting device CD8, to observe EL emission. Light emission efficiency at 400 cd/m² was 2.96 cd/A. Light emission efficiency at 5000 cd/m² was 2.58 cd/A.

TABLE 8

| light emitting device | light emitting layer composition | composition ratio (wt %) | light emission efficiency (cd/A) @5000 cd/m² |
|---|---|---|---|
| Example D15 | D15 | HM-1/H6/B1 | 70/5/25 | 5.95 |
| Comparative Example CD8 | CD8 | HM-1/HC2/B1 | 70/5/25 | 2.58 |

INDUSTRIAL APPLICABILITY

According to the present invention, a composition which is useful for production of a light emitting device excellent in light emission efficiency can be provided. Further, according to the present invention, a light emitting device comprising this composition can be provided.

The invention claimed is:

1. A composition comprising a low molecular weight compound represented by the formula (1) and a phosphorescent compound:

wherein
R$^1$ and R$^2$ each independently represent an aryl group, a monovalent heterocyclic group or a substituted amino group and these groups each optionally have a substituent,
n$^1$ represents an integer of 1 to 14, and
Ar$^1$ represents an arylene group or a divalent heterocyclic group and these groups each optionally have a substituent, and when a plurality of Ar$^1$ are present, they may be the same or different, and at least one of one or more groups Ar$^1$ is a group represented by the formula (1-A):

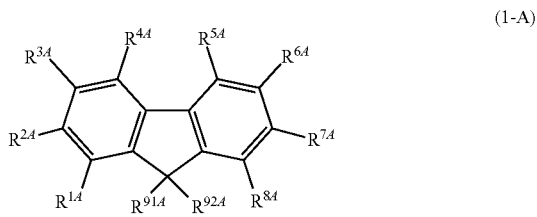

wherein
R$^{1A}$, R$^{2A}$, R$^{3A}$, R$^{6A}$, R$^{7A}$, R$^{8A}$ each independently represent a connecting bond, a hydrogen atom, an alkyl group, a cycloalkyl group, an alkoxy group, a cycloalkoxy group, an aryl group, an aryloxy group, a monovalent heterocyclic group, a substituted amino group or a halogen atom and these groups each optionally have a substituent,
R$^{4A}$ and R$^{5A}$ each independently represent a connecting bond, a hydrogen atom, an alkyl group, a cycloalkyl group, an alkoxy group, a cycloalkoxy group, an aryloxy group, a monovalent heterocyclic group, a substituted amino group or a halogen atom and these groups each optionally have a substituent,
and one of R$^{1A}$, R$^{2A}$, R$^{3A}$ and R$^{4A}$ is a connecting bond, and one of R$^{5A}$, R$^{6A}$, R$^{7A}$ and R$^{8A}$ is a connecting bond,
R$^{1A}$ and R$^{2A}$, R$^{2A}$ and R$^{3A}$, R$^{3A}$ and R$^{4A}$, R$^{5A}$ and R$^{6A}$, R$^{6A}$ and R$^{7A}$, and R$^{7A}$ and R$^{8A}$ each may be combined together to form a ring together with the carbon atoms to which they are attached,
R$^{91A}$ is an alkyl group optionally having a substituent or a cycloalkyl group optionally having a substituent,
R$^{92A}$ is an aryl group optionally having a substituent, wherein the phosphorescent compound is a metal complex represented by the formula (M):

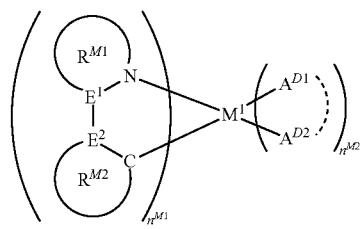

wherein
M$^1$ represents an iridium atom or a platinum atom,
n$^{M1}$ represents an integer of 1 or more, n$^{M2}$ represents an integer of 0 or more, and n$^{M1}$+n$^{M2}$ is 2 or 3, and n$^{M1}$+n$^{M2}$ is 3 when M$^1$ is an iridium atom, while n$^{M1}$+n$^{M2}$ is 2 when M$^1$ is a platinum atom,
E$^1$ and E$^2$ each independently represent a carbon atom or a nitrogen atom, and at least one of E$^1$ and E$^2$ is a carbon atom,
the ring R$^{M1}$ represents an aromatic heterocyclic ring and this ring optionally has a substituent, and when a plurality of the substituents are present, they may be the same or different and may be combined together to form a ring together with the atoms to which they are attached, and when a plurality of the rings R$^{M1}$ are present, they may be the same or different,
the ring R$^{M2}$ represents an aromatic hydrocarbon ring or an aromatic heterocyclic ring and these rings each optionally have a substituent, and when a plurality of the substituents are present, they may be the same or different and may be combined together to form a ring together with the atoms to which they are attached, and when a plurality of the rings R$^{M2}$ are present, they may be the same or different,
the substituent which the ring R$^{M1}$ optionally has and the substituent which the ring R$^{M2}$ optionally has may be combined together to form a ring together with the atoms to which they are attached, and
-A$^{D1}$---A$^{D2}$- represents an anionic bidentate ligand, and A$^{D1}$ and A$^{D2}$ each independently represent a carbon atom, an oxygen atom or a nitrogen atom bonding to an iridium atom, and these atoms may be an atom constituting a ring, and when a plurality of -A$^{D1}$---A$^{D2}$- are present, they may be the same or different.

2. The composition according to claim 1, wherein one of R$^{2A}$ and R$^{3A}$ is a connecting bond, and one of R$^{6A}$ and R$^{7A}$ is a connecting bond.

3. The composition according to claim 1, wherein R$^1$ and R$^2$ represent a group represented by the formula (D-A), a group represented by the formula (D-B) or a group represented by the formula (D-C):

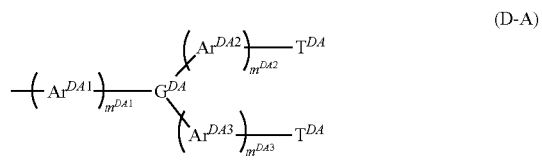

wherein
m$^{DA1}$, m$^{DA2}$ and m$^{DA3}$ each independently represent an integer of 0 or more, $G^{DA}$ represents a nitrogen atom, an aromatic hydrocarbon group or a heterocyclic group and these groups each optionally have a substituent, $Ar^{DA1}$, $Ar^{DA2}$ and $Ar^{DA3}$ each independently represent an arylene group or a divalent heterocyclic group and these groups each optionally have a substituent, and when a plurality of $Ar^{DA1}$, $Ar^{DA2}$ and $Ar^{DA3}$ are present, they may be the same or different at each occurrence, and $T^{DA}$ represents an aryl group or a monovalent heterocyclic group and these groups each optionally have a substituent, and the plurality of $T^{DA}$ may be the same or different:

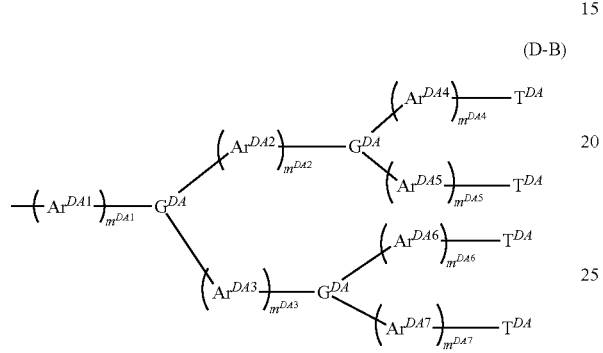
(D-B)

wherein
$m^{DA1}$, $m^{DA2}$, $m^{DA3}$, $m^{DA4}$, $m^{DA5}$, $m^{DA6}$ and $m^{DA7}$ each independently represent an integer of 0 or more, $G^{DA}$ represents a nitrogen atom, an aromatic hydrocarbon group or a heterocyclic group and these groups each optionally have a substituent, and the plurality of $G^{DA}$ may be the same or different, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and these groups each optionally have a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence, and $T^{DA}$ represents an aryl group or a monovalent heterocyclic group and these groups each optionally have a substituent, and the plurality of $T^{DA}$ may be the same or different:

(D-C)

wherein
$m^{DA1}$ represents an integer of 0 or more, $Ar^{DA1}$ represents an arylene group or a divalent heterocyclic group and these groups each optionally have a substituent, and when a plurality of $Ar^{DA1}$ are present, they may be the same or different, and $T^{DA}$ represents an aryl group or a monovalent heterocyclic group and these groups each optionally have a substituent.

4. The composition according to claim 3, wherein the group represented by the formula (D-A) is a group represented by the formula (D-A1), a group represented by the formula (D-A2), a group represented by the formula (D-A3) or a group represented by the formula (D-A4):

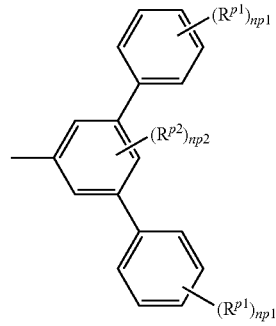
(DA1)

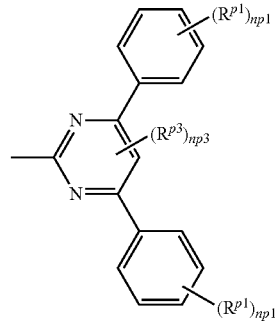
(DA2)

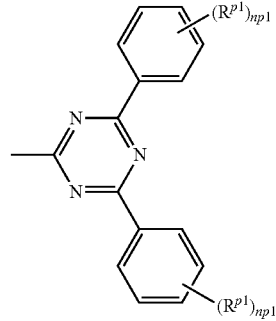
(DA3)

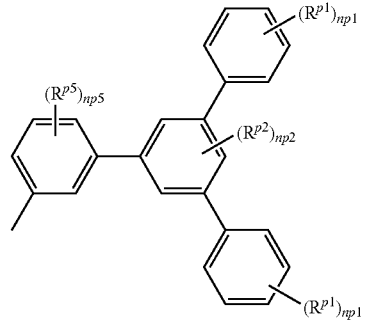
(DA4)

wherein
$R^{p1}$, $R^{p2}$, $R^{p3}$ and $R^{p5}$ each independently represent an alkyl group, a cycloalkyl group, an alkoxy group, a cycloalkoxy group or a halogen atom, and when a plurality of $R^{p1}$, $R^{p2}$ and $R^{p5}$ are present, they may be the same or different at each occurrence, and np1 represents an integer of 0 to 5, np2 represents an integer of 0 to 3, np3 represents 0 or 1, and np5 represents an integer of 0 to 4, and the plurality of np1 may be the same or different.

5. The composition according to claim 3, wherein the group represented by the formula (D-B) is a group represented by the formula (D-B1), a group represented by the formula (D-B2) or a group represented by the formula (D-B3):

(D-B1)

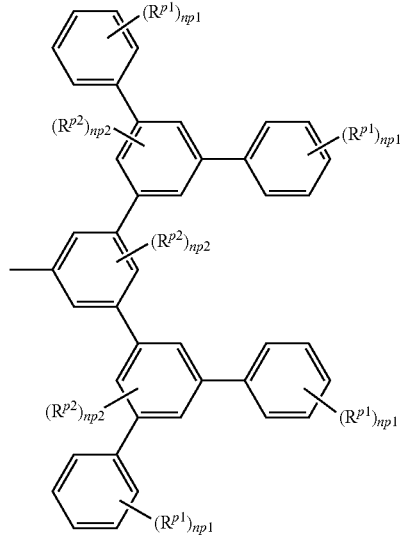

(D-B2)

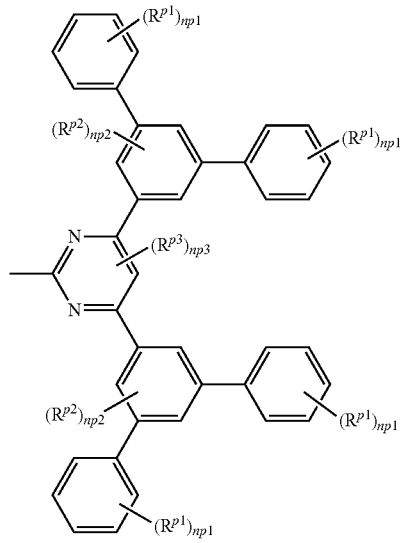

(D-B3)

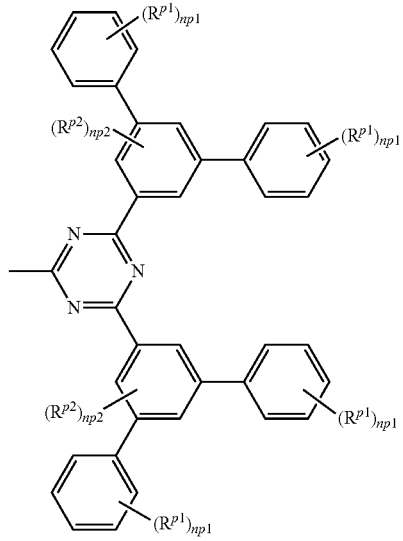

wherein $R^{p1}$, $R^{p2}$ and $R^{p3}$ each independently represent an alkyl group, a cycloalkyl group, an alkoxy group, a cycloalkoxy group or a halogen atom, and when a plurality of $R^{p1}$ and $R^{p2}$ are present, they may be the same or different at each occurrence, and np1 represents an integer of 0 to 5, np2 represents an integer of 0 to 3, and np3 represents 0 or 1, and the plurality of np1 and np2 may be the same or different at each occurrence.

6. The composition according to claim 3, wherein the group represented by the formula (D-C) is a group represented by the formula (D-C1), a group represented by the formula (D-C2), a group represented by the formula (D-C3) or a group represented by the formula (D-C4):

(D-C1)

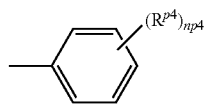

(D-C2)

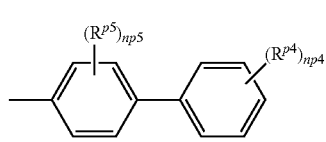

(D-C3)

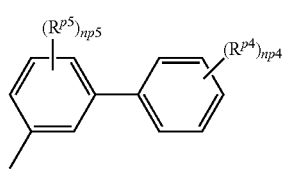

(D-C4)

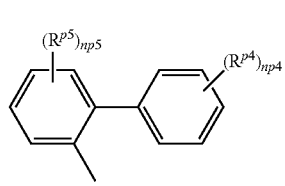

wherein

R$^{p4}$ and R$^{p5}$ each independently represent an alkyl group, a cycloalkyl group, an alkoxy group, a cycloalkoxy group or a halogen atom, and when a plurality of R$^{p4}$ and R$^{p5}$ are present, they may be the same or different at each occurrence, and np4 represents an integer of 0 to 5, and np5 represents an integer of 0 to 4.

7. The composition according to claim 1, wherein all of n$^1$ groups Ar$^1$ are groups represented by the formula (1-A).

8. The composition according to claim 1, wherein the metal complex represented by the formula (M) is a metal complex represented by the formula Ir-1, a metal complex represented by the formula Ir-2, a metal complex represented by the formula Ir-3, a metal complex represented by the formula Ir-4 or a metal complex represented by the formula Ir-5:

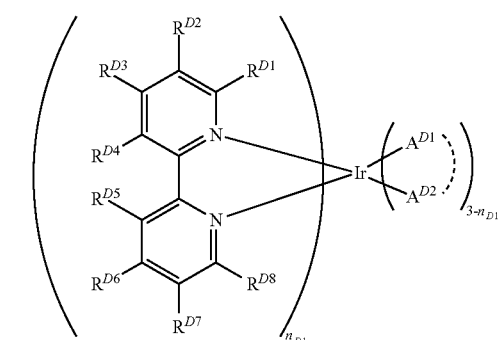

Ir-1

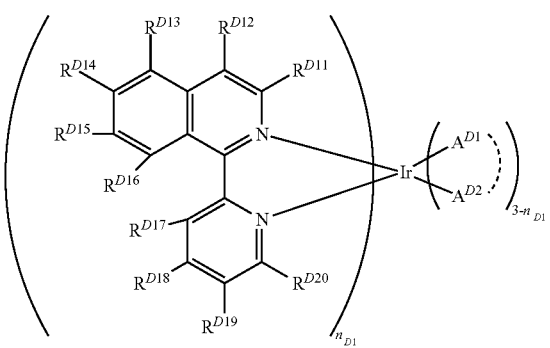

Ir-2

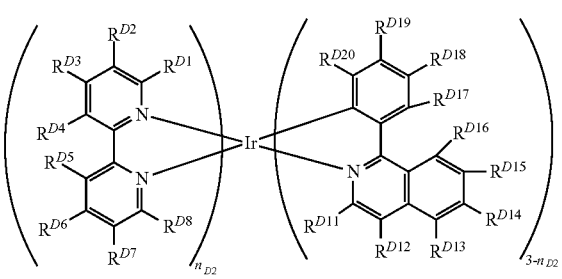

Ir-3

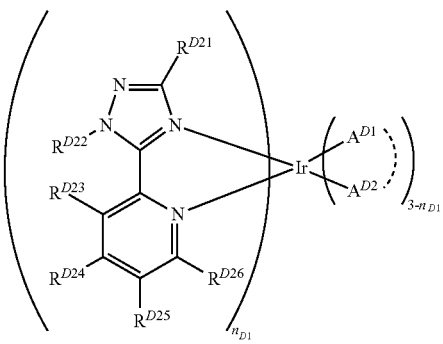

Ir-4

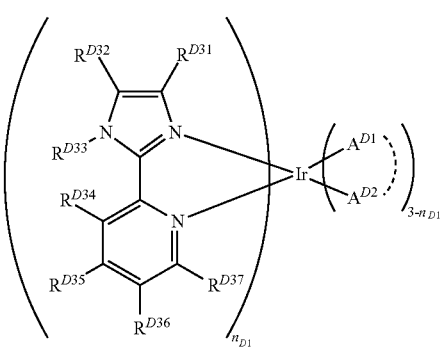

Ir-5 wherein

R$^{D1}$, R$^{D2}$, R$^{D3}$, R$^{D4}$, R$^{D5}$, R$^{D6}$, R$^{D7}$, R$^{D8}$, R$^{D11}$, R$^{D12}$, R$^{D13}$, R$^{D14}$, R$^{D15}$, R$^{D16}$, R$^{D17}$, R$^{D18}$, R$^{D19}$, R$^{D20}$, R$^{D21}$, R$^{D22}$, R$^{D23}$, R$^{D24}$, R$^{D25}$, R$^{D26}$, R$^{D31}$, R$^{D32}$, R$^{D33}$, R$^{D34}$, R$^{D35}$, R$^{D36}$ and R$^{D37}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom and these groups each optionally have a substituent, and when a plurality of R$^{D1}$, R$^{D2}$, R$^{D3}$, R$^{D4}$, R$^{D5}$, R$^{D6}$, R$^{D7}$, R$^{D8}$, R$^{D11}$, R$^{D12}$, R$^{D13}$, R$^{D14}$, R$^{D15}$, R$^{D16}$, R$^{D17}$, R$^{D18}$, R$^{D19}$, R$^{D20}$, R$^{D21}$, R$^{D22}$, R$^{D23}$, R$^{D24}$, R$^{D25}$, R$^{D26}$, R$^{D31}$, R$^{D32}$, R$^{D33}$, R$^{D34}$, R$^{D35}$, R$^{D36}$ and R$^{D37}$ are present, they may be the same or different at each occurrence, -A$^{D1}$---A$^{D2}$- represents the same meaning as described above, and n$_{D1}$ represents 1, 2 or 3, and n$_{D2}$ represents 1 or 2.

9. The composition according to claim 1, further comprising at least one material selected from the group consisting of a hole transporting material, a hole injection material, an electron transporting material, an electron injection material, a light emitting material and an antioxidant.

10. The composition according to claim 1, further comprising a solvent.

11. A light emitting device comprising the composition according to claim 1.

12. The composition according to claim 1, wherein at least one ring selected from the ring R$^{M1}$ and the ring R$^{M2}$ has a substituent represented by the formula (D-A), a substituent represented by the formula (D-B), or a substituent represented by the formula (D-C):

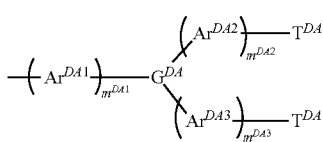
(D-A)

wherein
$m^{DA1}$, $m^{DA2}$ and $m^{DA3}$ each independently represent an integer of 0 or more, $G^{DA}$ represents a nitrogen atom, an aromatic hydrocarbon group or a heterocyclic group and these groups each optionally have a substituent, $Ar^{DA1}$, $Ar^{DA2}$ and $Ar^{DA3}$ each independently represent an arylene group or a divalent heterocyclic group and these groups each optionally have a substituent, and when a plurality of $Ar^{DA1}$, $Ar^{DA2}$ and $Ar^{DA3}$ are present, they may be the same or different at each occurrence, and $T^{DA}$ represents an aryl group or a monovalent heterocyclic group and these groups each optionally have a substituent, and the plurality of $T^{DA}$ may be the same or different,

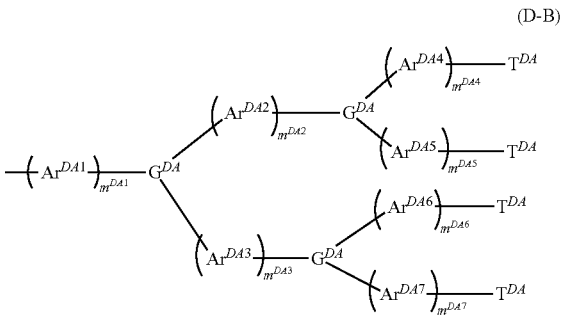
(D-B)

wherein
$m^{DA1}$, $m^{DA2}$, $m^{DA3}$, $m^{DA4}$, $m^{DA5}$, $m^{DA6}$ and $m^{DA7}$ each independently represent an integer of 0 or more, $G^{DA}$ represents a nitrogen atom, an aromatic hydrocarbon group or a heterocyclic group and these groups each optionally have a substituent, and the plurality of $G^{DA}$ may be the same or different, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and these groups each optionally have a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence, and $T^{DA}$ represents an aryl group or a monovalent heterocyclic group and these groups each optionally have a substituent, and the plurality of $T^{DA}$ may be the same or different,

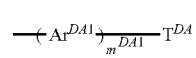
(D-C)

wherein
$m^{DA1}$ represents an integer of 0 or more, $Ar^{DA1}$ represents an arylene group or a divalent heterocyclic group and these groups each optionally have a substituent, and when a plurality of $Ar^{DA1}$ are present, they may be the same or different, and $T^{DA}$ represents an aryl group or a monovalent heterocyclic group and these groups each optionally have a substituent.

13. The composition according to claim 1, wherein $R^{4A}$ and $R^{5A}$ are each a hydrogen atom.

* * * * *